US010736959B2

(12) United States Patent
Berti et al.

(10) Patent No.: US 10,736,959 B2
(45) Date of Patent: *Aug. 11, 2020

(54) **CONJUGATION OF *STAPHYLOCOCCUS AUREUS* TYPE 5 AND TYPE 8 CAPSULAR POLYSACCHARIDES**

(71) Applicant: GLAXOSMITHKLINE BIOLOGICALS, SA, Rixensart (BE)

(72) Inventors: Francesco Berti, Colle Val D'Elsa (IT); Paolo Costantino, Colle Val D'Elsa (IT); Maria Rosaria Romano, Pontedera (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/809,524

(22) Filed: Nov. 10, 2017

(65) Prior Publication Data
US 2018/0153983 A1 Jun. 7, 2018

Related U.S. Application Data

(62) Division of application No. 14/612,111, filed on Feb. 2, 2015, now Pat. No. 9,839,686, which is a division of application No. 13/499,238, filed as application No. PCT/IB2010/002565 on Sep. 30, 2010, now Pat. No. 8,974,799.

(60) Provisional application No. 61/247,518, filed on Sep. 30, 2009.

(51) Int. Cl.
*A61K 47/64* (2017.01)
*A61K 39/085* (2006.01)
*A61K 39/385* (2006.01)
*A61K 39/00* (2006.01)

(52) U.S. Cl.
CPC .......... *A61K 39/385* (2013.01); *A61K 39/085* (2013.01); *A61K 47/646* (2017.08); *A61K 47/6415* (2017.08); *A61K 2039/6037* (2013.01); *A61K 2039/627* (2013.01); *Y10S 424/831* (2013.01); *Y10S 530/807* (2013.01)

(58) Field of Classification Search
None
See application file for complete search history.

(56) References Cited

U.S. PATENT DOCUMENTS

| 3,269,913 A | 8/1966 | Devlin et al. |
| 4,356,170 A | 10/1982 | Jennings et al. |
| 4,446,275 A | 5/1984 | Filka et al. |
| 5,306,492 A | 4/1994 | Porro |
| 6,027,733 A * | 2/2000 | Wang ................. A61K 39/0216 424/234.1 |
| 8,974,799 B2 * | 3/2015 | Berti ................. A61K 39/085 424/243.1 |
| 9,441,004 B2 | 9/2016 | Costantino et al. |
| 9,839,686 B2 | 12/2017 | Berti et al. |
| 2007/0014812 A1 | 1/2007 | Kim et al. |
| 2007/0110762 A1 | 5/2007 | Jessouroun et al. |
| 2010/0322958 A1 | 12/2010 | Bardotti et al. |
| 2012/0276137 A1 * | 11/2012 | Freese .................. A61K 39/085 424/197.11 |

FOREIGN PATENT DOCUMENTS

| JP | 2001519817 A | 10/2001 |
| JP | 2007524621 A | 8/2007 |
| JP | 2009531388 A | 9/2009 |
| WO | 1999029328 A1 | 6/1999 |
| WO | WO 2005/000346 A1 * | 1/2005 |
| WO | 2006067632 A2 | 6/2006 |
| WO | 2007113223 A | 10/2007 |
| WO | 2008084411 A2 | 7/2008 |

OTHER PUBLICATIONS

Berry, et al., "Effect of O Acetylation of Neisseria meningitidis Serogroup A Capsular Polysaccharide on Development of Functional Immune Responses", Infection and Immunity, 2002, 70(7), p. 3707-3713.

Cescutti et al. (1996). "Determination of the size and degree of acetyl substitution of oligosaccharides from Neisseria meningitidis group A by ionspray mass spectrometry," Biochem Biophys Res Comm 224(2):444-450.

Dick et al., Contrib. Microbiol. Immunol. Basel Karger 10:48-114, 1989.

Fattom et al. (1992). "Comparative immunogenicity of conjugates composed of the *Staphylococcus aureus* type 8 capsular polysaccharide bound to carrier proteins by adipic acid dihydrazide or N-succinimidyl-3-(2-pyridyldithio) propionate," Infect Immun 60(2):584-589.

Fattom et al. (1998). "Antigenic determinants of *Staphylococcus aureus* type 5 and type 8 capsular polysaccharide vaccines," Infect Immun, 66(10):4588-92.

Fournier et al. Infect. Immun. 45:87-93, 1984.

International Search Report dated Mar. 3, 2011, for PCT/IB2010/002565, 4 pages.

(Continued)

*Primary Examiner* — Sarvamangala Devi
(74) *Attorney, Agent, or Firm* — Joseph J. Schuller

(57) ABSTRACT

The invention provides a process for preparing a conjugate of a *S. aureus* type 5 or type 8 capsular polysaccharide and a carrier molecule, comprising the steps of: (a) depolymerising the capsular polysaccharide, to give a polysaccharide fragment; (b) oxidising the fragment in order to introduce an aldehyde group into at least one saccharide residue in the fragment, to give an oxidised saccharide residue; and (c) coupling the oxidised saccharide residue to a carrier molecule via the aldehyde group, thereby giving the conjugate. The coupling in step (c) may be direct, or may be via a linker molecule. The invention also provides a conjugate obtained or obtainable by this process.

10 Claims, 22 Drawing Sheets
Specification includes a Sequence Listing.

(56) References Cited

OTHER PUBLICATIONS

Laferriere et al. (1997). "The synthesis of *Streptococcus pneumoniae* polysaccharide-tetanus toxoid conjugates and the effect of chain length on immunogenicity," Vaccine, 15(2):179-86.

Ovodov (2006). "Capsular antigens of bacteria. Capsular antigens as the basis of vaccines against pathogenic bacteria," Biochemistry 71(9):955-961.

Reynaud-Rondier et al., FEMS Microbiology Immunology 76:193-200; 1991.

Thakker et al. (1998). "*Staphylococcus aureus* serotype 5 capsular polysaccharide is antiphagocytic and enhances bacterial virulence in a murine bacteremia model," Infect Immun, 66(11):5183-9.

Wang et al. (1998). "Ozonolysis for selectively depolymerizing polysaccharides containing beta-D-aldosidic linkages," Proc Natl Acad Sci USA, 95(12):6584-9.

* cited by examiner

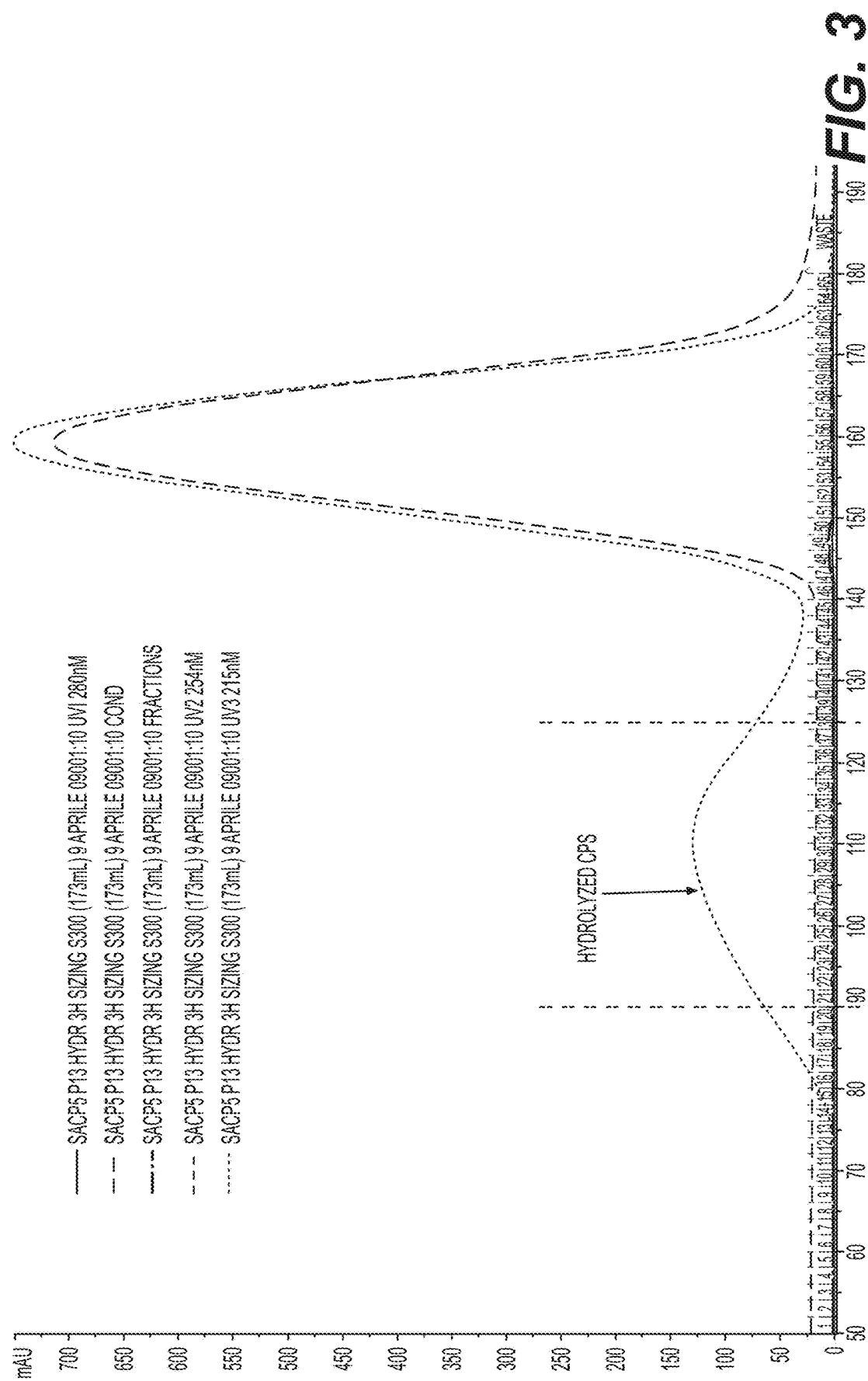

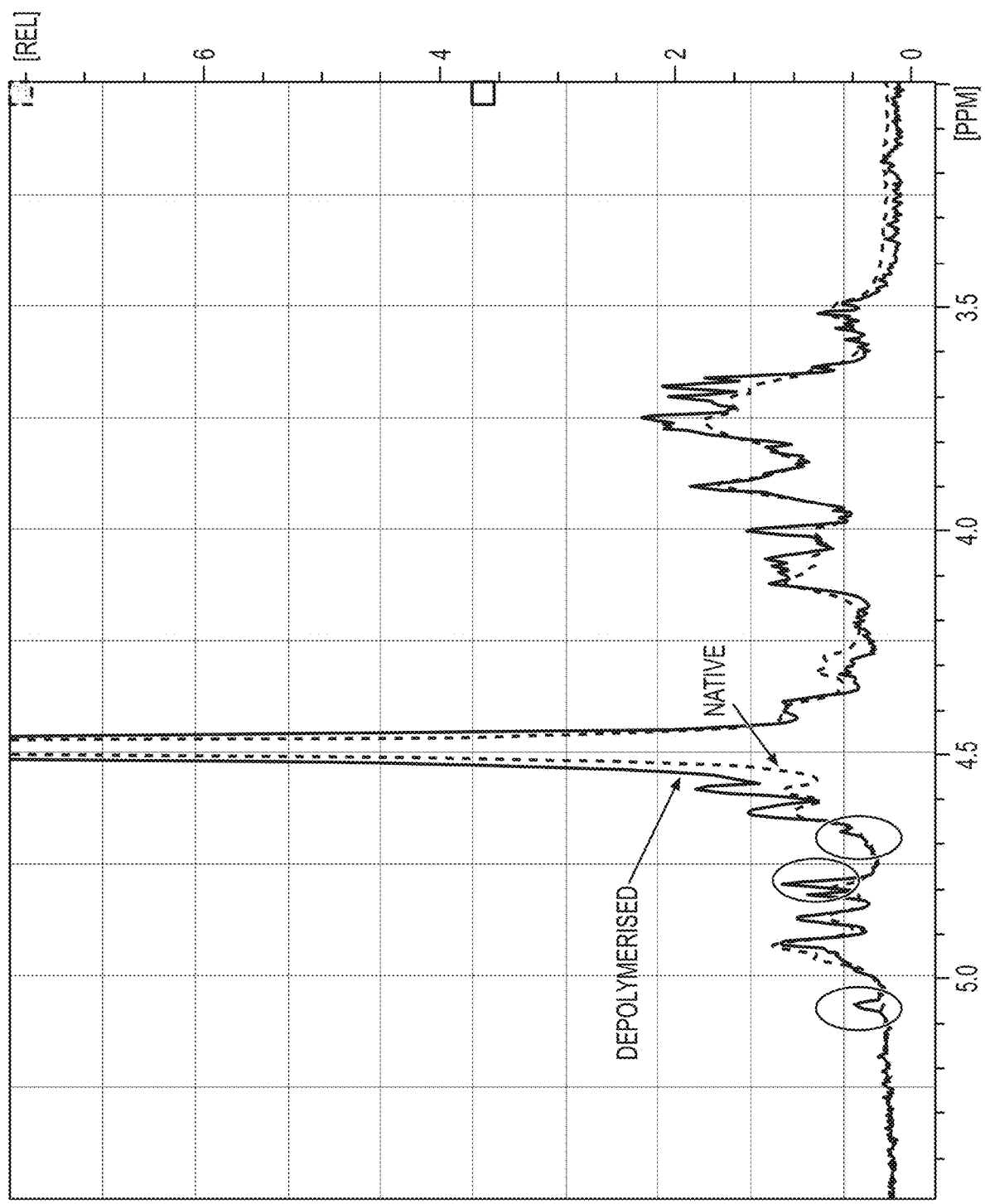

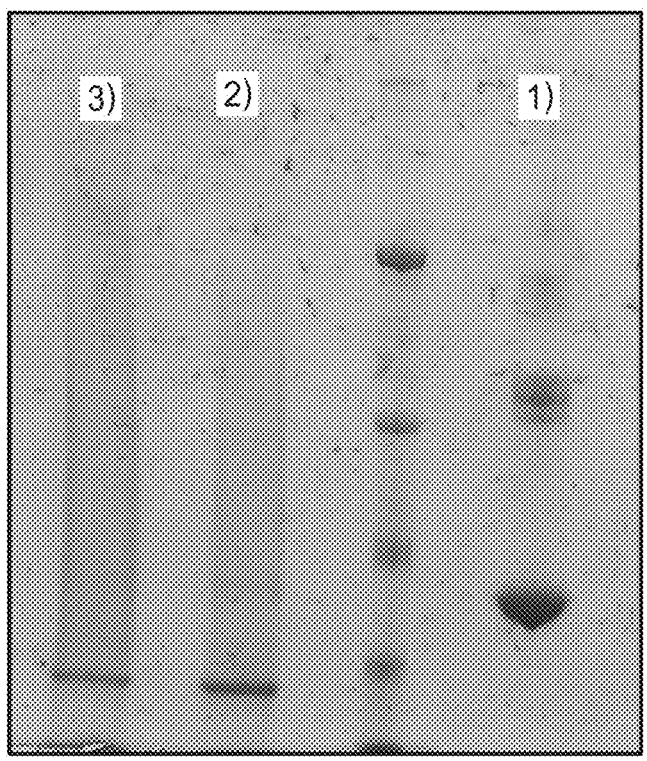
1) CRMadh (5μG)
2) HYDROLYZED 30'-CRMadh CONJUGATE (2.5μG)
3) HYDROLYZED 3H-CRMadh CONJUGATE (2.5μG)
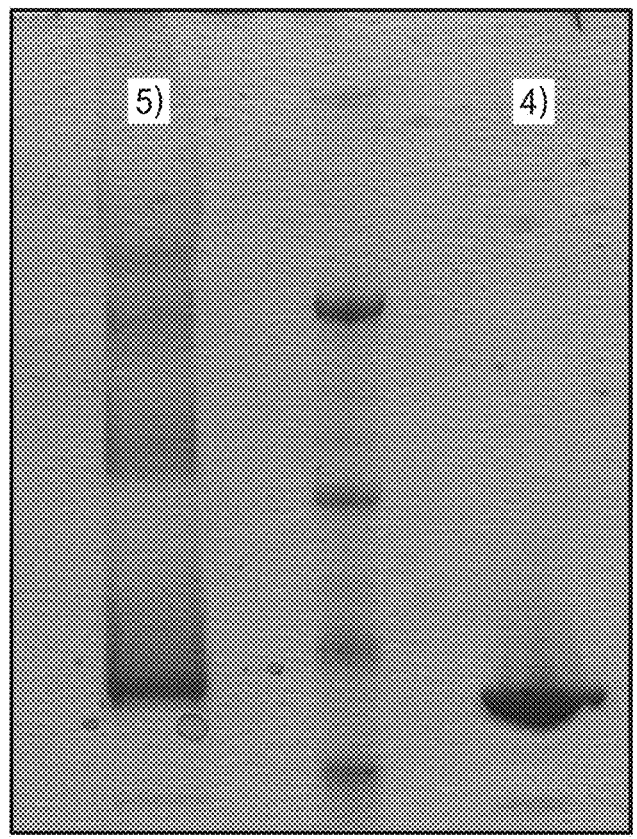
4) CRM (5μG)
5) HYDROLYZED 5H-CRM CONJUGATE (2.5μG)
*FIG. 7*

CONJUGATION OF *STAPHYLOCOCCUS AUREUS* TYPE 5 AND TYPE 8 CAPSULAR POLYSACCHARIDES

CROSS REFERENCE TO RELATED APPLICATIONS

This application is a Divisional of U.S. patent application Ser. No. 14/612,111, filed Feb. 2, 2015 (now U.S. Pat. No. 9,839,686), which is a Divisional of U.S. patent application Ser. No. 13/499,238, filed Jun. 4, 2012 (now U.S. Pat. No. 8,974,799); which is a National Phase of international Patent Application No. PCT/IB2010/002565, filed Sep. 30, 2010; which claims the benefit of U.S. Provisional Patent Application No. 61/247,518, filed Sep. 30, 2009, all of which are incorporated herein by reference in their entirety.

SUBMISSION OF THE SEQUENCE LISTING AS ASCII TEXT FILE

The content of the following submission on ASCII text file is incorporated herein by reference in its entirety: a computer readable form (CRF) of the Sequence Listing (file name: 223002111310SeqList.txt, date recorded: Jan. 27, 2015, size: 153 KB).

TECHNICAL FIELD

This invention is in the field of conjugating bacterial capsular saccharides, particularly *Staphylococcus aureus* type 5 or type 8 capsular polysaccharides, to carriers in order to form glycoconjugates. The glycoconjugates are useful for immunisation.

BACKGROUND ART

The capsular saccharides of bacteria have been used for many years in vaccines against capsulated bacteria. As saccharides are T-independent antigens, however, they are poorly immunogenic. Conjugation to a carrier can convert T-independent antigens into T-dependent antigens, thereby enhancing memory responses and allowing protective immunity to develop. The most effective saccharide vaccines are therefore based on glycoconjugates, and the prototype conjugate vaccine was against *Haemophilus influenzae* type b ('Hib') [e.g. see chapter 14 of ref. 97].

Another bacterium for which conjugate vaccines have been described is *Staphylococcus aureus* (*S. aureus*). Various polysaccharides have been isolated from *S. aureus* for use in glycoconjugates. Two polysaccharides of particular interest are the type 5 and type 8 capsular polysaccharides. Approximately 60% of human *S. aureus* strains are type 8 and approximately 30% are type 5. Much of the work on type 5 and type 8 conjugates has been performed by Fattom et al., and is described in documents such as references 1 to 9. The Fattom process for type 5 and type 8 polysaccharide conjugation typically involves thiolation of a purified polysaccharide using cystamine. The reaction relies on the presence of carboxylate groups in the capsular polysaccharide. These groups react with cystamine in the presence of a carbodiimide, e.g. EDAC. The derivatised polysaccharide is then conjugated to a carrier protein such as the *Pseudomononas aeruginosa* endotoxin A (ETA), typically via a linker [2]. Other researchers have carried out conjugation of purified type 5 and type 8 capsular polysaccharides by reductive amination [10 and 11]; glutaradehyde coupling [10]; or reaction of hydroxyl groups on the polysaccharides with cyanylating agents like CDAP [12] or cyanuric trichloride [13].

Although conjugate vaccines prepared by the Fattom process have been shown to be safe and immunogenic in humans [5], there remains a need for further and better ways of preparing conjugates of *S. aureus* type 5 or type 8 capsular polysaccharides.

DISCLOSURE OF THE INVENTION

The invention is based on a conjugation method that can be used in place of the conjugation methods disclosed in the prior art. Unlike these methods, the method of the invention does not involve conjugation via hydroxyl or carboxylate groups in the polysaccharide. The method therefore leaves these groups in a form that is closer than the prior art to the form seen in the native polysaccharide. Instead of using these groups, the method involves the generation of reactive aldehyde groups in the polysaccharide for use in conjugation. The resultant conjugates may have different, preferably improved, immunological properties compared to the conjugates of the prior art.

The invention therefore provides alternative or improved methods for conjugating *S. aureus* type 5 or type 8 capsular polysaccharide to a carrier protein and conjugates obtained therefrom. The invention also provides intermediates that are useful in the methods of the invention and methods for preparing these intermediates.

In a first aspect, the invention provides a process for preparing a conjugate of a *S. aureus* type 5 or type 8 capsular polysaccharide and a carrier molecule, comprising the steps of: (a) depolymerising the capsular polysaccharide, to give a polysaccharide fragment; (b) oxidising the fragment in order to introduce an aldehyde group into at least one saccharide residue in the fragment, to give an oxidised saccharide residue; and (c) coupling the oxidised saccharide residue to a carrier molecule via the aldehyde group, thereby giving the conjugate. The coupling in step (c) may be direct, or it may be via a linker molecule. The invention also provides a conjugate obtained or obtainable by this process.

The Capsular Polysaccharide

The invention is based on the capsular polysaccharides of *S. aureus* type 5 and type 8. The structures of type 5 and type 8 capsular polysaccharides were described in references 14 and 15 as:

Type 5
→4)-β-D-ManNAcA(3OAc)-(1→4)-α-L-FucNAc
(1→3)-β-D-FucNAc-(1→

Type 8
→3)-β-D-ManNAcA(4OAc)-(1→3)-α-L-FucNAc(1-3)-
β-D-FucNAc-(1→

Recent NMR spectroscopy data [16] has led to a revision of these structures to:

Type 5
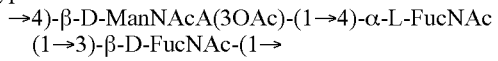
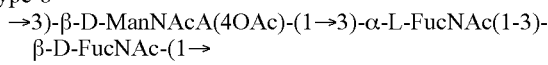

Type 8
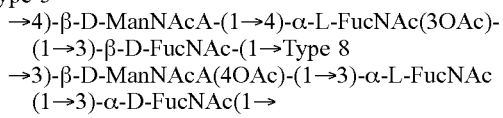

The polysaccharide may be chemically modified relative to the capsular polysaccharide as found in nature.

For example, the polysaccharide may be de-O-acetylated (partially or fully), de-N-acetylated (partially or fully), N-propionated (partially or fully), etc. De-acetylation may occur before, during or after conjugation, but typically occurs before conjugation. Depending on the particular polysaccharide, de-acetylation may or may not affect immunogenicity e.g. the NeisVac-C™ vaccine uses a de-O-acetylated polysaccharide, whereas Menjugate™ is acetylated, but both vaccines are effective. The effect of de-acetylation etc. can be assessed by routine assays. For example, the relevance of O-acetylation on *S. aureus* type 5 or type 8 capsular polysaccharides is discussed in reference 6. The native polysaccharides are said in this document to have 75% O-acetylation. These polysaccharides induced antibodies to both the polysaccharide backbone and O-acetyl groups. Polysaccharides with 0% O-acetylation still elicited antibodies to the polysaccharide backbone. Both types of antibody were opsonic against *S. aureus* strains that varied in their O-acetyl content. Accordingly, the type 5 or type 8 capsular polysaccharides used in the present invention may have between 0 and 100% O-acetylation. For example, the degree of O-acetylation of the type 5 capsular polysaccharide may be 10-100%, 10-100%, 20-100%, 30-100%, 40-100%, 50-100%, 60-100%, 70-100%, 80-100%, 90-100%, 50-90%, 60-90%, 70-90% or 80-90%. Alternatively, 0% O-acetylated type 5 capsular polysaccharide may be used. Similarly, the degree of O-acetylation of the type 8 capsular polysaccharide may be 10-100%, 10-100%, 20-100%, 30-100%, 40-100%, 50-100%, 60-100%, 70-100%, 80-100%, 90-100%, 50-90%, 60-90%, 70-90% or 80-90%. Alternatively, 0% O-acetylated type 8 capsular polysaccharide may be used. In one embodiment, the degree of O-acetylation of the type 5 and type 8 capsular polysaccharides may be 10-100%, 20-100%, 30-100%, 40-100%, 50-100%, 60-100%, 70-100%, 80-100%, 90-100%, 50-90%, 60-90%, 70-90% or 80-90%. In other embodiments, 0% O-acetylated type 5 and type 8 capsular polysaccharides are used. The degree of N-acetylation of the type 5 capsular polysaccharide used in the invention may be 0-100%, 50-100%, 75-100%, 80-100%, 90-100%, or 95-100%. Typically, the degree of N-acetylation of the type 5 capsular polysaccharide is 100%. Similarly, the degree of N-acetylation of the type 8 capsular polysaccharide used in the invention may be 0-100%, 50-100%, 75-100%, 80-100%, 90-100%, or 95-100%. Typically, the degree of N-acetylation of the type 8 capsular polysaccharide is 100%. In one embodiment, the degree of N-acetylation of the type 5 and type 8 capsular polysaccharides may be 0-100%, 50-100%, 75-100%, 80-100%, 90-100%, or 95-100%. Typically, the degree of N-acetylation of the type 5 and type 8 capsular polysaccharide is 100%.

The degree of O-acetylation of the polysaccharide can be determined by any method known in the art, for example, by proton NMR (e.g. as described in references 17, 18, 19 or 20). A further method is described in reference 21. Similar methods may be used to determine the degree of N-acetylation of the polysaccharide. O-acetyl groups may be removed by hydrolysis, for example by treatment with a base such as anhydrous hydrazine [22] or NaOH [6]. Similar methods may be used to remove N-acetyl groups. To maintain high levels of O-acetylation on type 5 and/or 8 capsular polysaccharides, treatments that lead to hydrolysis of the O-acetyl groups are minimised, e.g. treatments at extremes of pH.

Capsular polysaccharides can be purified by known techniques, as described in the references herein. A typical process involves phenol-ethanol inactivation of *S. aureus* cells, centrifugation, lysostaphin treatment, RNase/DNase treatment, centrifugation, dialysis, protease treatment, further dialysis, filtration, precipitation with ethanol/CaCl$_2$), dialysis, freeze-drying, anion exchange chromatography, dialysis, freeze-drying, size exclusion chromatography, dialysis and freeze-drying [1]. An alternative process involves autoclaving *S. aureus* cells, ultrafiltration of the polysaccharide-containing supernatant, concentration, lyophilisation, treatment with sodium metaperiodate to remove teichoic acid, further ultrafiltration, diafiltration, high performance size exclusion liquid chromatography, dialysis and freeze-drying [23]. Preferably, the purification process described in reference 24 is used.

The invention is not limited to polysaccharides purified from natural sources, however, and the polysaccharides may be obtained by other methods, such as total or partial synthesis.

The Carrier Molecule

The invention involves the use of carrier molecules, which are typically proteins. In general, covalent conjugation of saccharides to carriers enhances the immunogenicity of saccharides as it converts them from T-independent antigens to T-dependent antigens, thus allowing priming for immunological memory. Conjugation is particularly useful for paediatric vaccines [e.g. ref. 25] and is a well known technique [e.g. reviewed in refs. 26 to 34].

Preferred carrier proteins are bacterial toxins, such as diphtheria or tetanus toxins, or toxoids or mutants thereof. The inventors have found that the CRM197 diphtheria toxin mutant [35] is suitable. *Pseudomonas aeruginosa* exotoxin A (ETA) and its non-toxic mutant recombinant exoprotein A (rEPA) have been used as carrier proteins for *S. aureus* type 5 or type 8 capsular polysaccharides ([1] and [2]). *S. aureus* α-haemolysin (α-toxin) ([10] and [36]), ovalbumin [13] and human serum albumin [11] have also been used. These carriers may be used in the present invention.

Other suitable carrier proteins include the *N. meningitidis* outer membrane protein complex [37], synthetic peptides [38,39], heat shock proteins [40,41], pertussis proteins [42, 43], cytokines [44], lymphokines [44], hormones [44], growth factors [44], human serum albumin (typically recombinant), artificial proteins comprising multiple human CD4$^+$ T cell epitopes from various pathogen-derived antigens [45] such as N19 [46], protein D from *H. influenzae* [47-49], pneumococcal surface protein PspA [50], pneumolysin [51] or its non-toxic derivatives [52], iron-uptake proteins [53], toxin A or B from *C. difficile* [54], a GBS protein [55], a GAS protein [56] etc.

Other suitable carrier proteins include *S. aureus* protein antigens, for example the *S. aureus* protein antigens set out below.

It is possible to use more than one carrier protein e.g. to reduce the risk of carrier suppression. Thus different carrier proteins can be used for the type 5 and type 8 capsular polysaccharides, e.g. type 5 polysaccharide might be conjugated to CRM197 while type 8 polysaccharide might be conjugated to rEPA. It is also possible to use more than one carrier protein for a particular polysaccharide antigen e.g. type 5 polysaccharide might be in two groups, with one group conjugated to CRM197 and the other conjugated to rEPA. Typically, however, the same carrier protein is used for all polysaccharides.

A single carrier protein might carry more than one polysaccharide antigen [57,58]. For example, a single carrier protein might have conjugated to it type 5 and type 8 capsular polysaccharides. To achieve this goal, different polysaccharides can be mixed prior to the conjugation process. Typically, however, there are separate conjugates for each polysaccharide, with the different polysaccharides being mixed after conjugation. The separate conjugates may be based on the same carrier.

Depolymerisation

In step (a) of the process of the invention, the capsular polysaccharide is depolymerised to give a polysaccharide fragment. Depolymerisation of the type 8 capsular polysaccharide by sonication prior to conjugation has been reported [3]. The authors concluded that low molecular weight type 8 was not immunogenic. Although these authors therefore favoured high molecular weight polysaccharides, the present invention surprisingly makes use of polysaccharide fragments with a lower molecular weight than native capsular polysaccharides.

Full-length polysaccharides may be depolymerised to give shorter fragments for use in the invention by various methods. The inventors have found that methods that result in cleavage of (1→3) glycosidic linkages between the α-L-FucNAc(3OAc) and β-D-FucNAc residues in the type 5 capsular polysaccharide are particularly suitable. When these methods are applied to the type 5 capsular polysaccharide, they result in a polysaccharide fragment having a β-D-FucNAc-(1→moiety at its non-reducing terminus. This moiety includes two vicinal hydroxyl groups. Similarly, when these methods are applied to the type 8 capsular polysaccharide, they are thought to result in a polysaccharide fragment having an α-D-FucNAc-(1→moiety at is non-reducing terminus, which moiety also includes two vicinal hydroxyl groups. The vicinal hydroxyl groups in the type 5 or type 8 polysaccharide fragment provide a handle for subsequent conjugation of the fragment to a carrier molecule, as described below.

Accordingly, in a further aspect the invention provides a process for treating a S. aureus type 5 capsular polysaccharide comprising the step of depolymerising the capsular polysaccharide, to give a polysaccharide fragment having a β-D-FucNAc-(1→moiety at its non-reducing terminus. In a related aspect, the invention provides a process for treating a S. aureus type 8 capsular polysaccharide comprising the step of depolymerising the capsular polysaccharide, to give a polysaccharide fragment having an α-D-FucNAc-(1→moiety at its non-reducing terminus. The capsular polysaccharide may be a S. aureus type 5 or type 8 capsular polysaccharide as described in "The capsular polysaccharide" above. The invention also provides a polysaccharide fragment obtained or obtainable by either of these processes.

The inventors have found that the depolymerisation may be carried out by acid hydrolysis. For acid hydrolysis, it is preferred to use a mild acid, e.g. acetic acid, to avoid side-reactions at other groups within the polysaccharide. The skilled person would be capable of identifying suitable acids and conditions (e.g. of concentration, temperature and/or time) for hydrolysis. For example, the inventors have found that treatment of polysaccharide at 2 mg/ml with 2% acetic acid (v/v) at 90° C. for 3 hours is suitable. The inventors have also found that treatment at 2 mg/ml with 5% acetic acid at 90° C. for 30 minutes, 5 or 6 hours is suitable. Treatment with other acids, e.g. trifluoroacetic or other organic acids, may also be suitable. In particular, the inventors have found that depolymerisation efficiency may be increased, particularly for type 8 capsular polysaccharide, by using hydrochloric acid. For example, the inventors have found that treatment of polysaccharide with 2M hydrochloric acid at 100° C. for 30 minutes is suitable. The inventors have also found that treatment with 2M hydrochloric acid at 100° C. for 1, 1.5, 2 or 2.5 hours is suitable. Such treatment with hydrochloric acid may result in de-O-acetylation of the polysaccharide, e.g. as described below.

Other methods for depolymerisation of the polysaccharide may be suitable. These methods include heating, microfluidisation [59], sonic radiation [3], oxidation-reduction [60] or ozonolysis [61].

Polysaccharide fragments can be identified by chromatography, e.g. size exclusion chromatography. Specific molecular masses can be measured by gel filtration relative to pullulan standards, such as those available from Polymer Standard Service [62]. Typically, the fragment of the invention is a mixture of fragments with masses within a range of values. For the depolymerised type 5 capsular polysaccharide, the molecular mass of the fragment typically varies between 1-500 kDa, e.g. between 5 and 100 kDa, particularly between 10 and 50 kDa and more particularly between 20 and 30 kDa. Similarly, for the depolymerised type 8 capsular polysaccharide, the molecular mass of the fragment may vary between 1-500 kDa, e.g. between 5 and 100 kDa, particularly between 10 and 50 kDa and more particularly between 20 and 30 kDa. In some embodiments, low molecular weight type 5 and/or type 8 polysaccharide fragments are selected for use in the invention. For example, gel filtration fractions corresponding to low molecular weight fragments may be selected and pooled. The low molecular weight polysaccharide fragments typically have a molecular mass that varies between 5 and 20 kDa.

The depolymerisation may result in a change to the degree of O-acetylation of the capsular polysaccharide. For the example, the inventors have found that acid hydrolysis may result in a decrease in the degree of O-acetylation. In some embodiments, the degree of O-acetylation of the fragment may be 10-90%, 20-70%, 30-50%, particularly 35-45%. In other embodiments, the degree of O-acetylation of the fragment may be 0-10%, 0-5%, 0-2%, particularly 0%.

Introduction of an Aldehyde Group

In step (b) of the process, the fragment is oxidised in order to introduce an aldehyde group into at least one saccharide residue in the fragment. This step may involve the introduction of more than one aldehyde group into the saccharide residue. In particular, two aldehyde groups may be introduced. For example, when the depolymerisation in step (a) results in a type 5 polysaccharide fragment having a β-D-FucNAc-(1→moiety at its non-reducing terminus, the two vicinal hydroxyl groups in this moiety may be oxidised in order to introduce two aldehyde groups into the moiety. In this way, the β-D-FucNAc-(1→moiety may be the saccharide residue of step (b). Similarly, when the depolymerisation results in a type 8 polysaccharide fragment having an α-D-FucNAc-(1→moiety at is non-reducing terminus, the two vicinal hydroxyl groups in this moiety may be oxidised to introduce two aldehyde groups. In this way, the α-D-FucNAc-(1→moiety may be the saccharide residue of step (b).

Accordingly, in a further aspect the invention provides a process for providing a S. aureus type 5 capsular polysaccharide derivative comprising the step of oxidising a S. aureus type 5 capsular polysaccharide having a β-D-FucNAc-(1→moiety at its non-reducing terminus to convert two vicinal hydroxyl groups in the β-D-FucNAc-(1→moiety into two aldehyde groups. In a related aspect, the invention provides a process for providing a S. aureus type 8 capsular polysaccharide derivative comprising the step of oxidising a S. aureus type 8 capsular polysaccharide having an α-D-FucNAc-(1→moiety at is non-reducing terminus to convert two vicinal hydroxyl groups in the α-D-FucNAc-(1→moiety into two aldehyde groups. The capsular polysaccharide may be a polysaccharide fragment as described in "Depolymerisation" above. The invention also provides a S. aureus capsular polysaccharide derivative obtained or obtainable by either of these processes.

Typical reactions to produce aldehydes include the use of periodate salts, and particularly meta-periodates (e.g. sodium or potassium meta-periodate e.g. NaIO$_4$), to oxidise vicinal hydroxyl groups [63]. The skilled person would be capable of identifying suitable conditions for oxidation. For example, the inventors have found that treatment of polysaccharide at 2 mg/ml with NaIO$_4$ at a 1:1 ratio (w/w) at room temperature for 1-2 hours in the dark is suitable. The inventors have also found that treatment of polysaccharide at 2 mg/ml with 93 mM NaIO$_4$ at room temperature for 8 hours in the dark is suitable. Other oxidation conditions can be used, e.g. use of osmium tetroxide, etc.

Coupling to a Carrier Molecule

The coupling of the oxidised saccharide residue to the carrier molecule in step (c) of the process may be direct or via a linker. Any suitable conjugation reaction can be used, with any suitable linker if desired.

When the oxidation in step (b) results in a type 5 polysaccharide fragment having a β-D-FucNAc-(1→moiety at its non-reducing terminus in which two aldehyde groups have been introduced into the moiety, the coupling in step (c) may be via one of these aldehyde groups. In this way, the oxidised β-D-FucNAc-(1→moiety may be the oxidised saccharide residue of step (c). Similarly, when the oxidation results in a type 8 polysaccharide fragment having an α-D-FucNAc-(1→moiety at is non-reducing terminus in which two aldehyde groups have been introduced into the moiety, the coupling in step (c) may be via one of these aldehyde groups. In this way, the oxidised α-D-FucNAc-(1→moiety may be the oxidised saccharide residue of step (c).

Accordingly, in a further aspect the invention provides a process for providing a conjugated S. aureus type 5 capsular polysaccharide comprising the step of coupling to a carrier molecule a S. aureus type 5 capsular polysaccharide having a β-D-FucNAc-(1→moiety at its non-reducing terminus that has been oxidised to convert two vicinal hydroxyl groups into two aldehyde groups, wherein the coupling is via one of the aldehyde groups. In a related aspect, the invention provides a process for providing a conjugated S. aureus type 8 capsular polysaccharide comprising the step of coupling to a carrier molecule a S. aureus type 8 capsular polysaccharide having an α-D-FucNAc-(1→moiety at is non-reducing terminus that has been oxidised to convert two vicinal hydroxyl groups into two aldehyde groups, wherein the coupling is via one of the aldehyde groups. The capsular polysaccharide may be a capsular polysaccharide as described in "Introduction of an aldehyde group" above. The carrier molecule may be a carrier as described in "The carrier molecule" above. The invention also provides a conjugated capsular polysaccharide obtained or obtainable by either of these processes.

Attachment of the oxidised saccharide residue or linker to the carrier is typically via an amine (—NH$_2$) group e.g. in the side chain of a lysine or residue in a carrier protein, or of an arginine residue. Attachment to the carrier may also be via a sulphydryl (—SH) group e.g. in the side chain of a cysteine residue. The inventors have found that direct coupling may be conveniently achieved by reacting an aldehyde group in the oxidised saccharide residue with an amine group in the carrier by reductive amination. Direct coupling of this nature is therefore preferred in the present invention. In contrast, reference 2 suggests that linkers may be advantageous in S. aureus type 5 and 8 conjugates. If desired, coupling via a linker may be used in the present invention, e.g. by reacting an aldehyde group in the oxidised saccharide residue with an amine group in the linker by reductive amination, or by converting the aldehyde group into an amine group by reductive amination to provide an amine group for attachment of the linker.

Reductive amination is a standard technique in organic chemistry, and has been used extensively in the production of conjugates of capsular polysaccharides for vaccine use, including S. aureus capsular polysaccharides [10]. In one embodiment, an aldehyde group in the oxidised saccharide residue reacts with an amine group in the carrier or linker. This can conveniently be achieved by combining the polysaccharide with the carrier or linker in the presence of an appropriate reducing agent (e.g. cyanoborohydrides, such as sodium cyanoborohydride NaBH$_3$CN; borane-pyridine; sodium triacetoxyborohydride; borohydride exchange resin; etc.). In another embodiment, an aldehyde group is converted into an amine group by reductive amination to provide an amine group for attachment of the linker. The reductive amination involves either ammonia or a primary amine (NH$_2$R). This can conveniently be achieved by using an ammonium salt (e.g. ammonium chloride) in combination with an appropriate reducing agent (e.g. as listed above). The skilled person would be capable of identifying suitable conditions for reductive amination. For example, the inventors have found that treatment of polysaccharide at 10 mg/ml with carrier protein at a 4:1 polysaccharide:protein ratio (w/w) and NaBH$_3$CN at a 2:1 polysaccharide:NaBH$_3$CN ratio is suitable.

Coupling via a linker group may be made using any known procedure, e.g. the reductive amination procedures described above. In one embodiment, a bifunctional linker may be used to provide a first group for coupling to the aldehyde group in the oxidised saccharide residue and a second group for coupling to the carrier. For example, a bifunctional linker of the formula X$_1$-L-X$_2$ may be used, where X$_1$ can react with the aldehyde; X$_2$ can react with the carrier; and L is a linking moiety in the linker. A typical X$_1$ group is an amine group. Typical L groups are straight chain alkyls with 1 to 10 carbon atoms (e.g. C$_1$, C$_2$, C$_3$, C$_4$, C$_5$, C$_6$, C$_7$, C$_8$, C$_9$, C$_{10}$) e.g. —(CH$_2$)$_4$— or —(CH$_2$)$_3$—. In another embodiment, a bifunctional linker may be used to provide a first group for coupling to an amine group derived from the aldehyde group in the oxidised saccharide residue (e.g. by reductive amination as described above) and a second group for coupling to the carrier (typically for coupling to an amine in the carrier). For example, a homobifunctional linker of the formula X-L-X may be used, where the two X groups are the same as each other and can react with the amines; and where L is a linking moiety in the linker. A typical X group is N-oxysuccinimide. L typically has formula -L'-L$^2$-L'-, where L' is carbonyl. Typical L$^2$ groups are straight chain alkyls with 1 to 10 carbon atoms (e.g. C$_1$, C$_2$, C$_3$, C$_4$, C$_5$, C$_6$, C$_7$, C$_8$, C$_9$, C$_{10}$) e.g. —(CH$_2$)$_4$—. A typical linker is thus adipic acid N-hydroxysuccinimide diester (SIDEA):

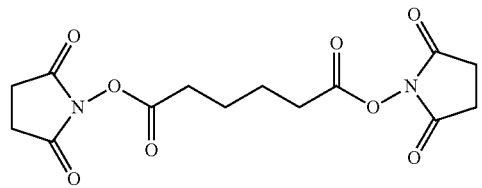 [SMILES: O=C(CCCCC(=O)ON1C(=O)CCC1=O)ON1C(=O)CCC1=O]

Other X groups are those which form esters when combined with HO-L-OH, such as norborane, p-nitrobenzoic acid, and sulfo-N-hydroxysuccinimide. Further bifunctional linkers reactive with amines for use with the invention include acryloyl halides (e.g. chloride) [65], haloacylhalides [66], disuccinimidyl glutarate, disuccinimidyl suberate, ethylene glycol bis[succinimidylsuccinate], etc.

The linker will generally be added in molar excess to the polysaccharide. The linker/polysaccharide reaction will generally take place in an aprotic solvent (e.g. DMSO, ethanol acetate, etc.), as the linkers are typically insoluble in water. Where water-soluble linkers are used, however, then a wider range of solvents is available, including protic solvents such as water. Suitable linkers include sulphonated forms, such as sulphonated SIDEA:

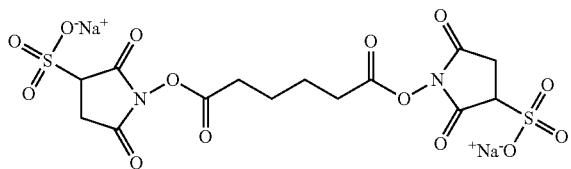

When a linker is used, the conjugate will comprise a linker moiety. This moiety originates neither in the polysaccharide nor the carrier, but is a third molecule used during conjugate preparation, and can readily be distinguished from both the polysaccharide and carrier protein in a final conjugate product. The linker moiety may include atoms such as carbon, hydrogen, oxygen and/or nitrogen. Linkers that comprise carbon and hydrogen are typical, and linkers that further comprise oxygen and/or nitrogen are also typically used. Linkers that include nitrogen atoms may include a carbon atom bonded to a nitrogen atom, which in turn is bonded to a second carbon atom (—C—N—C—). Linkers that include an oxygen atom typically include it as part of a carbonyl group. Linker moieties with a molecular weight of between 30-500 Da are typical. Linkers containing two carbonyl groups are also typical.

A particularly useful linker moiety is —NH—C(O)—(CH$_2$)$_n$—C(O)—, wherein n is 1, 2, 3, 4, 5, 6, 7, 8, 9 or 10. The value of n is typically 4. The terminal —NH— in this linker is usually attached to a carbon atom from the polysaccharide moiety. The terminal —C(O)— is usually attached to a nitrogen atom in an amino acid side chain in the carrier. A preferred linker moiety can conveniently be introduced by a process involving: reductive amination of the aldehyde in the oxidised saccharide residue; reaction of the resulting —NH$_2$ group with a bifunctional linker that is a diester (e.g. a disuccinimidyl ester) of a dioic acid (e.g. of adipic acid, HOOC—(CH$_2$)$_4$—COOH); and reductive amination of the product (see FIG. 6).

Other chemistries that can be used to attach a linker to a —NH$_2$ group in the polysaccharide, include:
  acryloylation (e.g. by reaction with acryloyl chloride), followed by Michael-type addition to either the ε-NH$_2$ of an amino acid side chain or to a —SH of a cysteine side chain [65]. The resulting linker is —NH—C(O)—(CH$_2$)$_2$— (propionamido).
  reaction with a haloacylhalide, followed by reaction with the ε-NH$_2$ of an amino acid side chain or to a —SH of a cysteine side chain [66]. The linker is —NH—C(O)—CH$_2$—.

Conjugates with a polysaccharide:protein ratio (w/w) of between 1:20 (i.e. excess protein) and 20:1 (i.e. excess polysaccharide) are typically produced by the method of the invention. Ratios of 1:10 to 1:1 are preferred, particularly ratios between 1:5 and 1:2 and, most preferably, about 1:3. In contrast, type 5 and type 8 capsular polysaccharide conjugates made by processes of the prior art tend to have higher ratios, e.g. between 0.73:1 and 1.08:1 in references 1, 2 and 3. In particular embodiments of the invention, the polysaccharide:protein ratio (w/w) for type 5 capsular polysaccharide conjugate is between 1:10 and 1:2; and/or the polysaccharide:protein ratio (w/w) for type 8 capsular polysaccharide conjugate is between 1:5 and 7:10.

Compositions may include a small amount of free carrier [67]. When a given carrier protein is present in both free and conjugated form in a composition of the invention, the unconjugated form is preferably no more than 5% of the total amount of the carrier protein in the composition as a whole, and more preferably present at less than 2% by weight.

After conjugation, free and conjugated polysaccharides can be separated. There are many suitable methods, including hydrophobic chromatography, tangential ultrafiltration, diafiltration etc. [see also refs. 68 & 69, etc.].

Combinations of Conjugates and Other Antigens

As well as providing individual conjugates as described above, the invention provides a composition comprising a conjugate of the invention and one or more further antigens. The composition is typically an immunogenic composition.

The further antigen(s) may comprise further conjugates of the invention, and so the invention provides a composition comprising more than one conjugate of the invention. In particular, the present invention provides a composition comprising a type 5 capsular polysaccharide conjugate of the invention and a type 8 capsular polysaccharide conjugate of the invention. Alternatively, the further antigen(s) may be type 5 or type 8 capsular polysaccharide conjugates prepared by methods other than those of the invention, e.g. the methods of references 1 to 13 above. The further antigen(s) may similarly be type 5 or type 8 capsular polysaccharide conjugates prepared by the methods of references 59, 70, 71, 72, 73, and 74, and particularly the exemplified methods in those documents. Accordingly, the invention provides a composition comprising a type 5 capsular polysaccharide conjugate and a type 8 capsular polysaccharide conjugate, wherein one of the conjugates (the type 5 conjugate or the type 8 conjugate) is a conjugate of the invention and the other conjugate is not a conjugate of the invention.

The further antigen(s) may comprise other S. aureus antigens, including protein and saccharide antigens, as set out below.

The further antigen(s) may comprise antigens from non-S. aureus pathogens. Thus the compositions of the invention may further comprise one or more non-S. aureus antigens, including additional bacterial, viral or parasitic antigens. These may be selected from the following:
  a protein antigen from N. meningitidis serogroup B, such as those in refs. 75 to 81, with protein '287' (see below) and derivatives (e.g. 'ΔG287') being particularly useful.
  an outer-membrane vesicle (OMV) preparation from N. meningitidis serogroup B, such as those disclosed in refs. 82, 83, 84, 85 etc.
  a saccharide antigen from N. meningitidis serogroup A, C, W135 and/or Y, such as the oligosaccharide disclosed in ref. 86 from serogroup C or the oligosaccharides of ref. 87.
  a saccharide antigen from Streptococcus pneumoniae [e.g. refs. 88-90; chapters 22 & 23 of ref. 97].

an antigen from hepatitis A virus, such as inactivated virus [e.g. 91, 92; chapter 15 of ref. 97].

an antigen from hepatitis B virus, such as the surface and/or core antigens [e.g. 92,93; chpater 16 of ref. 97].

an antigen from hepatitis C virus [e.g. 94].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 95 & 96; chapter 21 of ref. 97].

a diphtheria antigen, such as a diphtheria toxoid [e.g. chapter 13 of ref. 97].

a tetanus antigen, such as a tetanus toxoid [e.g. chapter 27 of ref. 97].

a saccharide antigen from *Haemophilus influenzae* B [e.g. chapter 14 of ref. 97]

an antigen from *N. gonorrhoeae* [e.g. 75, 76, 77].

an antigen from *Chlamydia pneumoniae* [e.g. 98, 99, 100, 101, 102, 103, 104].

an antigen from *Chlamydia trachomatis* [e.g. 105].

an antigen from *Porphyromonas gingivalis* [e.g. 106].

polio antigen(s) [e.g. 107, 108; chapter 24 of ref. 97] such as IPV.

rabies antigen(s) [e.g. 109] such as lyophilised inactivated virus [e.g. 110, RabAvert™].

measles, mumps and/or rubella antigens [e.g. chapters 19, 20 and 26 of ref. 97].

influenza antigen(s) [e.g. chapters 17 & 18 of ref. 97], such as the haemagglutinin and/or neuraminidase surface proteins.

an antigen from *Moraxella catarrhalis* [e.g. 111].

an antigen from *Streptococcus pyogenes* (group A streptococcus) [e.g. 112, 113, 114].

an antigen from *Streptococcus agalactiae* (group B streptococcus) [e.g. 56, 115-117].

an antigen from *S. epidermidis* [e.g. type I, II and/or III capsular polysaccharide obtainable from strains ATCC-31432, SE-360 and SE-10 as described in refs. 118, 119 and 120.

Where a saccharide or carbohydrate antigen is used, it is typically conjugated to a carrier in order to enhance immunogenicity. Conjugation of *H. influenzae* B, meningococcal and pneumococcal saccharide antigens is well known.

Toxic protein antigens may be detoxified where necessary (e.g. detoxification of pertussis toxin by chemical and/or genetic means [96]).

Where a diphtheria antigen is included in the composition it is typical also to include tetanus antigen and pertussis antigens. Similarly, where a tetanus antigen is included it is typical also to include diphtheria and pertussis antigens. Similarly, where a pertussis antigen is included it is typical also to include diphtheria and tetanus antigens.

Antigens may be adsorbed to an aluminium salt.

One type of preferred composition includes further antigens that affect the immunocompromised, and so the *S. aureus* conjugates of the invention can be combined with one or more antigens from the following non-*S. aureus* pathogens: *Steptococcus agalactiae, Staphylococcus epidermis,* influenza virus, *Enterococcus faecalis, Pseudomonas aeruginosa, Legionella pneumophila, Listeria monocytogenes, Neisseria meningitidis*, and parainfluenza virus.

Another type of preferred composition includes further antigens from bacteria associated with nosocomial infections, and so the *S. aureus* conjugates of the invention can be combined with one or more antigens from the following non-*S. aureus* pathogens: *Clostridium difficile; Pseudomonas aeruginosa; Candida albicans*; and extraintestinal pathogenic *Escherichia coli.*

Antigens in the composition will typically be present at a concentration of at least 1 µg/ml each. In general, the concentration of any given antigen will be sufficient to elicit an immune response against that antigen.

As an alternative to using proteins antigens in the composition of the invention, nucleic acid encoding the antigen may be used [e.g. refs. 121 to 129]. Protein components of the compositions of the invention may thus be replaced by nucleic acid (usually DNA e.g. in the form of a plasmid) that encodes the protein.

In practical terms, there may be an upper limit to the number of antigens included in compositions of the invention. The number of antigens (including *S. aureus* antigens) in a composition of the invention may be less than 20, less than 19, less than 18, less than 17, less than 16, less than 15, less than 14, less than 13, less than 12, less than 11, less than 10, less than 9, less than 8, less than 7, less than 6, less than 5, less than 4, or less than 3. The number of *S. aureus* antigens in a composition of the invention may be less than 6, less than 5, or less than 4.

Pharmaceutical Compositions and Methods

The invention provides a pharmaceutical composition comprising (a) a conjugate of the invention and (b) a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [130], trehalose [131], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 132.

Compositions of the invention may be in aqueous form (i.e. solutions or suspensions) or in a dried form (e.g. lyophilised). If a dried vaccine is used then it will be reconstituted into a liquid medium prior to injection. Lyophilisation of conjugate vaccines is known in the art e.g. the Menjugate™ product is presented in lyophilised form, whereas NeisVac-C™ and Meningitec™ are presented in aqueous form. To stabilise conjugates during lyophilisation, it may be typical to include a sugar alcohol (e.g. mannitol) or a disaccharide (e.g. sucrose or trehalose) e.g. at between 1 mg/ml and 30 mg/ml (e.g. about 25 mg/ml) in the composition.

Compositions may be presented in vials, or they may be presented in ready-filled syringes. The syringes may be supplied with or without needles. A syringe will include a single dose of the composition, whereas a vial may include a single dose or multiple doses.

Aqueous compositions of the invention are also suitable for reconstituting other vaccines from a lyophilised form. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Compositions of the invention may be packaged in unit dose form or in multiple dose form. For multiple dose forms, vials are preferred to pre-filled syringes. Effective dosage volumes can be routinely established, but a typical human dose of the composition has a volume of 0.5 ml e.g. for intramuscular injection.

The pH of the composition is typically between 6 and 8, e.g. about 7. Stable pH may be maintained by the use of a buffer. If a composition comprises an aluminium hydroxide salt, it is typical to use a histidine buffer [133]. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Within each dose, the quantity of an individual saccharide antigen will generally be between 1-50 µg (measured as mass of saccharide) e.g. about 1 µg, about 2.5 µg, about 4 µg, about 5 µg, or about 10 µg.

*S. aureus* affects various areas of the body and so the compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 134 & 135]. Success with nasal administration of pneumococcal saccharides [136,137], Hib saccharides [138], MenC saccharides [139], and mixtures of Hib and MenC saccharide conjugates [140] has been reported.

Compositions of the invention may include an antimicrobial, particularly when packaged in multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention will generally be administered in conjunction with other immunoregulatory agents. In particular, compositions will usually include one or more adjuvants. Such adjuvants include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 141], or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being typical. The mineral containing compositions may also be formulated as a particle of metal salt [142].

Aluminum salts may be included in vaccines of the invention such that the dose of $Al^{3+}$ is between 0.2 and 1.0 mg per dose.

A typical aluminium phosphate adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 g $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

B. Oil Emulsions

Oil emulsion compositions suitable for use as adjuvants in the invention include squalene-water emulsions, such as MF59 (5% Squalene, 0.5% Tween 80, and 0.5% Span 85, formulated into submicron particles using a microfluidizer) [Chapter 10 of ref. 141; see also refs. 143-145]. MF59 is used as the adjuvant in the FLUAD™ influenza virus trivalent subunit vaccine.

Particularly useful adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80 (polyoxyelthylenesorbitan monooleate), and/or 0.25-1.0% Span 85 (sorbitan trioleate), and, optionally, N-acetylmuramyl-L-alanyl-D-isogluatminyl-L-alanine-2-(1'-2'-dipalmitoyl-sn-glycero-3-hydroxyphosphophoryloxy)-ethylamine (MTP-PE). Submicron oil-in-water emulsions, methods of making the same and immunostimulating agents, such as muramyl peptides, for use in the compositions, are described in detail in references 143 & 146-147.

Complete Freund's adjuvant (CFA) and incomplete Freund's adjuvant (IFA) may also be used as adjuvants in the invention.

C. Saponin formulations [chapter 22 of ref 141]

Saponin formulations may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 148. Saponin formulations may also comprise a sterol, such as cholesterol [149].

Combinations of saponins and cholesterols can be used to form unique particles called immunostimulating complexes (ISCOMs) [chapter 23 of ref. 141]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 149-151. Optionally, the ISCOMS may be devoid of additional detergent(s) [152].

A review of the development of saponin based adjuvants can be found in refs. 153 & 154.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 155-160. Virosomes are discussed further in, for example, ref. 161

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 162. Such "small particles" of 3dMPL are small enough to be sterile filtered through a 0.22 m membrane [162]. Other non-toxic LPS derivatives include monophosphoryl lipid A mimics, such as aminoalkyl glucosaminide phosphate derivatives e.g. RC-529 [163,164].

Lipid A derivatives include derivatives of lipid A from *Escherichia coli* such as OM-174. OM-174 is described for example in refs. 165 & 166.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 167, 168 and 169 disclose possible analog substitutions e.g. replacement of guanosine with 2'-deoxy-7-deazaguanosine. The adjuvant effect of CpG oligonucleotides is further discussed in refs. 170-175.

The CpG sequence may be directed to TLR9, such as the motif GTCGTT or TTCGTT [176]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 177-179. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 176 & 180-182.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 183 and as parenteral adjuvants in ref. 184. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivaties thereof, particularly LT-K63 and LT-R72, as adjuvants can be found in refs. 185-192. Numerical reference for amino acid substitutions is preferably based on the alignments of the A and B subunits of ADP-ribosylating toxins set forth in ref. 193, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [194], etc.) [195], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [196] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [197].

H. Microparticles

Microparticles may also be used as adjuvants in the invention. Microparticles (i.e. a particle of ~100 nm to ~150 m in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of ref 141)

Examples of liposome formulations suitable for use as adjuvants are described in refs. 198-200.

J. Polyoxyethylene Ether and Polyoxyethylene Ester Formulations

Adjuvants suitable for use in the invention include polyoxyethylene ethers and polyoxyethylene esters [201]. Such formulations further include polyoxyethylene sorbitan ester surfactants in combination with an octoxynol [202] as well as polyoxyethylene alkyl ethers or ester surfactants in combination with at least one additional non-ionic surfactant such as an octoxynol [203]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 204 and 205.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 206 and 207.

N. Thiosemicarbazone Compounds.

Examples of thiosemicarbazone compounds, as well as methods of formulating, manufacturing, and screening for compounds all suitable for use as adjuvants in the invention include those described in ref. 208. The thiosemicarbazones are particularly effective in the stimulation of human peripheral blood mononuclear cells for the production of cytokines, such as TNF-$\alpha$.

O. Tryptanthrin Compounds.

Examples of tryptanthrin compounds, as well as methods of formulating, manufacturing, and screening for compounds all suitable for use as adjuvants in the invention include those described in ref. 209. The tryptanthrin compounds are particularly effective in the stimulation of human peripheral blood mononuclear cells for the production of cytokines, such as TNF-$\alpha$.

The invention may also comprise combinations of aspects of one or more of the adjuvants identified above. For example, the following combinations may be used as adjuvant compositions in the invention: (1) a saponin and an oil-in-water emulsion [210]; (2) a saponin (e.g. QS21)+a non-toxic LPS derivative (e.g. 3dMPL) [211]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [212]; (5) combinations of 3dMPL with, for example, QS21 and/or oil-in-water emulsions [213]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 141.

The use of aluminium salt adjuvants is particularly useful, and antigens are generally adsorbed to such salts. The Menjugate™ and NeisVac™ conjugates use a hydroxide adjuvant, whereas Meningitec™ uses a phosphate adjuvant. It is possible in compositions of the invention to adsorb some antigens to an aluminium hydroxide but to have other antigens in association with an aluminium phosphate. Typically, however, only a single salt is used, e.g. a hydroxide or a phosphate, but not both. Not all conjugates need to be adsorbed i.e. some or all can be free in solution.

Methods of Treatment

The invention also provides a method for raising an immune response in a mammal, comprising administering a pharmaceutical composition of the invention to the mammal. The immune response is preferably protective and preferably involves antibodies. The method may raise a booster response.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc. A preferred class of humans for treatment are patients at risk of nosocomial infection, particularly those with end-stage renal disease and/or on haemodialysis. Other patients at risk of nosocomial infection are also preferred, e.g. immunodeficient patients or those who have undergone surgery, especially cardiac surgery, or trauma. Another preferred class of humans for treatment are patients at risk of bacteremia. A further preferred class are patients suffering from or previously exposed to influenza virus, as *S. aureus* has been linked with post-infection pneumonia in these patients.

The invention also provides a composition of the invention for use as a medicament. The medicament is preferably able to raise an immune response in a mammal (i.e. it is an immunogenic composition) and is more preferably a vaccine.

The invention also provides the use of a conjugate of the invention in the manufacture of a medicament for raising an immune response in a mammal.

These uses and methods are preferably for the prevention and/or treatment of a disease caused by *S. aureus*, e.g. skin infections, such as impetigo, boils, cellulitis folliculitis, styes, furuncles, carbuncles, scalded skin syndrome and abscesses, septic arthritis, pneumonia, mastitis, phlebitis, meningitis, urinary tract infections, osteomyelitis, endocarditis, toxic shock syndrome (TSS), septicaemia and nosocomial infections.

One way of checking efficacy of therapeutic treatment involves monitoring *S. aureus* infection after administration of the composition of the invention. One way of checking efficacy of prophylactic treatment involves monitoring immune responses against the *S. aureus* antigens after administration of the composition.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

S. aureus Antigens

As mentioned above, one or more further S. aureus antigens can be included in compositions of the invention. The antigens may be protein or saccharide antigens. S. aureus protein antigens may be used as carrier proteins for conjugates of the invention, carrier proteins for other conjugates, or as unconjugated protein antigens. S. aureus saccharide antigens may be used as the saccharides for other conjugate or as unconjugated saccharide antigens.

Suitable S. aureus saccharide antigens include the exopolysaccharide of S. aureus, which is a poly-N-acetylglucosamine (PNAG). This polysaccharide is present in both S. aureus and S. epidermidis and can be isolated from either source [214,215]. For example, PNAG may be isolated from S. aureus strain MN8m [216]. The saccharide antigen may be a polysaccharide having the size that arises during purification of the exopolysaccharide from bacteria, or it may be an polysaccharide achieved by fragmentation of such a polysaccharide e.g. size can vary from over 400 kDa to between 75 and 400 kDa, or between 10 and 75 kDa, or up to 30 repeat units. The saccharide antigen can have various degrees of N-acetylation and, as described in reference 217, the PNAG may be less than 40% N-acetylated (e.g. less than 35, 30, 20, 15, 10 or 5% N-acetylated; deacetylated PNAG is also known as dPNAG). Deacetylated epitopes of PNAG can elicit antibodies that are capable of mediating opsonic killing. The preparation of dPNAG is described in reference 218. The PNAG may or may not be O-succinylated e.g. it may be O-succinylated on fewer less than 25, 20, 15, 10, 5, 2, 1 or 0.1% of residues. The PNAG may be conjugated to a carrier molecule as described above or alternatively unconjugated.

Another suitable S. aureus saccharide antigen is the type 336 antigen, which is a β-linked hexosamine with no O-acetylation [219,220]. The type 336 antigen is cross-reactive with antibodies raised against the 336 strain (ATCC 55804). The type 336 antigen may be conjugated to a carrier molecule as described above or alternatively unconjugated.

Suitable S. aureus protein antigens include the following S. aureus antigens (or antigens comprising immunogenic fragment(s) thereof) [e.g. see references 221-228]: AhpC, AhpF, Autolysin amidase, Autolysin glucosaminidase, Collagen binding protein CAN, EbhB, GehD lipase, Heparin binding protein HBP (17 kDa), Laminin receptor, MAP, MntC (also known as SitC), MRPII, Npase, ORF0594, ORF0657n, ORF0826, PBP4, RAP (RNA III activating protein), Sai-1, SasK, SBI, SdrG, SdrH, SSP-1, SSP-2 and Vitronectin-binding protein.

Further suitable S. aureus protein antigens include a clfA antigen; a clfB antigen; a sdrE2 antigen; a sdrC antigen; a sasF antigen, a emp antigen; a sdrD antigen; a spa antigen; a esaC antigen; a esxA antigen; a esxB antigen; a sta006 antigen; a isdC antigen; a Hla antigen; a sta011 antigen; a isdA antigen; a isdB antigen; and a sta073 antigen, as described below. One or more (i.e. 1, 2, 3, 4, 5, 6 or more) of these antigens may be present in a composition of the invention. Of these antigens, the use of one or more (i.e. 1, 2, 3, 4, 5, 6 or more) of a esxA antigen; a esxB antigen; a sta006 antigen; a Hla antigen; a sta011 antigen; and/or a sta073 antigen is specifically envisaged.

For example, a composition of the invention may further comprise one of the following combinations of S. aureus protein antigens:

(1) A esxA antigen, a esxB antigen, a sta006 antigen and a Hla antigen. The esxA and esxB antigens can usefully be combined as a hybrid polypeptide, as discussed below, e.g. a EsxAB hybrid with a esxB antigen downstream of a esxA antigen. The Hla antigen may be a detoxified mutant e.g. including a H35L mutation.

(2) A esxA antigen, a esxB antigen, a sta006 antigen and a sta011 antigen. The esxA and esxB antigens may be combined as a hybrid polypeptide, as discussed below, e.g. an EsxAB hybrid.

(3) A esxA antigen, a esxB antigen and a sta011 antigen. The esxA and esxB antigens can usefully be combined as a hybrid polypeptide, as discussed below, e.g. a EsxAB hybrid.

(4) A esxA antigen, a esxB antigen, a Hla antigen, a sta006 antigen and a sta011 antigen. The esxA and esxB antigens may be combined as a hybrid polypeptide, as discussed below, e.g. an EsxAB hybrid. The Hla antigen may be a detoxified mutant e.g. including a H35L mutation.

(5) A esxA antigen, a esxB antigen and a Hla antigen. The esxA and esxB antigens can usefully be combined as a hybrid polypeptide, as discussed below, e.g. a EsxAB hybrid. The Hla antigen may be a detoxified mutant e.g. including a H35L mutation.

(6) A Hla antigen, a sta006 antigen and a sta011 antigen. The Hla antigen may be a detoxified mutant e.g. including a H35L mutation.

(7) A esxA antigen and a esxB antigen. The esxA and esxB antigens can usefully be combined as a hybrid polypeptide, as discussed below, e.g. an EsxAB hybrid.

(8) A esxA antigen, a esxB antigen and a sta006 antigen. The esxA and esxB antigens can usefully be combined as a hybrid polypeptide, as discussed below, e.g. a EsxAB hybrid.

(9) A esxA antigen, a esxB antigen, a sta011 antigen and a sta073 antigen. The esxA and esxB antigens may be combined as a hybrid polypeptide, as discussed below, e.g. an EsxAB hybrid.

(10) A sta006 antigen and a sta011 antigen.

Further *Staphylococcus aureus* antigens are disclosed in reference 229.

clfA

The 'clfA' antigen is annotated as 'clumping factor A'. In the NCTC 8325 strain clfA is SAOUHSC_00812 and has amino acid sequence SEQ ID NO: 1 (GI:88194572). In the Newman strain it is nwmn_0756 (GI: 151220968).

Useful clfA antigens can elicit an antibody (e.g. when administered to a human) that recognises SEQ ID NO: 1 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 1; and/or (b) comprising a fragment of at least 'n' consecutive amino acids of SEQ ID NO: 1, wherein 'n' is 7 or more (e.g. 8, 10, 12, 14, 16, 18, 20, 25, 30, 35, 40, 50, 60, 70, 80, 90, 100, 150, 200, 250 or more). These clfA proteins include variants of SEQ ID NO: 1. Preferred fragments of (b) comprise an epitope from SEQ ID NO: 1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 1 while retaining at least one epitope of SEQ ID NO: 1. The final 368 C-terminal amino acids of SEQ ID NO: 1 can usefully be omitted. The first 39 N-terminal amino acids of SEQ ID NO: 1 can usefully be omitted. Other fragments omit one or more protein domains.

SEQ ID NO: 2 is a useful fragment of SEQ ID NO: 1 ('$ClfA_{40-559}$'). This fragments omits the long repetitive region towards the C-terminal of SEQ ID NO: 1.

clfB

The 'clfB' antigen is annotated as 'clumping factor B'. In the NCTC 8325 strain clfB is SAOUHSC_02963 and has amino acid sequence SEQ ID NO: 3 (GI:88196585). In the Newman strain it is nwmn_2529 (GI:151222741).

Useful clfB antigens can elicit an antibody (e.g. when administered to a human) that recognises SEQ ID NO: 3 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 3; and/or (b) comprising a fragment of at least 'n' consecutive amino acids of SEQ ID NO: 3, wherein 'n' is 7 or more (e.g. 8, 10, 12, 14, 16, 18, 20, 25, 30, 35, 40, 50, 60, 70, 80, 90, 100, 150, 200, 250 or more). These clfB proteins include variants of SEQ ID NO: 3. Preferred fragments of (b) comprise an epitope from SEQ ID NO: 3. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 3 while retaining at least one epitope of SEQ ID NO: 3. The final 40 C-terminal amino acids of SEQ ID NO: 3 can usefully be omitted. The first 44 N-terminal amino acids of SEQ ID NO: 3 can usefully be omitted. Other fragments omit one or more protein domains. ClfB is naturally a long protein and so the use of fragments is helpful e.g. for purification, handling, fusion, expression, etc.

SEQ ID NO: 4 is a useful fragment of SEQ ID NO: 3 ('$ClfB_{45-552}$'). This fragment includes the most exposed domain of ClfB and is more easily used at an industrial scale. It also reduces the antigen's similarity with human proteins. Other useful fragments, based on a 3-domain model of ClfB, include: $ClfB_{45-360}$ (also known as CLfB-N12; SEQ ID NO: 5); $ClfB_{212-542}$ (also known as CLfB-N23; SEQ ID NO: 6); and $ClfB_{360-542}$ (also known as CLfB-N3; SEQ ID NO: 7).

sdrE2

The 'sdrE2' antigen is annotated as 'Ser-Asp rich fibrinogen/bone sialoprotein-binding protein SdrE'. In the Newman strain sdrE2 is NWMN_0525 and has amino acid sequence SEQ ID NO: 8 (GI:151220737).

Useful sdrE2 antigens can elicit an antibody (e.g. when administered to a human) that recognises SEQ ID NO: 8 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 8; and/or (b) comprising a fragment of at least 'n' consecutive amino acids of SEQ ID NO: 8, wherein 'n' is 7 or more (e.g. 8, 10, 12, 14, 16, 18, 20, 25, 30, 35, 40, 50, 60, 70, 80, 90, 100, 150, 200, 250 or more). These sdrE2 proteins include variants of SEQ ID NO: 8. Preferred fragments of (b) comprise an epitope from SEQ ID NO: 8. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 8 while retaining at least one epitope of SEQ ID NO: 8. The final 38 C-terminal amino acids of SEQ ID NO: 8 can usefully be omitted. The first 52 N-terminal amino acids of SEQ ID NO: 8 can usefully be omitted. Other fragments omit one or more protein domains. SdrE2 is naturally a long protein and so the use of fragments is very helpful e.g. for purification, handling, fusion, expression, etc.

SEQ ID NO: 9 is a useful fragment of SEQ ID NO: 8 ('$SdrE_{53-632}$'). This fragment includes the most exposed domain of SdrE2 and is more easily used at an industrial scale. It also reduces the antigen's similarity with human proteins.

sdrC

The 'sdrC' antigen is annotated as 'sdrC protein'. In the NCTC 8325 strain sdrC is SAOUHSC_00544 and has amino acid sequence SEQ ID NO: 10 (GI:88194324).

Useful sdrC antigens can elicit an antibody (e.g. when administered to a human) that recognises SEQ ID NO: 10 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). These sdrC proteins include variants of SEQ ID NO: 10. Preferred fragments of (b) comprise an epitope from SEQ ID NO: 10. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 10 while retaining at least one epitope of SEQ ID NO: 10. The final 38 C-terminal amino acids of SEQ ID NO: 10 can usefully be omitted. The first 50 N-terminal amino acids of SEQ ID NO: 10 can usefully be omitted. Other fragments omit one or more protein domains. SdrC is naturally a long protein and so the use of fragments is helpful e.g. for purification, handling, fusion, expression, etc.

SEQ ID NO: 11 is a useful fragment of SEQ ID NO: 10 ('$SdrC5_{1-518}$'). This fragment includes the most exposed domain of SdrC and is more easily used at an industrial scale. It also reduces the antigen's similarity with human proteins.

sasF

The 'sasF' antigen is annotated as 'sasF protein'. In the NCTC 8325 strain sasF is SAOUHSC_02982 and has amino acid sequence SEQ ID NO: 12 (GI:88196601).

Useful sasF antigens can elicit an antibody (e.g. when administered to a human) that recognises SEQ ID NO: 12 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). These sasF proteins include variants of SEQ ID NO: 12. Preferred fragments of (b) comprise an epitope from SEQ ID NO: 12. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 12 while retaining at least one epitope of SEQ ID NO: 12. The final 39 C-terminal amino acids of SEQ ID NO: 12 can usefully be omitted. The first 37 N-terminal amino acids of SEQ ID NO: 12 can usefully be omitted. Other fragments omit one or more protein domains.

emp

The 'emp' antigen is annotated as 'extracellular matrix and plasma binding protein'. In the NCTC 8325 strain emp is SAOUHSC_00816 and has amino acid sequence SEQ ID NO: 13 (GI:88194575). In the Newman strain it is nwmn_0758 (GI: 151220970).

Useful emp antigens can elicit an antibody (e.g. when administered to a human) that recognises SEQ ID NO: 13 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). These emp proteins include variants of SEQ ID NO: 13. Preferred fragments of (b) comprise an epitope from SEQ ID NO: 13. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 13 while retaining at least one epitope of SEQ ID NO: 13. The first 26 N-terminal amino acids of SEQ ID NO: 13 can usefully be omitted. Other fragments omit one or more protein domains.

SEQ ID NOs: 14, 15, 16 and 17 are useful fragments of SEQ ID NO: 13 ('Emp$_{35-340}$', 'Emp$_{27-334}$', 'Emp$_{35-334}$' and 'Emp$_{27-147}$', respectively).

sdrD

The 'sdrD' antigen is annotated as 'sdrD protein'. In the NCTC 8325 strain sdrD is SAOUHSC_00545 and has amino acid sequence SEQ ID NO: 18 (GI:88194325).

Useful sdrD antigens can elicit an antibody (e.g. when administered to a human) that recognises SEQ ID NO: 18 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 18; and/or (b) comprising a fragment of at least 'n' consecutive amino acids of SEQ ID NO: 18, wherein 'n' is 7 or more (e.g. 8, 10, 12, 14, 16, 18, 20, 25, 30, 35, 40, 50, 60, 70, 80, 90, 100, 150, 200, 250 or more). These sdrD proteins include variants of SEQ ID NO: 18. Preferred fragments of (b) comprise an epitope from SEQ ID NO: 18. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 18 while retaining at least one epitope of SEQ ID NO: 18. The final 38 C-terminal amino acids of SEQ ID NO: 18 can usefully be omitted. The first 52 N-terminal amino acids of SEQ ID NO: 18 can usefully be omitted. Other fragments omit one or more protein domains. SdrD is naturally a long protein and so the use of fragments is very helpful e.g. for purification, handling, fusion, expression, etc.

SEQ ID NO: 19 is a useful fragment of SEQ ID NO: 18 ('SdrD$_{53-592}$'). This fragment includes the most exposed domain of SdrD and is more easily used at an industrial scale. It also reduces the antigen's similarity with human proteins. A nother useful fragment, with the same C-terminus residue, is SdrD$_{394-592}$ (also known as SdrD-N3; SEQ ID NO: 20).

spa

The 'spa' antigen is annotated as 'protein A' or 'SpA'. In the NCTC 8325 strain spa is SAOUHSC_00069 and has amino acid sequence SEQ ID NO: 21 (GI:88193885). In the Newman strain it is nwmn_0055 (GI:151220267). All *S. aureus* strains express the structural gene for spa, a well characterized virulence factor whose cell wall-anchored surface protein product has five highly homologous immunoglobulin binding domains designated E, D, A, B, and C [230]. These domains display ~80% identity at the amino acid level, are 56 to 61 residues in length, and are organized as tandem repeats [231]. SpA is synthesized as a precursor protein with an N-terminal signal peptide and a C-terminal sorting signal [232,233]. Cell wall-anchored spa is displayed in great abundance on the staphylococcal surface [234,235]. Each of its immunoglobulin binding domains is composed of anti-parallel α-helices that assemble into a three helix bundle and can bind the Fc domain of immunoglobulin G (IgG) [236,237], the VH3 heavy chain (Fab) of IgM (i.e. the B cell receptor) [238], the von Willebrand factor at its A1 domain [239] and/or the TNF-α receptor I (TNFRI) [240], which is displayed on surfaces of airway epithelia.

Useful spa antigens can elicit an antibody (e.g. when administered to a human) that recognises SEQ ID NO: 21 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 21; and/or (b) comprising a fragment of at least 'n' consecutive amino acids of SEQ ID NO: 21, wherein 'n' is 7 or more (e.g. 8, 10, 12, 14, 16, 18, 20, 25, 30, 35, 40, 50, 60, 70, 80, 90, 100, 150, 200, 250 or more). These spa proteins include variants of SEQ ID NO: 21. Preferred fragments of (b) comprise an epitope from SEQ ID NO: 21. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 21 while retaining at least one epitope of SEQ ID NO: 21. The final 35 C-terminal amino acids of SEQ ID NO: 21 can usefully be omitted. The first 36 N-terminal amino acids of SEQ ID NO: 21 can usefully be omitted. Other fragments omit one or more protein domains. Reference 241 suggests that individual IgG-binding domains might be useful immunogens, alone or in combination.

SEQ ID NO: 22 is a useful fragment of SEQ ID NO: 21 ('Spa$_{37-325}$'). This fragment contains all the five SpA Ig-binding domains and includes the most exposed domain of SpA. It also reduces the antigen's similarity with human proteins. Other useful fragments may omit 1, 2, 3 or 4 of the natural A, B, C, D and/or E domains. As reported in reference 241, other useful fragments may include only 1, 2, 3 or 4 of the natural A, B, C, D and/or E domains e.g. comprise only the SpA(A) domain but not B to E, or comprise only the SpA(D) domain but not A, B, C or E, etc. Thus a spa antigen useful with the invention may include 1, 2, 3, 4 or 5 IgG-binding domains, but ideally has 4 or fewer. If an antigen includes only one type of spa domain (e.g. only the Spa(A) or SpA(D) domain), it may include more than one copy of this domain e.g. multiple SpA(D) domains in a single polypeptide chain. An individual domain within the antigen may be mutated at 1, 2, 3, 4, 5, 6, 7, 8, 9, 10 or more amino acids relative to SEQ ID NO: 21 (e.g. see ref. 241, disclosing mutations at residues 3 and/or 24 of domain D, at residue 46 and/or 53 of domain A, etc.). Such mutants should not remove the antigen's ability to elicit an antibody that recognises SEQ ID NO: 21, but may remove the antigen's binding to IgG. In certain aspects a spa antigen includes a substitution at (a) one or more amino acid substitution in an IgG Fc binding sub-domain of SpA domain A, B, C, D and/or E that disrupts or decreases binding to IgG Fc Hla The 'Hla' antigen is the 'alpha-hemolysin precursor' also known as 'alpha toxin' or simply 'hemolysin'. In the NCTC 8325 strain Hla is SAOUHSC_01121 and has amino acid sequence SEQ ID NO: 28 (GI:88194865). In the Newman strain it is nwmn_1073 (GI:151221285). Hla is an important virulence determinant produced by most strains of *S. aureus*, having pore-forming and haemolytic activity. Anti-Hla antibodies can neutralise the detrimental effects of the toxin in animal models, and Hla is particularly useful for protecting against pneumonia.

Useful Hla antigens can elicit an antibody (e.g. when administered to a human) that recognises SEQ ID NO: 28 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 28; and/or (b) comprising a fragment of at least 'n' consecutive amino acids of SEQ ID NO: 28, wherein 'n' is 7 or more (e.g. 8, 10, 12, 14, 16, 18, 20, 25, 30, 35, 40, 50, 60, 70, 80, 90, 100, 150, 200, 250 or more). These Hla proteins include variants of SEQ ID NO: 28. Preferred fragments of (b) comprise an epitope from SEQ ID NO: 28. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 28 while retaining at least one epitope of SEQ ID NO: 28. The first 26 N-terminal amino acids of SEQ ID NO: 28 can usefully be omitted. Truncation at the C-terminus can also be used e.g. leaving only 50 amino acids (residues 27-76 of SEQ ID NO: 28) [245]. Other fragments omit one or more protein domains.

Hla's toxicity can be avoided in compositions of the invention by chemical inactivation (e.g. using formaldehyde, glutaraldehyde or other cross-linking reagents). Instead, however, it is preferred to use mutant forms of Hla which remove its toxic activity while retaining its immunogenicity. Such detoxified mutants are already known in the art. One useful Hla antigen has a mutation at residue 61 of SEQ ID NO: 28, which is residue 35 of the mature antigen (i.e. after omitting the first 26 N-terminal amino acids). Thus residue 61 may not be histidine, and may instead be e.g. Ile, Val or preferably Leu. A His-Arg mutation at this position can also be used. For example, SEQ ID NO: 29 is the mature mutant Hla-H35L sequence and a useful Hla antigen comprises SEQ ID NO: 29. Another useful mutation replaces a long loop with a short sequence e.g. to replace the 39mer at residues 136-174 of SEQ ID NO: 28 with a tetramer such as PSGS (SEQ ID NO: 30), as in SEQ ID NO: 31 (which also includes the H35L mutation) and SEQ ID NO: 32 (which does not include the H35L mutation).

Further useful Hla antigens are disclosed in references 246 and 247.

SEQ ID NOs: 33, 34 & 35 are three useful fragments of SEQ ID NO: 28 ('Hla$_{27-76}$', 'Hla$_{27-89}$' and 'Hla$_{27-79}$', respectively). SEQ ID NOs: 36, 37 and 38 are the corresponding fragments from SEQ ID NO: 29.

sta011

The 'sta011' antigen is annotated as 'lipoprotein'. In the NCTC 8325 strain sta011 is SAOUHSC_00052 and has amino acid sequence SEQ ID NO: 39 (GI:88193872).

Useful sta011 antigens can elicit an antibody (e.g. when administered to a human) that recognises SEQ ID NO: 39 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 39; and/or (b) comprising a fragment of at least 'n' consecutive amino acids of SEQ ID NO: 39, wherein 'n' is 7 or more (e.g. 8, 10, 12, 14, 16, 18, 20, 25, 30, 35, 40, 50, 60, 70, 80, 90, 100, 150, 200, 250 or more). These sta011 proteins include variants of SEQ ID NO: 39. Preferred fragments of (b) comprise an epitope from SEQ ID NO: 39. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 39 while retaining at least one epitope of SEQ ID NO: 39. The first 23 N-terminal amino acids of SEQ ID NO: 39 can usefully be omitted. Other fragments omit one or more protein domains. A sta006 antigen may be lipidated e.g. with an acylated N-terminus cysteine.

Variant forms of SEQ ID NO: 39 which may be used for preparing sta011 antigens include, but are not limited to, SEQ ID NOs: 40, 41 and 42 with various Ile/Val/Leu substitutions.

isdA

The 'isdA' antigen is annotated as 'IsdA protein'. In the NCTC 8325 strain isdA is SAOUHSC_01081 and has amino acid sequence SEQ ID NO: 43 (GI:88194829). In the Newman strain it is nwmn_1041 (GI:151221253).

Useful isdA antigens can elicit an antibody (e.g. when administered to a human) that recognises SEQ ID NO: 43 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 43; and/or (b) comprising a fragment of at least 'n' consecutive amino acids of SEQ ID NO: 43, wherein 'n' is 7 or more (e.g. 8, 10, 12, 14, 16, 18, 20, 25, 30, 35, 40, 50, 60, 70, 80, 90, 100, 150, 200, 250 or more). These isdA proteins include variants of SEQ ID NO: 43. Preferred fragments of (b) comprise an epitope from SEQ ID NO: 43. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 43 while retaining at least one epitope of SEQ ID NO: 43. The final 38 C-terminal amino acids of SEQ ID NO: 43 can usefully be omitted. The first 46 N-terminal amino acids of SEQ ID NO: 43 can usefully be omitted. Truncation to exclude the C-terminal 38mer of SEQ ID NO: 43 (beginning with the LPKTG (SEQ ID NO: 55) motif) is also useful. Other fragments omit one or more protein domains.

SEQ ID NO: 44 is a useful fragment of SEQ ID NO: 43 (amino acids 40-184 of SEQ ID NO: 43; 'IsdA$_{40-184}$') which includes the natural protein's heme binding site and includes the antigen's most exposed domain. It also reduces the antigen's similarity with human proteins. Other useful fragments are disclosed in references 248 and 249.

IsdA does not adsorb well to aluminium hydroxide adjuvants, so IsdA present in a composition may me unadsorbed or may be adsorbed to an alternative adjuvant e.g. to an aluminium phosphate.

isdB

The 'isdB' antigen is annotated as 'neurofilament protein isdB'. In the NCTC 8325 strain isdB is SAOUHSC_01079 and has amino acid sequence SEQ ID NO: 45 (GI: 88194828). IsdB has been proposed for use as a vaccine antigen on its own [250], but this may not prevent pneumonia.

Useful isdB antigens can elicit an antibody (e.g. when administered to a human) that recognises SEQ ID NO: 45 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 45; and/or (b) comprising a fragment of at least 'n' consecutive amino acids of SEQ ID NO: 45, wherein 'n' is 7 or more (e.g. 8, 10, 12, 14, 16, 18, 20, 25, 30, 35, 40, 50, 60, 70, 80, 90, 100, 150, 200, 250 or more). These isdB proteins include variants of SEQ ID NO: 45. Preferred fragments of (b) comprise an epitope from SEQ ID NO: 45. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 45 while retaining at least one epitope of SEQ ID NO: 45. The final 36 C-terminal amino acids of SEQ ID NO: 45 can usefully be omitted. The first 40 N-terminal amino acids of SEQ ID NO: 45 can usefully be omitted. Other fragments omit one or more protein domains. Useful fragments of IsdB are disclosed in references 249 and 251 e.g. lacking 37 internal amino acids of SEQ ID NO: 45.

In some embodiments, compositions of the invention do not include an isdB antigen.

sta073

The 'sta073' antigen is annotated as 'bifunctional autolysin precursor'. In the NCTC 8325 strain sta073 is SAOUHSC_00994 and has amino acid sequence SEQ ID NO: 46 (GI:88194750). In the Newman strain it is nwmn_0922 (GI: 151221134). Proteomic analysis has revealed that this protein is secreted or surface-exposed.

Useful sta073 antigens can elicit an antibody (e.g. when administered to a human) that recognises SEQ ID NO: 46 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 46; and/or (b) comprising a fragment of at least 'n' consecutive amino acids of SEQ ID NO: 46, wherein 'n' is 7 or more (e.g. 8, 10, 12, 14, 16, 18, 20, 25, 30, 35, 40, 50, 60, 70, 80, 90, 100, 150, 200, 250 or more). These sta073 proteins include variants of SEQ ID NO: 46. Preferred fragments of (b) comprise an epitope from SEQ ID NO: 46. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 46 while retaining at least one epitope of SEQ ID NO: 46. The first 24 N-terminal amino acids of SEQ ID NO: 46 can usefully be omitted. Other fragments omit one or more protein domains.

Sta073 does not adsorb well to aluminium hydroxide adjuvants, so Sta073 present in a composition may me unadsorbed or may be adsorbed to an alternative adjuvant e.g. to an aluminium phosphate.

Hybrid Polypeptides

*S. aureus* protein antigens used in the invention may be present in the composition as individual separate polypeptides. Where more than one antigen is used, however, they do not have to be present as separate polypeptides. Instead, at least two (e.g. 2, 3, 4, 5, or more) antigens can be expressed as a single polypeptide chain (a 'hybrid' polypeptide). Hybrid polypeptides offer two main advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful.

The hybrid polypeptide may comprise two or more polypeptide sequences from each of the antigens listed above, or two or more variants of the same antigen in the cases in which the sequence has partial variability across strains. Hybrids consisting of amino acid sequences from two, three, four, five, six, seven, eight, nine, or ten antigens are useful. In particular, hybrids consisting of amino acid sequences from two, three, four, or five antigens are preferred, such as two or three antigens.

Different hybrid polypeptides may be mixed together in a single formulation. Hybrids may be combined with non-hybrid antigens selected from the first, second or third antigen groups. Within such combinations, an antigen may be present in more than one hybrid polypeptide and/or as a non-hybrid polypeptide. It is preferred, however, that an antigen is present either as a hybrid or as a non-hybrid, but not as both.

Hybrid polypeptides can be represented by the formula $NH_2$-A-$\{$-X-L-$\}_n$-B—COOH, wherein: X is an amino acid sequence of a *S. aureus* antigen, as described above; L is an optional linker amino acid sequence; A is an optional N-terminal amino acid sequence; B is an optional C-terminal amino acid sequence; n is an integer of 2 or more (e.g. 2, 3, 4, 5, 6, etc.). Usually n is 2 or 3.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of $\{$-X-L-$\}$, linker amino acid sequence -L- may be present or absent. For instance, when n=2 the hybrid may be $NH_2$—$X_1$-$L_1$-$X_2$-$L_2$-COOH, $NH_2$—$X_1$-$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising Gly, where n=2, 3, 4, 5, 6, 7, 8, 9, 10 or more), and histidine tags (i.e. His, where n=3, 4, 5, 6, 7, 8, 9, 10 or more). Other suitable linker amino acid sequences will be apparent to those skilled in the art. A useful linker is GSGGGG (SEQ ID NO: 47) or GSGSGGGG (SEQ ID NO: 48), with the Gly-Ser dipeptide being formed from a BamHI restriction site, thus aiding cloning and manipulation, and the $(Gly)_4$ tetrapeptide being a typical poly-glycine linker. Other suitable linkers, particularly for use as the final $L_n$ are ASGGGS (SEQ ID NO: 49) e.g. encoded by SEQ ID NO: 50) or a Leu-Glu dipeptide.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His, where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine e.g. Met-Ala-Ser, or a single Met residue.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. His, where n=3, 4, 5, 6, 7, 8, 9, 10 or more, such as SEQ ID NO: 51), or sequences which enhance protein stability. Other suitable C-terminal amino acid sequences will be apparent to those skilled in the art.

One hybrid polypeptide of the invention may include both EsxA and EsxB antigens. These may be in either order, N- to C-terminus. SEQ ID NOs: 52 ('EsxAB'; encoded by SEQ ID NO: 53) and 54 ('EsxBA') are examples of such hybrids, both having hexapeptide linkers ASGGGS (SEQ ID NO: 49).

General

The practice of the present invention will employ, unless otherwise indicated, conventional methods of chemistry, biochemistry, molecular biology, immunology and pharmacology, within the skill of the art. Such techniques are explained fully in the literature. See, e.g., references 252-259, etc.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed. References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 260. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 261.

Where the invention concerns an "epitope", this epitope may be a B-cell epitope and/or a T-cell epitope. Such epitopes can be identified empirically (e.g. using PEPSCAN [262,263] or similar methods), or they can be predicted (e.g. using the Jameson-Wolf antigenic index [264], matrix-based approaches [265], MAPITOPE [266], TEPITOPE [267, 268], neural networks [269], OptiMer & EpiMer [270, 271], ADEPT [272], Tsites [273], hydrophilicity [274], antigenic index [275] or the methods disclosed in references 276-280, etc.). Epitopes are the parts of an antigen that are recognised by and bind to the antigen binding sites of antibodies or T-cell receptors, and they may also be referred to as "antigenic determinants".

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the invention can also provide a process involving less than the total number of steps. For example, the invention provides a process comprising the steps of: (a) depolymerising a *S. aureus* type 5 or type 8 capsular polysaccharide, to give a polysaccharide fragment; and (b) oxidising the fragment in order to introduce an aldehyde group into at least one saccharide residue in the fragment, to give an oxidised saccharide residue. The further step (c) need not be performed in order to fall within the scope of the invention, as the product of steps (a) and (b) has utility as an intermediate in conjugate preparation, and may be used, stored, exported, etc. for separate and later use. This later use might involve carrying out step (c). Alternatively, the product of steps (a) and (b) might be coupled to a carrier molecule in a different way, for example via a hydroxyl or carboxyl group that is retained in the oxidised saccharide residue.

Similarly, where a starting polysaccharide material is already partially processed then the invention encompasses processes involving only the later steps of a method. For example, the invention encompasses a process comprising a step of coupling an oxidised saccharide residue in a type 5 or type 8 capsular polysaccharide to a carrier molecule via an aldehyde group, in which the starting material for the process is a type 5 or type 8 capsular polysaccharide that was previously depolymerised to give a polysaccharide fragment and then oxidised to introduce an the aldehyde group into the saccharide residue.

These different steps can be performed at very different times by different people in different places (e.g. in different countries).

It will be appreciated that sugar rings can exist in open and closed form and that, whilst closed forms are shown in structural formulae herein, open forms are also encompassed by the invention. Similarly, it will be appreciated that sugars can exist in pyranose and furanose forms and that, whilst pyranose forms are shown in structural formulae herein, furanose forms are also encompassed. Different anomeric forms of sugars are also encompassed.

A primary amine can be represented by formula $NH_2R$. The R group will typically be electron donating, and includes $C_{1-8}$hydrocarbyl, particularly $C_{1-8}$alkyl, especially methyl. R is often $—CH_3$, $—C_2H_5$ or $—C_3H_7$. The hydrocarbyl may be substituted with one or more groups, such as: halogen (e.g. Cl, Br, F, I), trihalomethyl, $—NO_2$, —CN, $-N^+(C_{1-6}alkyl)_2O^-$, $—SO_3H$, $—SOC_{1-6}alkyl$, $—SO_2C_{1-6}alkyl$, $—SO_3C_{1-6}alkyl$, $—OC({=}O)OC_{1-6}alkyl$, $—C({=}O)H$, $—C({=}O)C_{1-6}alkyl$, $—OC({=}O)C_{1-6}alkyl$, $—N(C_{1-6}alkyl)_2$, $C_{1-6}alkyl$, $—N(C_{1-6}alkyl)_2$, $—C({=}O)N(C_{1-6}alkyl)_2$, $—N(C_{1-6}alkyl)C({=}O)O(C_{1-6}alkyl)$, $—N(C_{1-6}alkyl)C({=}O)N(C_{1-6}alkyl)_2$, $—CO_2H$, $—OC({=}O)N(C_{1-6}alkyl)_2$, $—N(C_{1-6}alkyl)C({=}O)C_{1-6}alkyl$, $—N(C_{1-6}alkyl)C({=}S)C_{1-6}alkyl$, $—N(C_{1-6}alkyl)S_2O_2N(C_{1-6}alkyl)_2$, $—CO_2C_{1-6}alkyl$, $—SO_2N(C_{1-6}alkyl)_2$, $—C({=}O)NH_2$, $—C({=}S)N(C_{1-6}alkyl)_2$, $—N(C_{1-6}alkyl)SO_2C_{1-6}alkyl$, $—N(C_{1-6}alkyl)C({=}S)N(C_{1-6}alkyl)_2$, $—NH—C_{1-6}alkyl$, $—S—C_{1-6}alkyl$ or $—O—C_{1-6}alkyl$. The term 'hydrocarbyl' includes linear, branched or cyclic monovalent groups consisting of carbon and hydrogen. Hydrocarbyl groups thus include alkyl, alkenyl and alkynyl groups, cycloalkyl (including polycycloalkyl), cycloalkenyl and aryl groups and combinations thereof, e.g. alkylcycloalkyl, alkylpolycycloalkyl, alkylaryl, alkenylaryl, cycloalkylaryl, cycloalkenylaryl, cycloalkylalkyl, polycycloalkylalkyl, arylalkyl, arylalkenyl, arylcycloalkyl and arylcycloalkenyl groups. Typical hydrocarbyl are $C_{1-14}$ hydrocarbyl, more particularly $C_{1-8}$ hydrocarbyl.

BRIEF DESCRIPTION OF DRAWINGS

FIG. 3 shows an S300 Sephacryl™ chromatogram of depolymerised type 5 capsular polysaccharide.

FIG. 4A compares 1D $^1H$ signals in the $^1H$ anomeric region for depolymerised and native type 5 capsular polysaccharide. Some notable differences are marked.

FIG. 7 shows SDS-PAGE analyses of S. aureus type 5 capsular polysaccharide-CRM197 conjugates made using methods of the invention.

MODES FOR CARRYING OUT THE INVENTION

Conjugate Production and Characterisation

Figure 1:
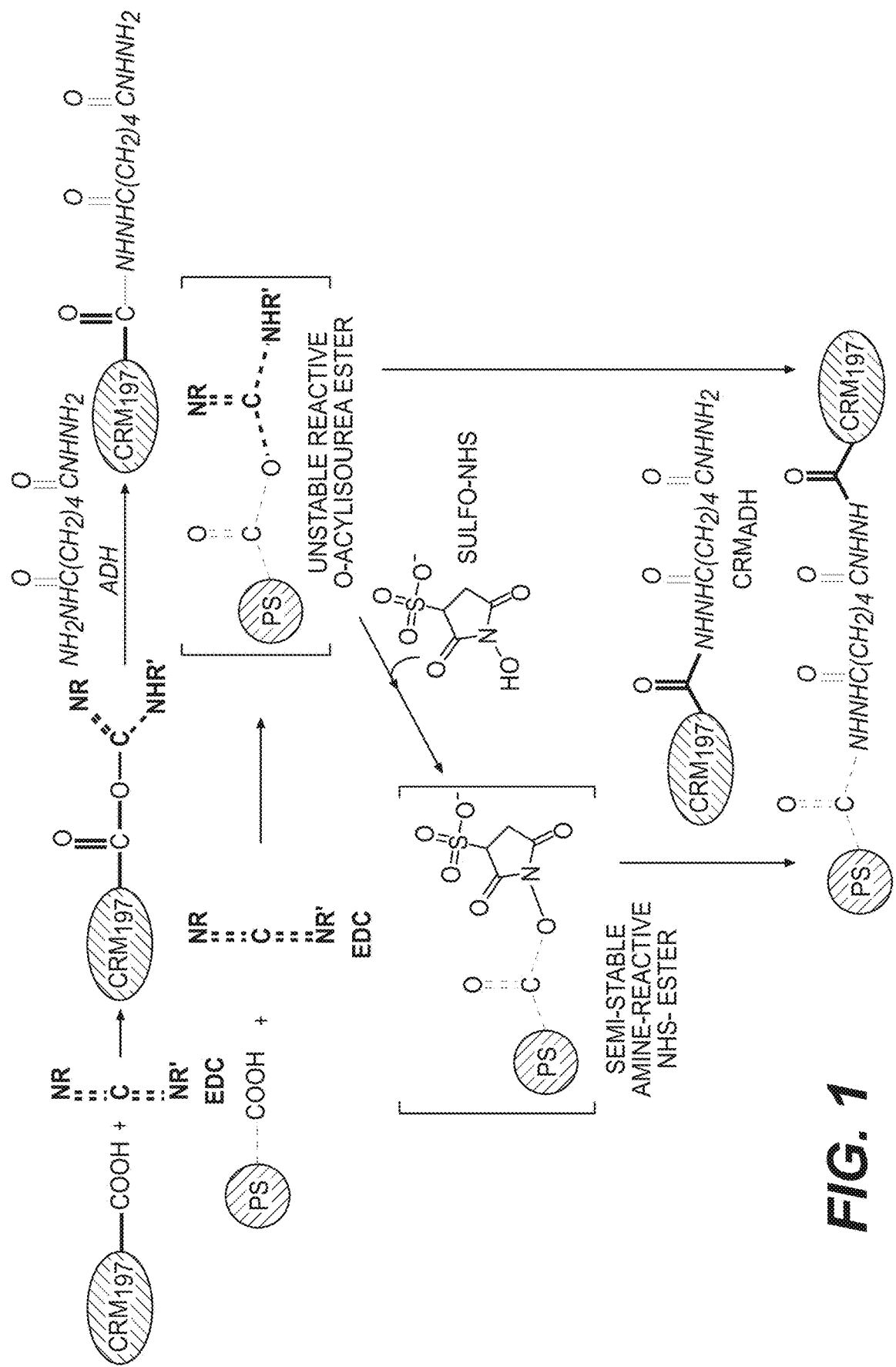
FIG. 1 shows a scheme for making an S. aureus type 5 capsular polysaccharide-CRM197 conjugate using an adipic acid dihydrazine linker and carbodiimide chemistry.

A purified S. aureus type 5 capsular polysaccharide was conjugated to CRM197 using carbodiimide chemistry and an adipic acid dihydrazine linker, similar to the method used in reference 2 (see below). In this method, the capsular polysaccharide is conjugated to derivatised CRM197 using EDC (FIG. 1). The reaction involves the carboxyl groups of the capsular polysaccharide. The carbodiimide (EDC) activates the carboxyl groups to bind to the —$NH_2$ group from the derivatised carrier protein (CRMadh), forming an amide linkage. The derivatised CRMadh is prepared using the same carbodiimide chemistry.

CRMadh Preparation:

To a solution of CRM197 was added 100 mM MES pH6.0 buffer in order to reach a final concentration of 10-12 mg/ml. Then 3.5 mg/ml of ADH (adipic acid dihydrazide) and 0.15 (EDC/CRM, w/w) was added, and the reaction kept under mild stirring for 1 h at RT. The mixture was then dialyzed against first 200 mM NaCl, 10 mM MES pH7.3 buffer and then against 5 mM MES pH7.0 buffer, using a 6-8 kDa membrane (SpectraPor). The product was characterized by MicroBCA, SDS-Page (3-8%), HPLC and MS. The CRMadh was found to be derivatised with 6-8 linker of ADH).

Conjugation Reaction:

The conjugation reaction was performed at capsular polysaccharide concentration of 2 mg/mL in 50 mM MES buffer pH6.04. The derivatised carrier protein, CRMadh, was added to the solution of capsular polysaccharide to a final concentration of 4.0 mg/ml. The solution was kept at RT for 3 h. The polysaccharide:protein ratio in the reaction mixture was 1:2 (weight/weight), the polysaccharide:EDC ratio was 1:6.66 (equivalent/equivalent) and the polysaccharide:SulfoNHS ratio was 1:0.53 (equivalent/equivalent).

Figure 2A:
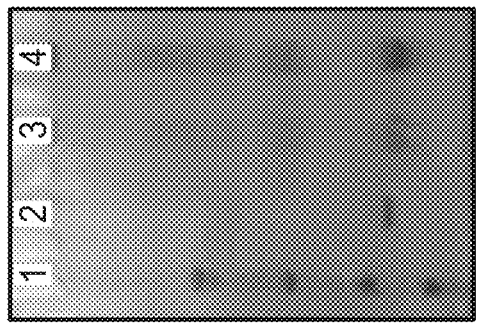
FIG. 2a shows an SDS-PAGE analysis of the S. aureus type 5 capsular polysaccharide-CRM197 conjugate made using an adipic acid dihydrazine linker and carbodiimide chemistry.
Figure 2B:
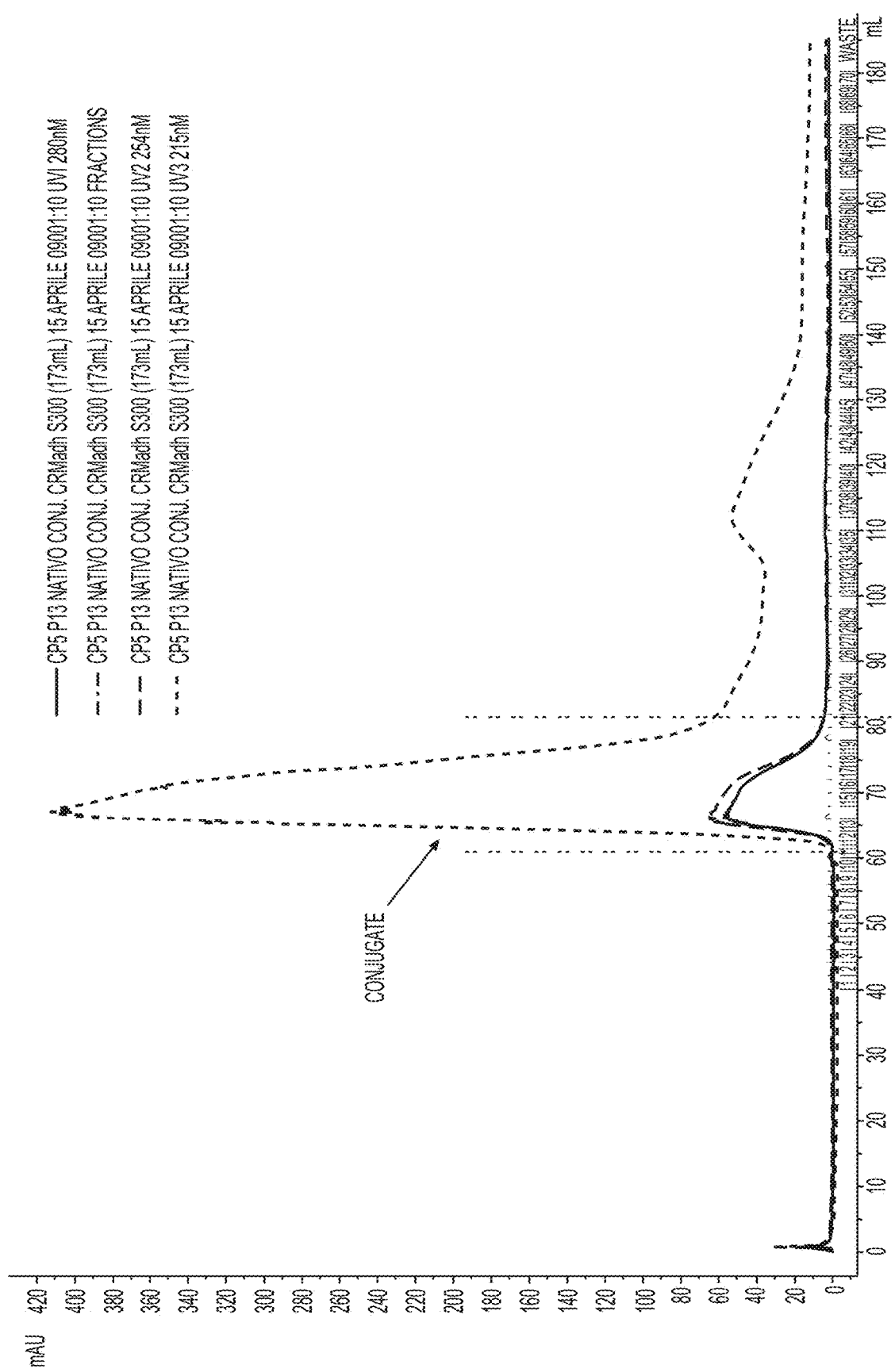
FIG. 2b shows an S300 Sephacryl™ chromatogram of the S. aureus type 5 capsular polysaccharide-CRM197 conjugate made using an adipic acid dihydrazine linker and carbodiimide chemistry.

After 3 h, formation of the conjugate was verified by SDS-PAGE using a NuPAGE® 3-8% Tris-Acetate Gel (Invitrogen) (FIG. 2a). After conjugation, the conjugate was purified by gel-filtration chromatography (performed on an Akta™ system (G&E Healthcare) using a S300 Sephacryl™ resin (G&E Healthcare), with a 10 mM NaPi, 10 mM NaCl, pH7.2 mobile phase buffer). The conjugate was detected at 215 nm, 254 nm and 280 nm (FIG. 2b). The conjugate solution was stored at −20° C. until further use. Total saccharide in the conjugate was determined by HPAEC-PAD analysis and protein content by MicroBCA assay, as described in reference 281 (Table 1).

TABLE 1

| Conjugate (lot) | Protein (µg/ml) | Saccharide (µg/ml) | Saccharide/protein (w/w) |
| --- | --- | --- | --- |
| 1 | 26.00 | 12.10 | 0.47 |
| 2 | 33.90 | 11.00 | 0.32 |
| 3 | 62.21 | 29.40 | 0.47 |
| 4 | 45.21 | 9.30 | 0.21 |

Purified S. aureus type 5 and type 8 capsular polysaccharides were separately conjugated to CRM197 using a method of the invention (see below).

Depolymerisation

Purified capsular polysaccharide was dissolved in distilled water at 2 mg/mL. Acetic acid was added to a final concentration of 2% (v/v) and the reaction kept at 90° C. for 3 hours (or overnight in the case of Lot B). The solution was then neutralized with 1M NaOH and the depolymerised polysaccharide purified on a gel-filtration column (performed on an Akta™ system (G&E Healthcare) using a S300 Sephacryl™ resin (G&E Healthcare), with a 10 mM NaPi, 10 mM NaCl, pH7.2 mobile phase buffer). The saccharide was detected at 215 nm (FIG. 3). Pooled fractions were dialyzed against distilled water using a 1 kDa membrane (SpectraPor) and lyophilized.

The site of cleavage was verified as being at (1→3) glycosidic linkages within the type 5 polysaccharide using $^1$H NMR. Briefly, samples of native and depolymerised type 5 capsular polysaccharide were freeze-dried to eliminate protonated water solvent and dissolved in deuterium oxide (99.9% deuterium, Sigma-Aldrich). All NMR spectra were recoded at 50° C. on a Bruker Avance III 400 MHz spectrometer using a 5-mm broadband probe and the TopSpin 2.1 software package (Bruker) for data acquisition and processing. 1D $^1$H spectra were collected using a standard one-pulse experiment over a spectral width of 4,000 Hz and collecting 32 k data points. The transmitter was set at the residual HDO frequency (4.79 ppm). The spectra were obtained in a quantitative manner using a total recycle time to ensure a full recovering of each signal (5× Longitudinal Relaxation Time Ti). Spectra were Fourier transformed after applying a 0.2 Hz line broadening function. 2D ($^1$H, $^1$H) scalar correlation spectra were recorded by DQF-COSY pulse sequence. 4096 data points were collected in the F2 domain and 256 in the F1 domain.

1D $^1$H signals for the native polysaccharide were compared with published values and found to be in agreement (Table 2).

between the α-L-FucNAc(3OAc) and β-D-FucNAc residues in the type 5 capsular polysaccharide.

Oxidation

The depolymerised capsular polysaccharide was dissolved in distilled water at 2 mg/mL. NaIO$_4$ was added at a polysaccharide:NaIO$_4$ ratio of 1:1 (weight/weight) and the reaction kept at room temperature for 1-2 hours in the dark. The solution was then dialyzed against distilled water using a 1 kDa membrane (SpectraPor) and lyophilized once again.

Conjugation

Figure 5A:
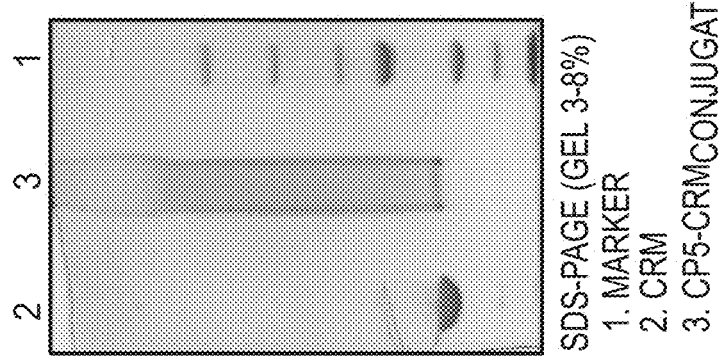
FIG. 5a shows an SDS-PAGE analysis of a S. aureus type 5 capsular polysaccharide-CRM197 conjugate made using a method of the invention.
Figure 5B:
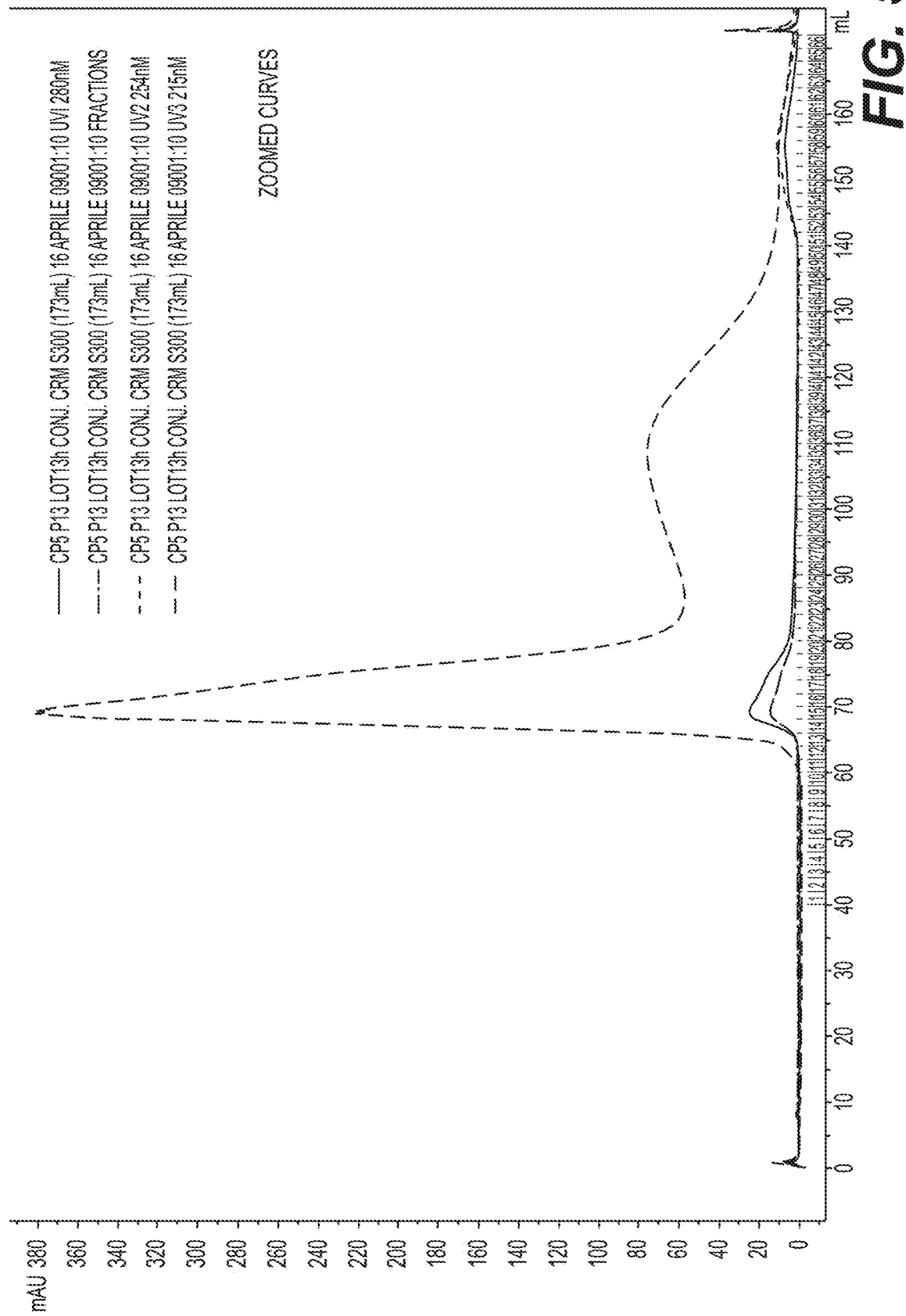
FIG. 5b shows an S300 Sephacryl™ chromatogram of a S. aureus type 5 capsular polysaccharide-CRM197 conjugate made using a method of the invention.

The oxidised capsular polysaccharide was dissolved in a 200 mM NaPi, 1M NaCl, pH7.2 buffer at a concentration of 10 mg/mL. CRM197 was added to the solution at a polysaccharide:protein ratio of 4:1 (weight/weight) and NaBH$_3$CN (Aldrich) added at a saccaaride:NaBCNH$_3$ ratio of 2:1 (weight/weight). The solution was kept at 37° C. for 2 days. SDS-PAGE was used to confirm formation of the conjugate (see FIG. 5a for the type 5 conjugate). After conjugation, the conjugate was purified by gel-filtration chromatography (performed on an Akta™ system (G&E Healthcare) using a S300 Sephacryl™ resin (G&E Healthcare), with a 10 mM NaPi, 10 mM NaCl, pH7.2 mobile phase buffer). The conjugate was detected at 215 nm, 254 nm and 280 nm (see FIG. 5b for the type 5 conjugate). The conjugate solution was stored at −20° C. until further use. Total saccharide in the conjugate was determined by HPAEC-PAD analysis and protein content by MicroBCA assay (see Table 3a for the type 5 conjugate and Table 3b for type 8 conjugate).

TABLE 2

| Signal | Measured δ (ppm)* | Pubd. δ (ppm)** | Pubd. δ (ppm)*** |
|---|---|---|---|
| H$_3$$^{L\text{-}FucNAc\text{-}OAc}$ | 4.958 | 5.005 | 5.005 |
| H$_1$$^{L\text{-}FucNAc\text{-}OAc}$ | 4.929 | 4.981 | 4.975 |
| H$_3$$^{L\text{-}FucNAc\text{-}deOAc}$ | 4.864 | 4.935 | 4.911 |
| H$_1$$^{ManNAc\text{-}deOAc}$ | 4.801 | 4.860 | 4.847 |
| H$_1$$^{ManNAc\text{-}OAc}$ | 4.638 | 4.698 | 4.683 |
| H$_2$$^{ManNAc\text{-}deOAc}$ | 4.625 | 4.680 | 4.670 |
| H$_2$$^{ManNAc\text{-}deOAc}$ | 4.584 | 4.645 | 4.629 |
| H$_1$$^{D\text{-}FucNAc\text{-}OAc/deOAc}$ | 4.405 | 4.461 | 4.452 |
| H$_4$$^{L\text{-}FucNAc\text{-}OAc}$ | 4.320 | 4.382 | 4.367 |
| H$_2$$^{L\text{-}FucNAc\text{-}OAc}$ | 4.292 | 4.368 | 4.338 |
| H$_5$$^{L\text{-}FucNAc\text{-}OAc}$ | 4.121 | 4.175 | 4.168 |
| H$_5$$^{L\text{-}FucNAc\text{-}deOAc}$ | 4.080 | 4.142 | 4.126 |
| H$_2$$^{L\text{-}FucNAc\text{-}deOAc}$ | 4.033 | 4.105 | 4.077 |
| H$_4$$^{L\text{-}FucNAc\text{-}deOAc}$ | 4.005 | 4.060 | 4.051 |
| NAc$^{D\text{-}FucNAc\text{-}OAc}$ | 2.083 | 2.149 | 2.131 |
| NAc$^{D\text{-}FucNAc\text{-}deOAc}$ | 2.067 | 2.126 | 2.115 |
| OAc$^{L\text{-}FucNAc\text{-}OAc}$ | 2.004 | 2.070 | 2.051 |
| NAc$^{L\text{-}FucNAc\text{-}deOAc}$ | 1.995 | 2..057 | 2.002 |
| NAc$^{L\text{-}FucNAc\text{-}OAc}$ | 1.955 | 2.023 | 2.043 |
| NAc$^{ManNAc\text{-}deOAc}$ | 1.948 | 2.018 | 1.996 |
| NAc$^{ManNAc\text{-}OAc}$ | 1.943 | 2.011 | 1.992 |
| H$_6$$^{D\text{-}FucNAc\text{-}OAc}$ | 1.238 | 1.300 | 1.287 |
| H$_6$$^{D\text{-}FucNAc\text{-}deOAc}$ |  | 1.298 |  |
| H$_6$$^{L\text{-}FucNAc\text{-}OAc/deOAc}$ | 1.183 | 1.242 | 1.231 |

Figure 4B:
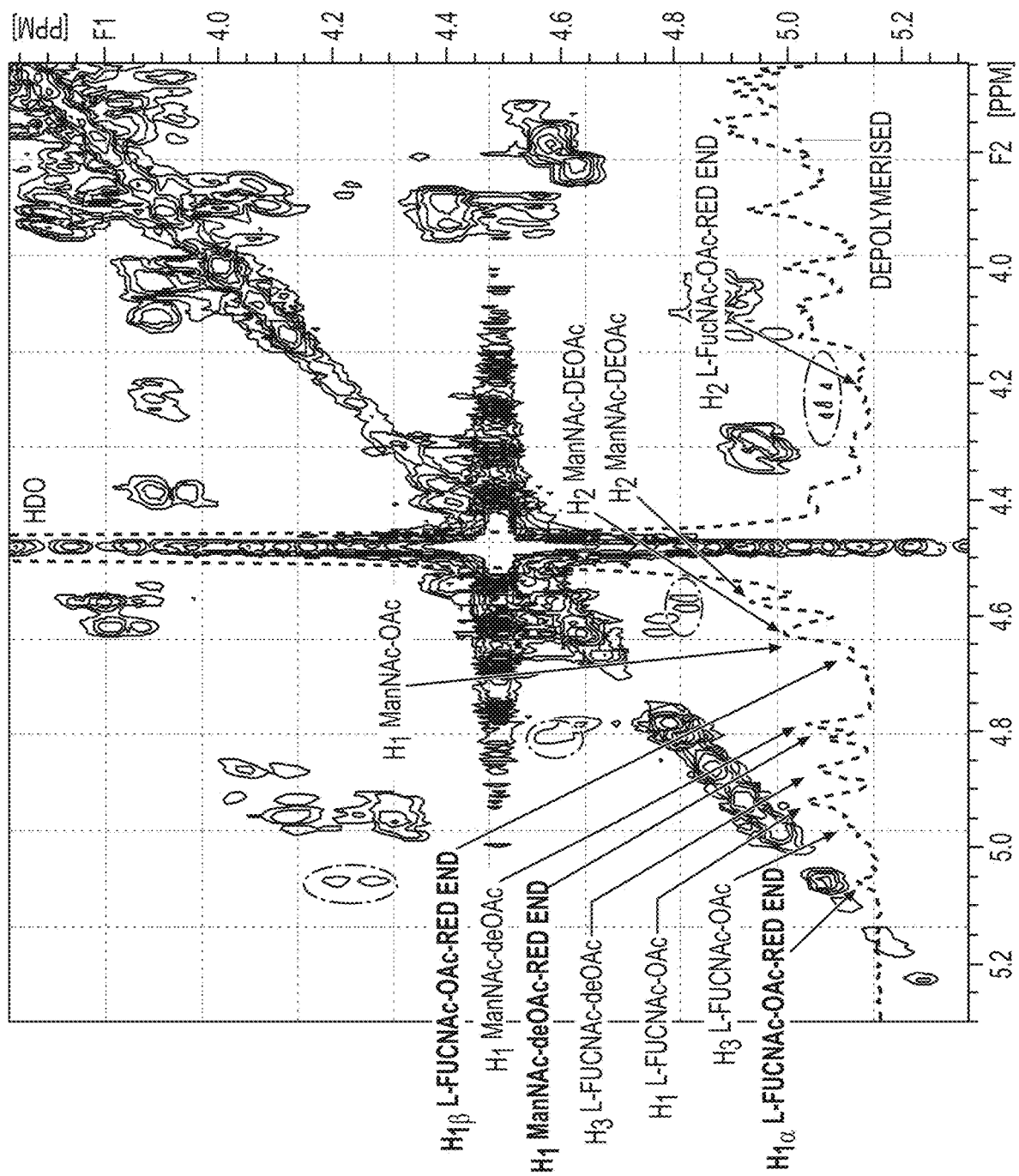
FIGS. 4B and 4C compare the anomeric and Methyl-Fucose regions respectively of 2D ($^1H$, $^1H$) scalar coupling spectra for these polysaccharides. Some notable differences are marked.
Figure 4C:
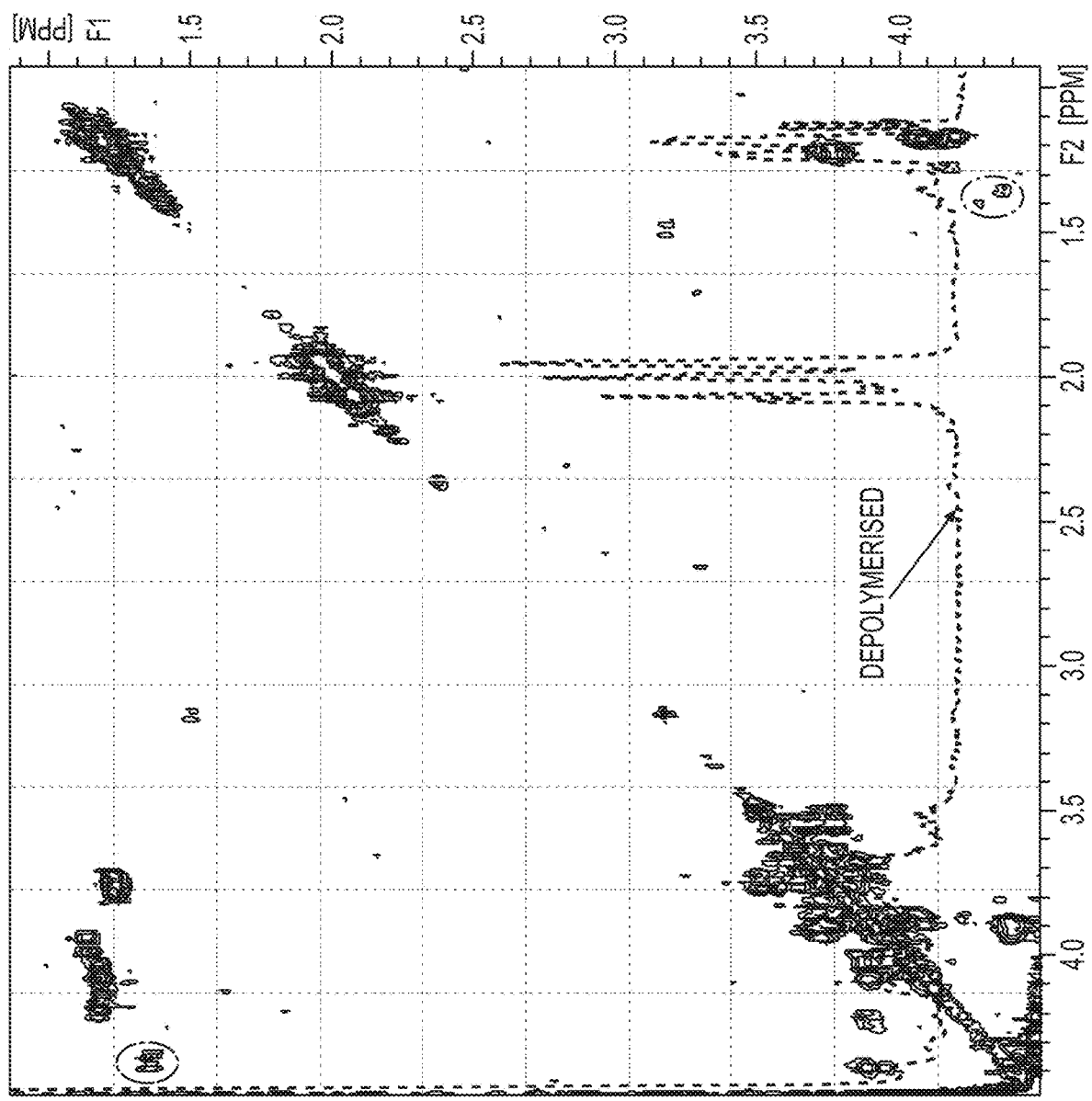

*HDO signal at 4.484 ppm
**Jones C. Carbohydr. Res. 2005, 340(6), 1097-1106 - HDO signal at 4.484 ppm
***Jones C. Carbohydr. Res. 2005, 340(6), 1097-1106 - H1L-FucNAc = 5.005 ppm, therefore HDO signal at 4.532 ppm instead of 4.484 ppm FIG. 4A compares 1D $^1$H signals in the $^1$H anomeric region for the depolymerised and native polysaccharides. FIGS. 4B and 4C compare the anomeric and Methyl-Fucose regions respectively of 2D ($^1$H, $^1$H) scalar coupling spectra for these polysaccharides. The data show that the acetic acid treatment resulted in cleavage of (1-3) glycosidic linkages TABLE 3a

| Conjugate (lot) | Protein (μg/ml) | Saccharide (μg/ml) | Saccharide/protein (w/w) |
|---|---|---|---|
| A | 51.52 | 1.72 | 0.03 |
| B | 161.80 | 17.10 | 0.11 |
| C | 34.42 | 4.22 | 0.12 |
| D | 40.56 | 12.70 | 0.31 |
| E | 196.00 | 55.17 | 0.28 |

TABLE 3b

| Conjugate (lot) | Protein (μg/ml) | Saccharide (μg/ml) | Saccharide/protein (w/w) |
|---|---|---|---|
| α | 518.00 | 82.30 | 0.16 |
| β | 11.00 | 7.94 | 0.72 |
| γ | 23.22 | 5.57 | 0.24 |
| δ | 22.87 | 5.08 | 0.22 |

Purified S. aureus type 5 was conjugated to CRM197 using another method of the invention. In this method, the depolymerisation, oxidation and conjugation steps were carried out as described above, except that the conjugation step was carried out with the derivatised carrier protein described above (CRMadh) instead of CRM197. Total saccharide in the conjugate was determined by HPAEC-PAD analysis and protein content by MicroBCA assay (Table 4).

TABLE 4

| Conjugate (lot) | Protein (μg/ml) | Saccharide (μg/ml) | Saccharide/protein (w/w) |
|---|---|---|---|
| A' | 58.25 | 2.49 | 0.043 |

Alternative Depolymerisation Methods

Figure 6:
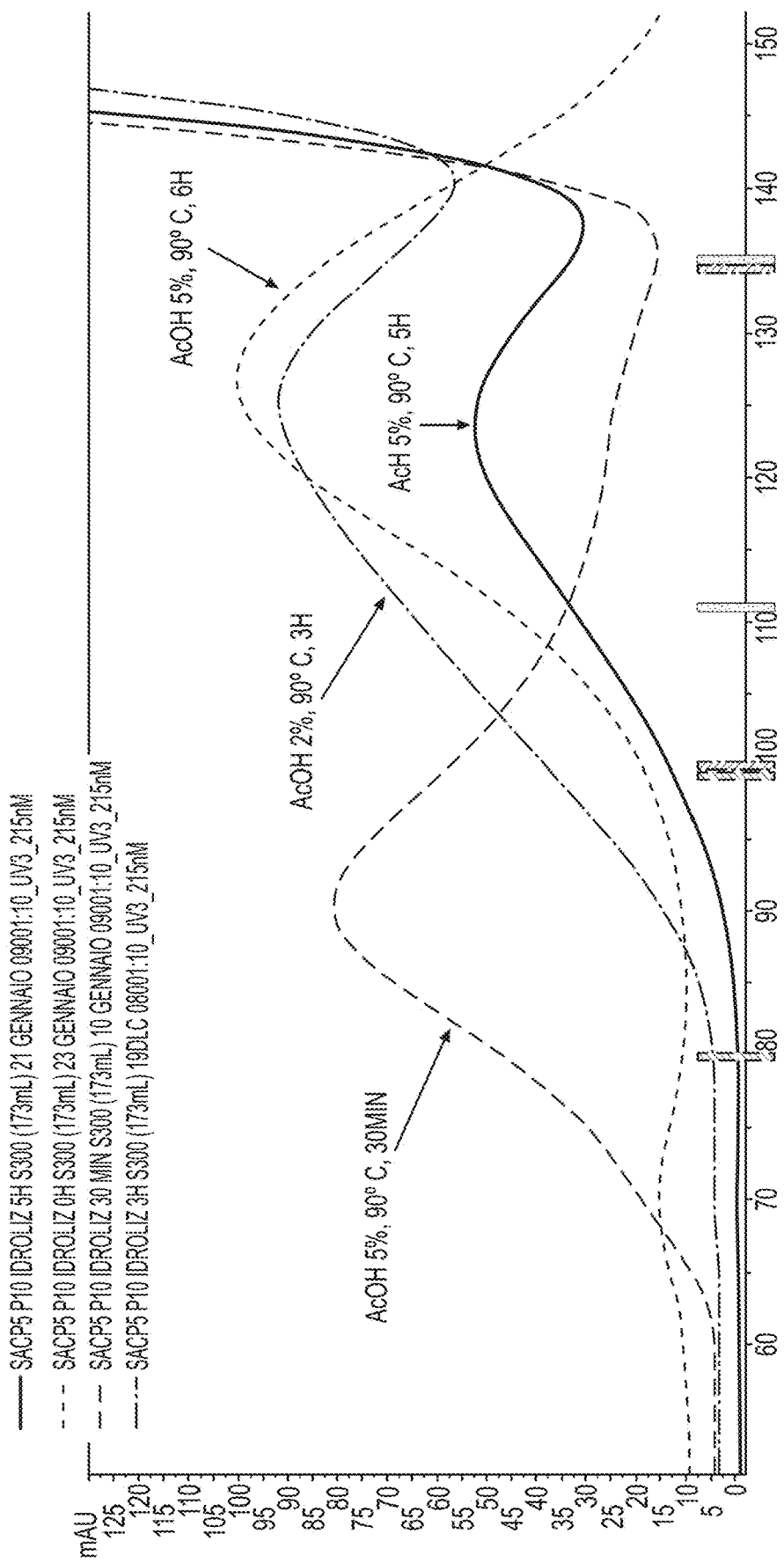
FIG. 6 shows an S300 Sephacryl™ chromatogram of S. aureus type 5 capsular polysaccharides depolymerised under various conditions.

In other studies, different conditions were tested for depolymerisation of the purified capsular polysaccharide. The polysaccharide was dissolved in distilled water at 2 mg/mL. Acetic acid was added to a final concentration of 2% or 5% (v/v) and the reaction kept at 90° C. for 30 minutes, 3 hours, 5 hours or 6 hours. The solution was then neutralized and purified on a gel-filtration column as described above. The saccharide was detected at 215 nm and pooled (FIG. 6).

The pooled fractions were then oxidised and dialyzed against water as described above. The fractions were conjugated to CRM197 or CRMadh as described above and the resultant conjugates purified by gel-filtration chromatography also as described above (FIG. 7).

Figure 17:
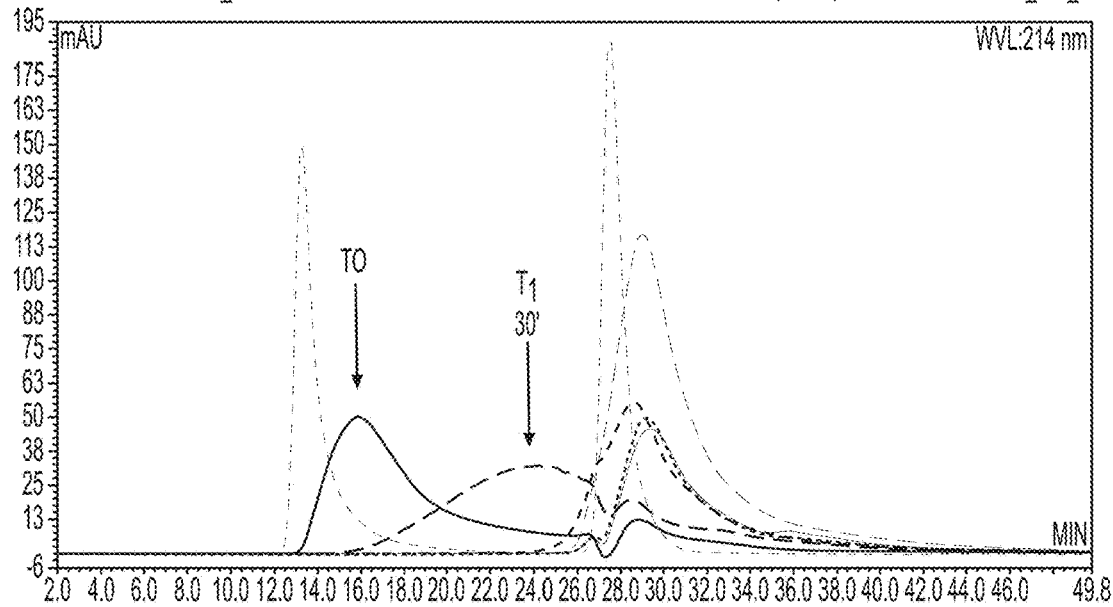
FIG. 17 shows a SEC-HPLC chromatogram of S. aureus type 8 capsular polysaccharide depolymerised with 2M hydrochloric acid.
Figure 18:
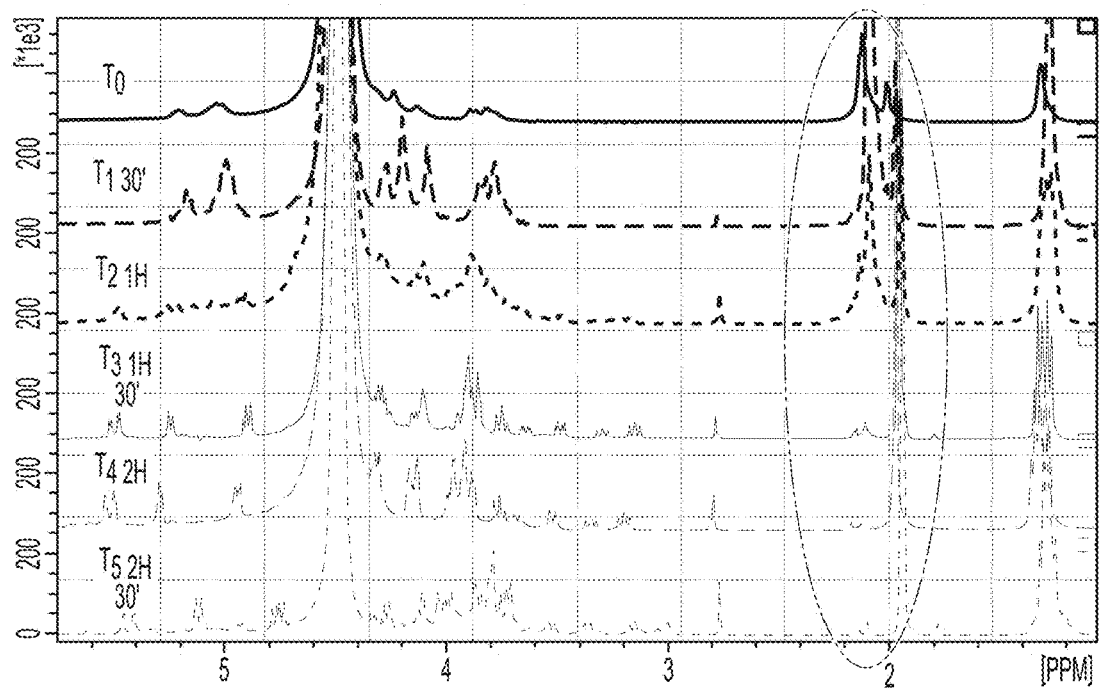
FIG. 18 shows an NMR spectrum of S. aureus type 8 capsular polysaccharide depolymerised with 2M hydrochloric acid.

In another study, hydrochloric acid at 0.5M was used instead of acetic acid for type 8 capsular polysaccharide, and the reaction kept at 90° C. for 2.5 hours, with the reaction being sampled every 30 minutes. Samples were analysed by NMR and SEC-HPLC. The polysaccharide did not hydrolyse and the level of O-acetylation remained almost unchanged. In contrast, when hydrochloric acid at 2M was used, and the reaction kept at 100° C., hydrolysis was observed even after only 30 minutes. The level of O-acetylation gradually fell over the 2.5 hours (FIGS. 17 and 18 (with acetyl peak circled)).

Immunisation Study—Abscess Model (1)

General assay protocol: Mice were immunized according to the schedule described below and challenged by intravenous injection of a bacterial suspension of *S. aureus*. The culture of *S. aureus* was centrifuged, washed twice and diluted in PBS before challenge. Further dilutions were needed for the desired inoculum, which was experimentally verified by agar plating and colony formation. For organ harvest, mice were euthanized and their kidneys removed and homogenized in 1% TRITON X-100™. Aliquots were then diluted and plated on agar media for triplicate determination of CFU. For histology, kidney tissue was incubated at room temperature in 10% formalin for 24 hours. Tissues were embedded in paraffin, thin sectioned, hematoxylin/eosin stained and examined by microscopy.

Figure 8:
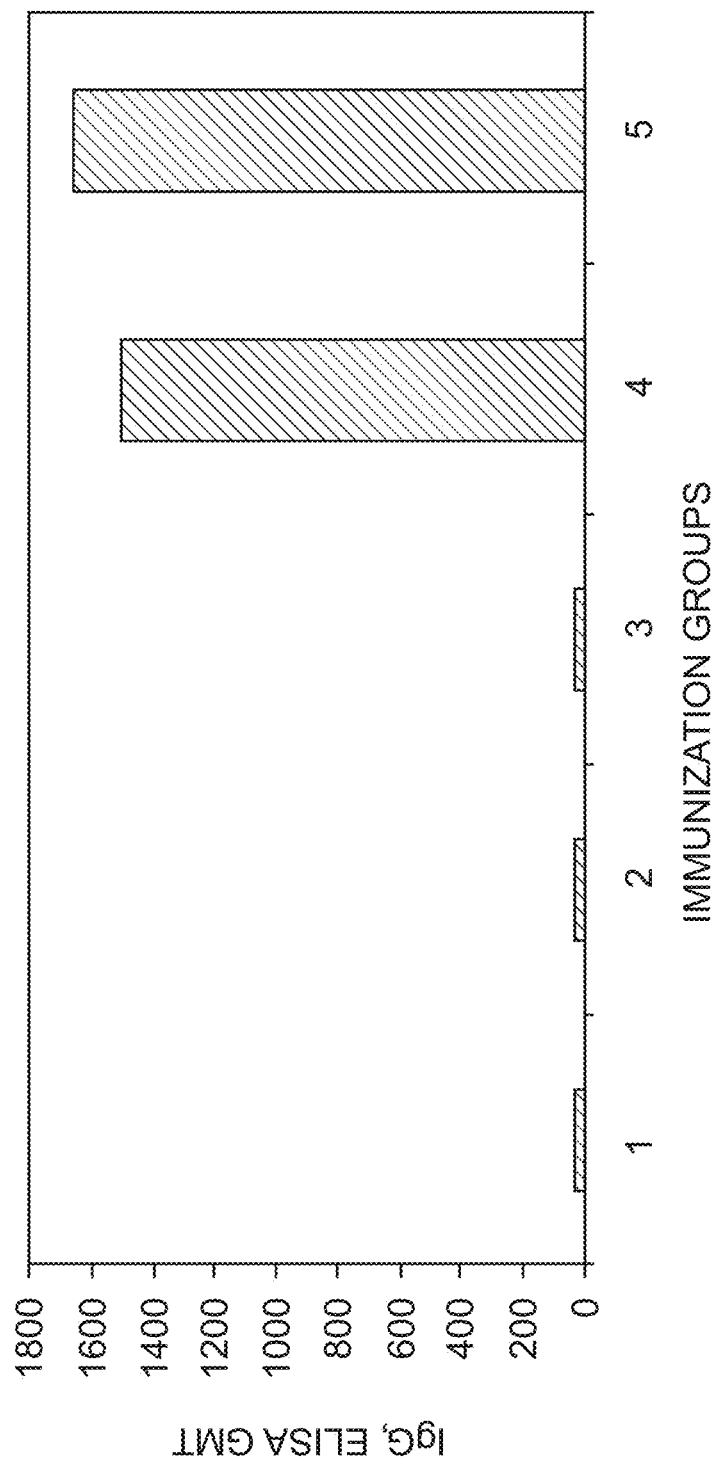
FIG. 8 shows the IgG response to various antigens in a mouse kidney abscess model of S. aureus infection.
Figure 9:
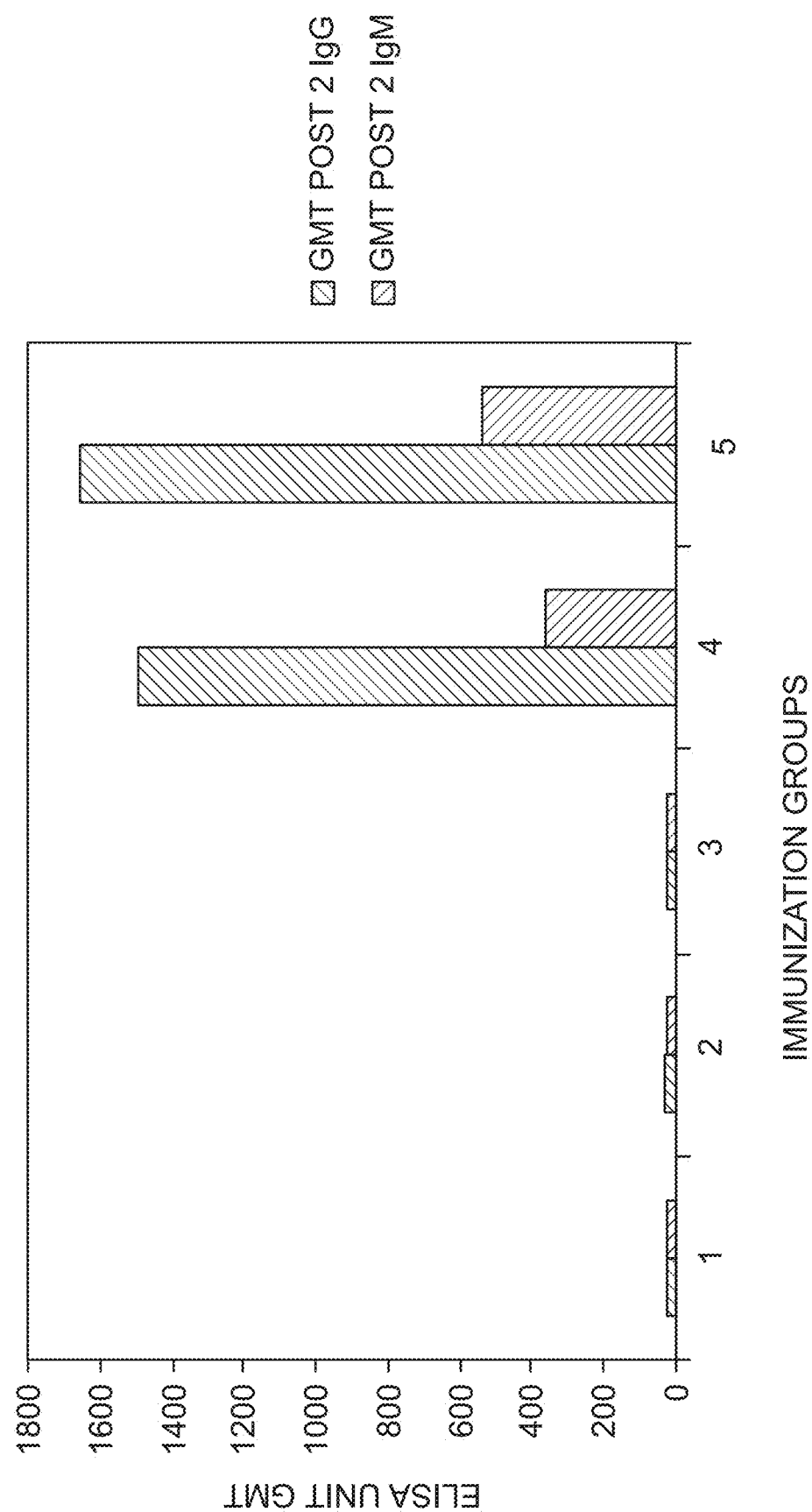
FIG. 9 compares IgG and IgM responses to various antigens in the mouse kidney abscess model.
Figure 10:
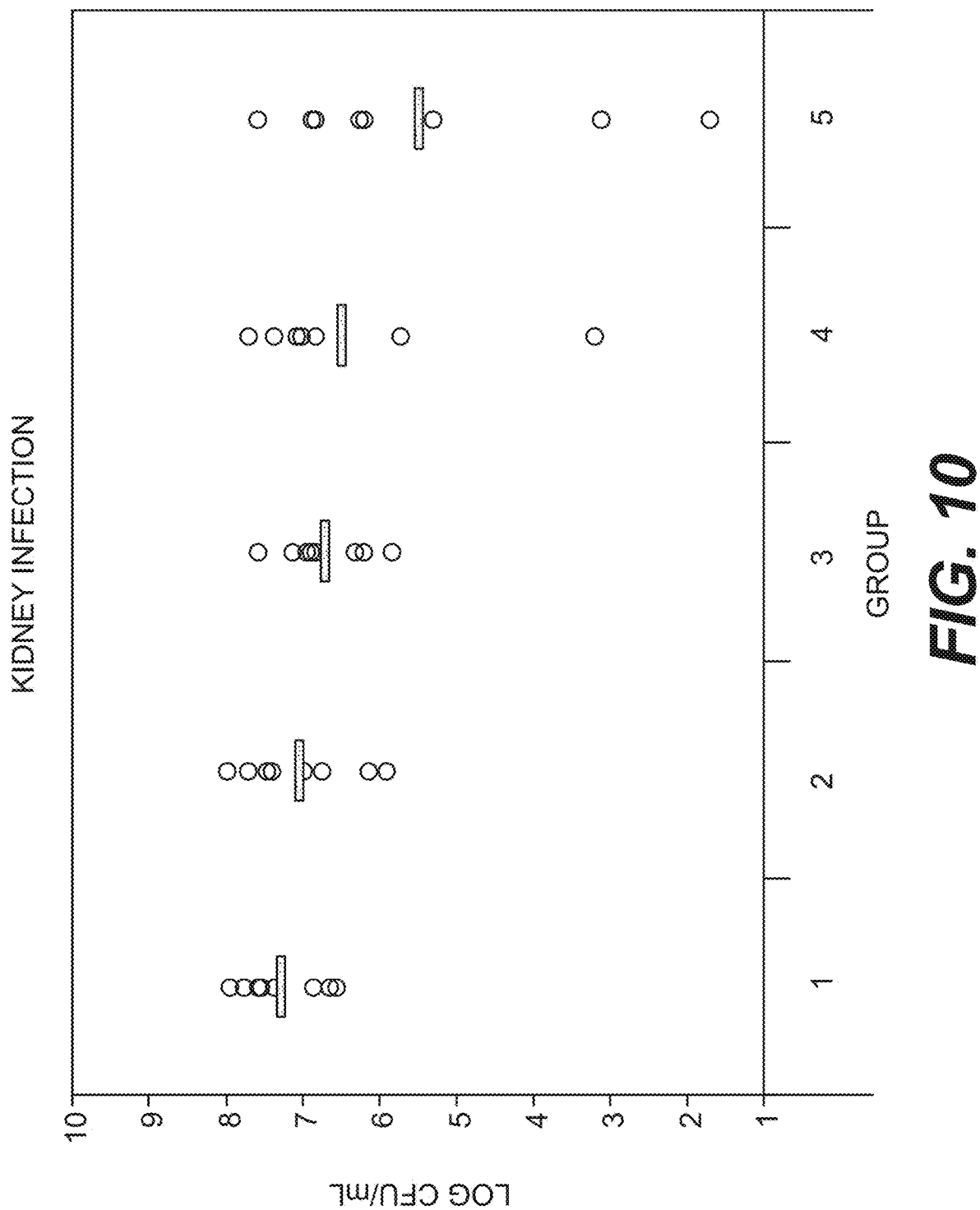
FIG. 10 shows protective responses to various antigens in the mouse kidney abscess model.

CD1 mice at 3 weeks old were immunised at days 0 and 11 by intraperitoneal injection with a 5 µg dose of antigen in an injection volume of 200 µl. The mice were bled on days 0 and 20 and challenged with *S. aureus* on day 21. Organs were harvested at day 25. Immunisations were carried out in groups of eight mice according to the following scheme:
  Group 1—Alum alone
  Group 2—Type 5 capsular polysaccharide alone
  Group 3—Type 5 capsular polysaccharide plus alum
  Group 4—Type 5 capsular polysaccharide-CRMadh conjugate (Lot 1)
  Group 5—Type 5 capsular polysaccharide-CRMadh conjugate (Lot 1) plus alum The conjugate induced a specific IgG response against type 5 polysaccharide. The alum formulation gave an improved response (FIG. 8). The conjugate also induced a specific IgM response against type 5 polysaccharide (FIG. 9). The alum conjugate formulation also gave the best protection from kidney infection (FIG. 10).

Immunisation Study—Abscess Model (2)

Figure 11:
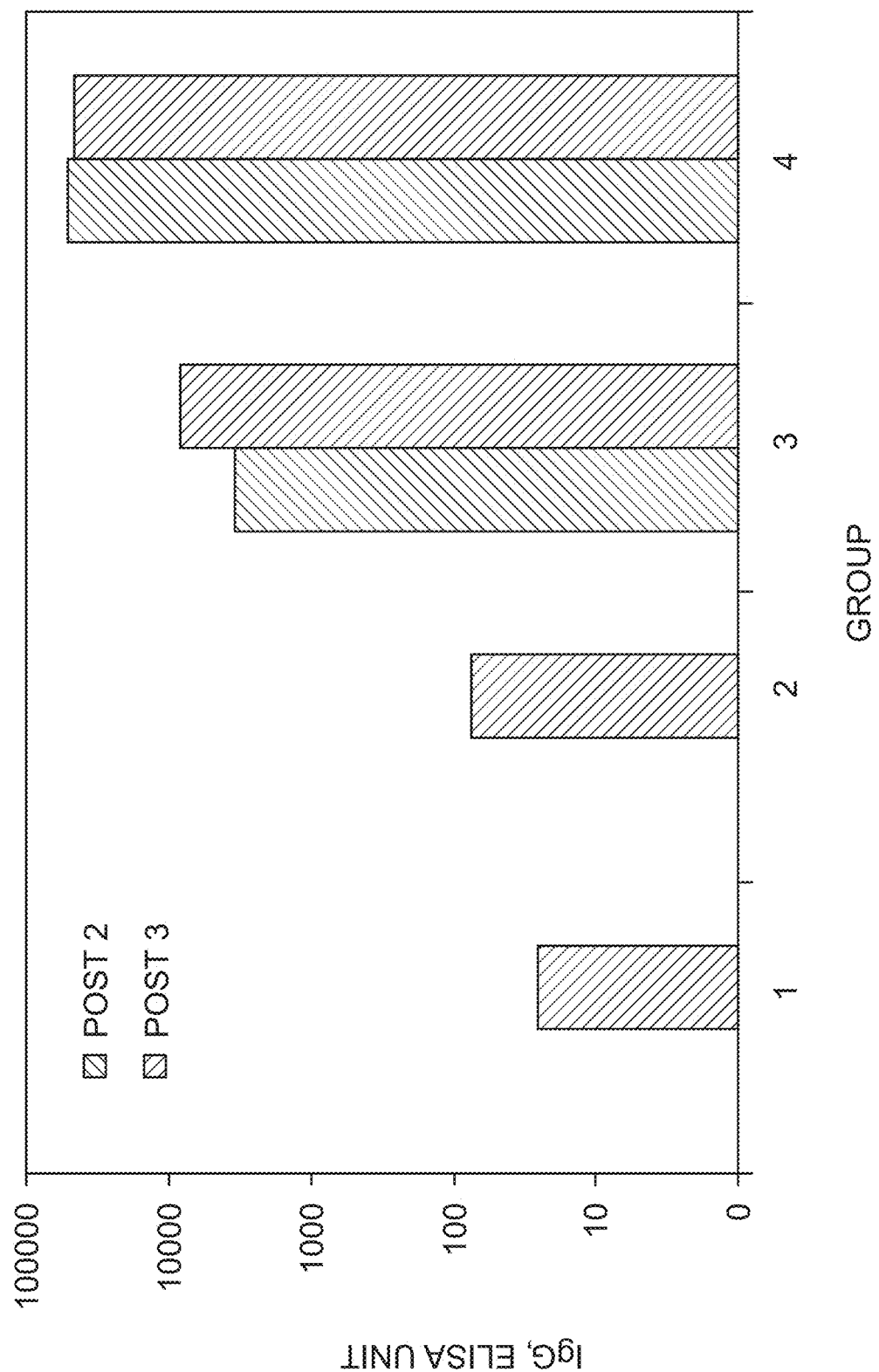
FIG. 11 compares the IgG response to different conjugates in the mouse kidney abscess model.
Figure 12:
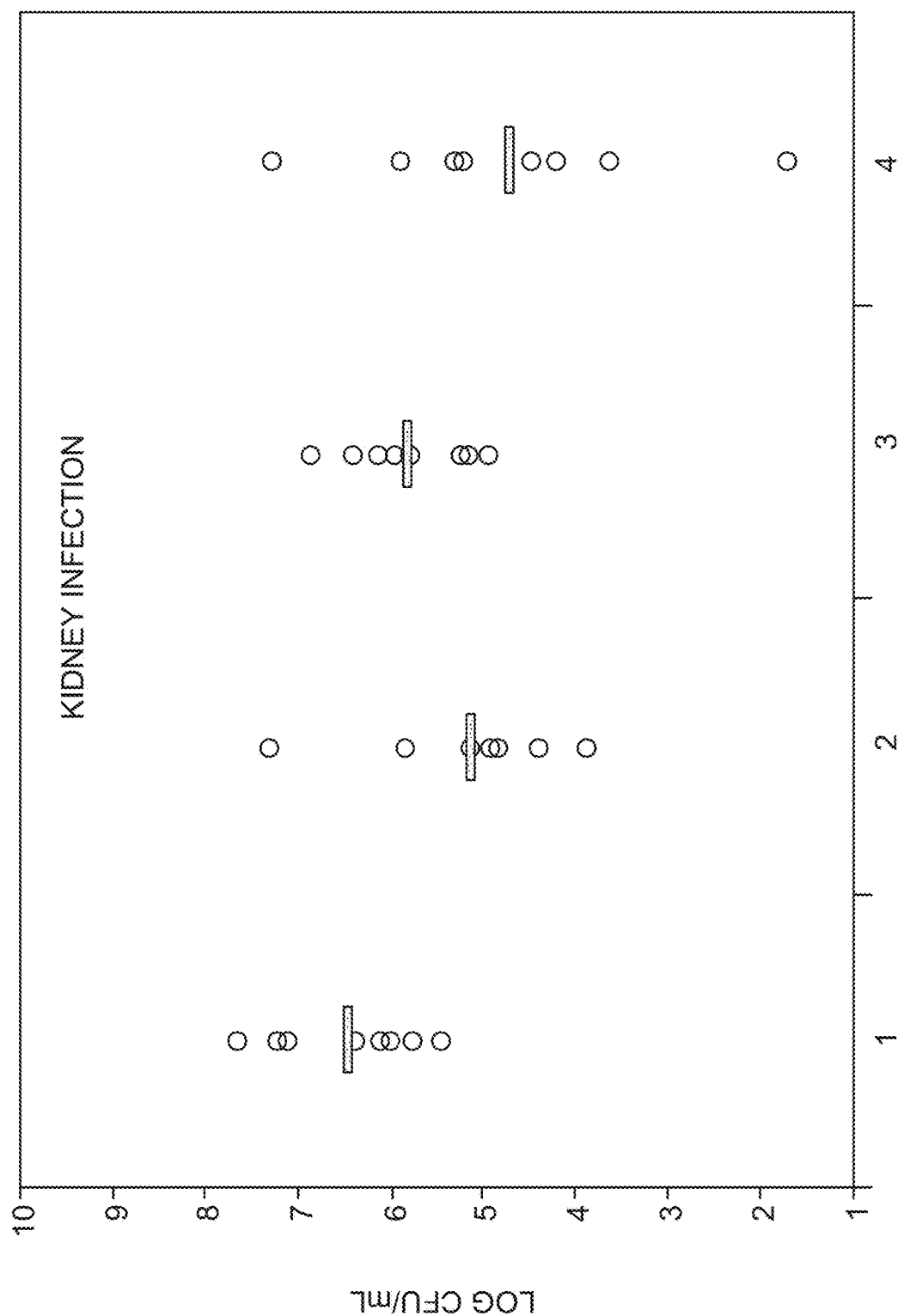
FIG. 12 compares protective responses to different conjugates in the mouse kidney abscess model.

CD1 mice at 3 weeks old were immunised at days 1, 14 and 28 by intraperitoneal injection with a 5 µg dose of antigen in an injection volume of 200 µl. The mice were bled on days 0, 27 and 37 and challenged with *S. aureus* on day 38. Organs were harvested at day 42. Immunisations were carried out in groups of eight mice according to the following scheme:
  Group 1—Alum alone
  Group 2—Type 5 capsular polysaccharide plus alum
  Group 3—Type 5 capsular polysaccharide-CRMadh conjugate (Lot 2) plus alum
  Group 4—Type 5 capsular polysaccharide-CRMadh conjugate (Lot A') plus alum The conjugates induced a specific IgG response against type 5 polysaccharide. The conjugates of the invention (represented by lot A') gave a particularly high titre (FIG. 11). The conjugates of the invention gave the best protection from kidney infection (FIG. 12).

Immunisation Study—Abscess Model (3)

Figure 13A:
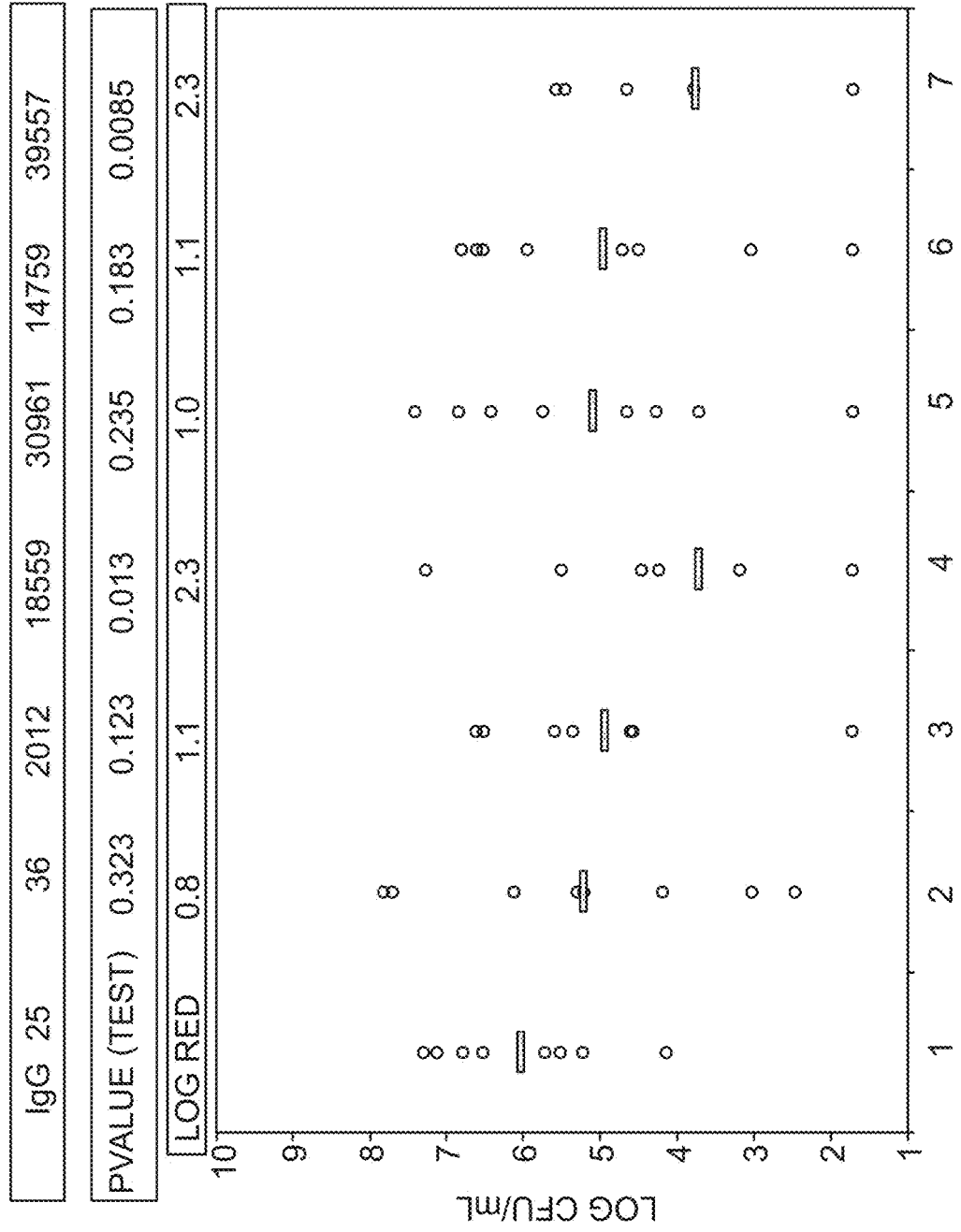
FIGS. 13A and 13B compare protective responses to further conjugates in the mouse kidney abscess model.
Figure 13B:
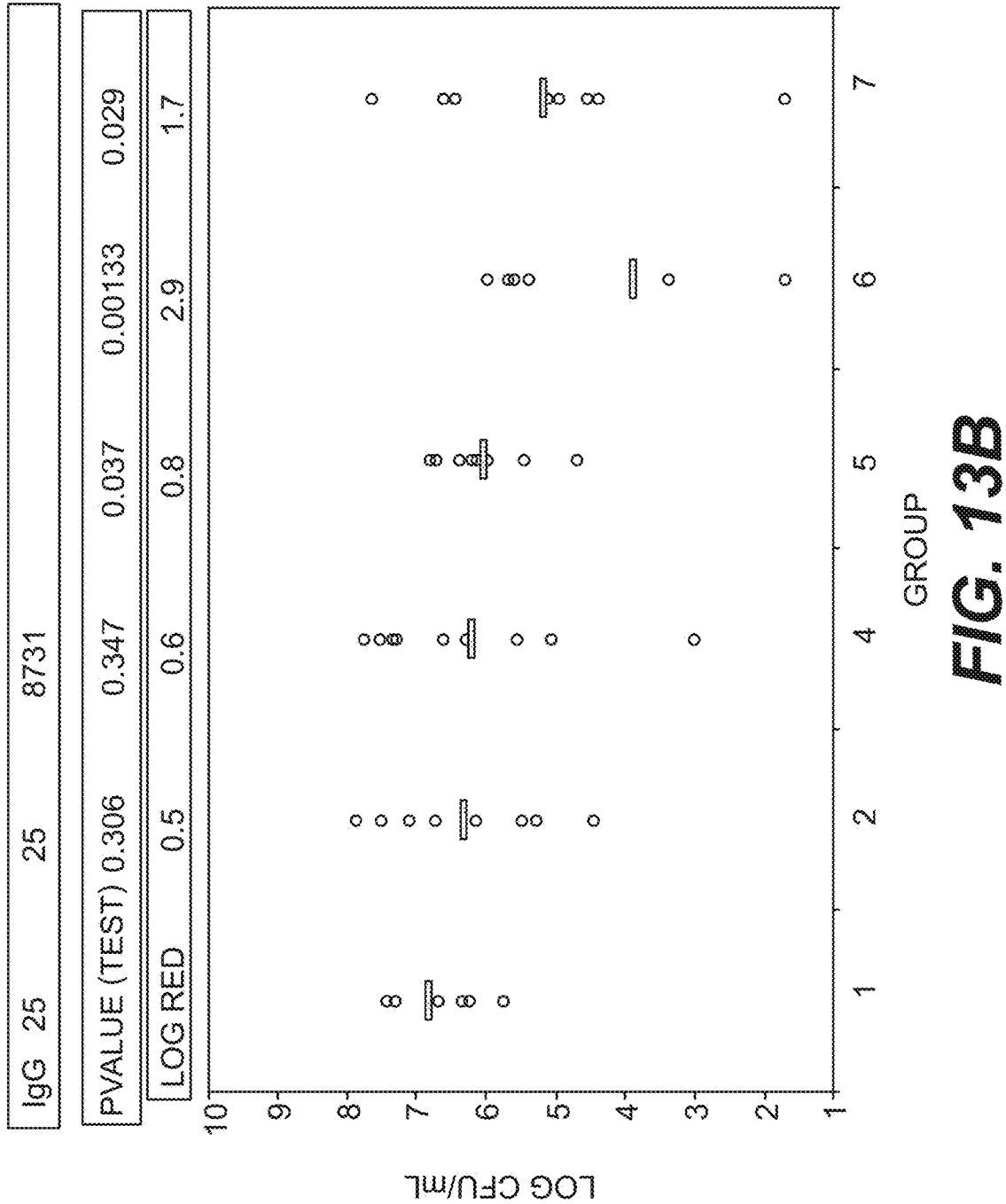
Figure 14:
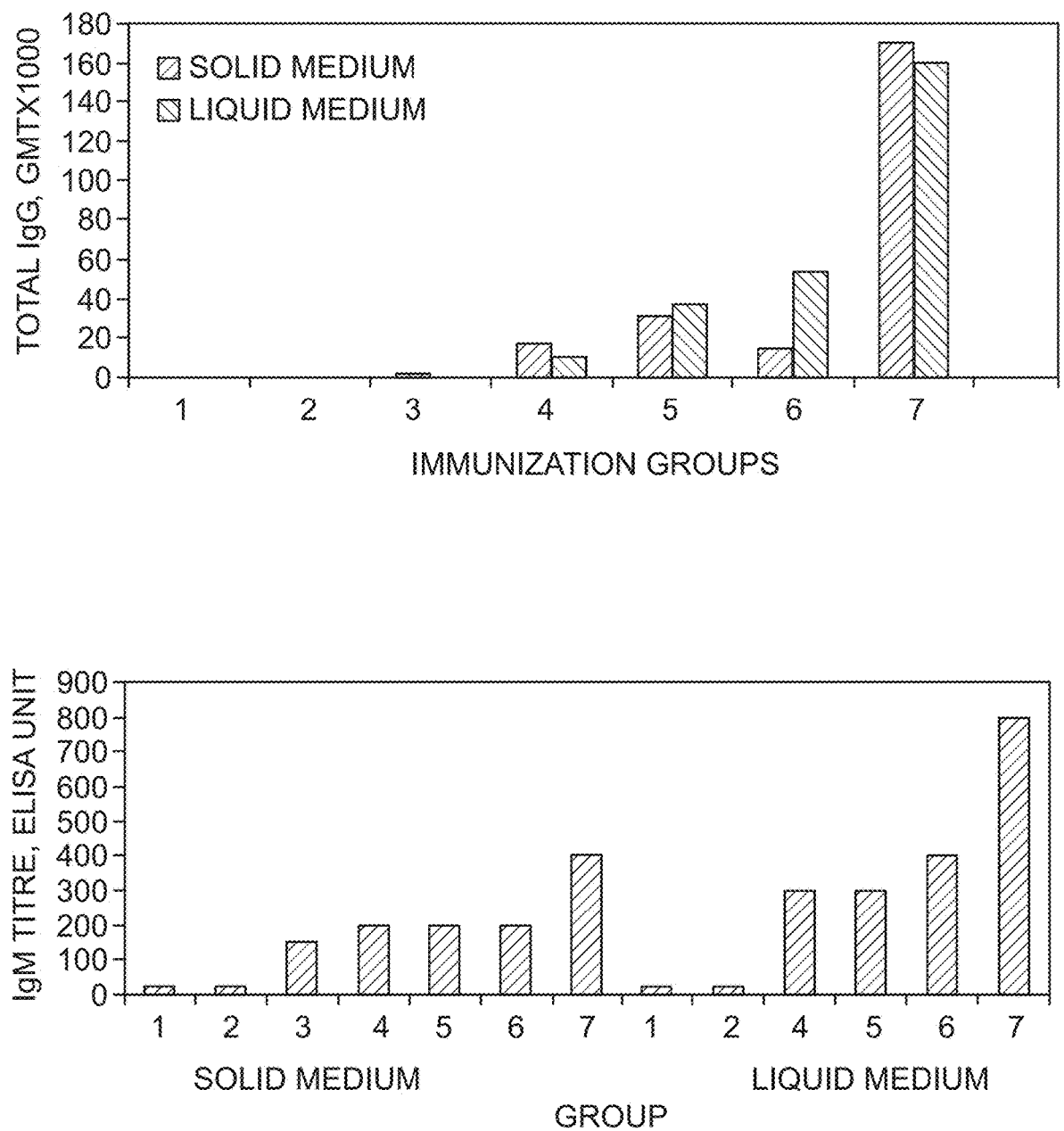
FIG. 14 compares IgG and IgM responses to further conjugates in the mouse kidney abscess model.

CD1 mice at 3 weeks old were immunised at days 1, 14 and 28 by intraperitoneal injection with a 5 µg dose (or 0.5 µg dose in the case of lot A) of antigen in an injection volume of 200 µl. The mice were bled on days 0, 27 and 37 and challenged with *S. aureus* (grown in liquid or solid medium) on day 38. Organs were harvested at day 42. Immunisations were carried out in groups of eight mice according to the following scheme:
  Group 1—Alum alone
  Group 2—Type 5 capsular polysaccharide plus alum
  Group 3—Type 5 capsular polysaccharide-CRMadh conjugate (Lot 2) plus alum
  Group 4—Type 5 capsular polysaccharide-CRMadh conjugate (Lot 3) plus alum
  Group 5—Type 5 capsular polysaccharide-CRMadh conjugate (Lot A') plus alum
  Group 6—Type 5 capsular polysaccharide-CRM conjugate (Lot A) plus alum
  Group 7—Type 5 capsular polysaccharide-CRM conjugate (Lot B) plus alum The conjugates of the invention (represented by lots A', A and B) gave protection from kidney infection (FIGS. 13A and 13B). The conjugates of the invention gave high titres of specific IgG antibodies with low tites of IgM antibodies (FIG. 14).

Immunisation Study—Abscess Model (4)

Figure 15:
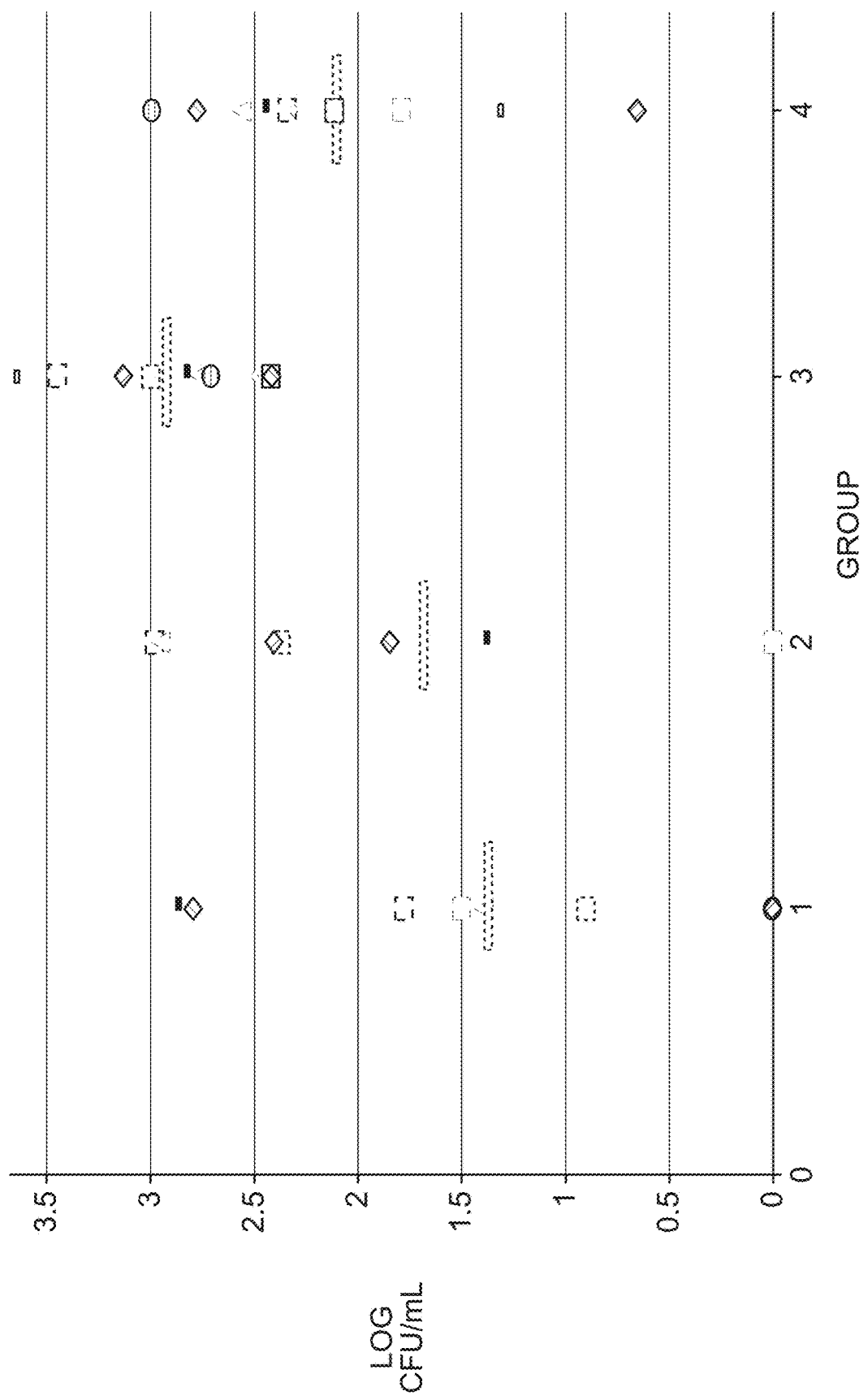
FIG. 15 compares protective responses to a further conjugate when adjuvanted with different agents in the mouse kidney abscess model.

CD1 mice at 3 weeks old were immunised at days 1 and 14 by intraperitoneal injection with a 1 µg dose of antigen in an injection volume of 200 µl. The mice were bled on days 0, 13 and 27 and challenged with *S. aureus* on day 28. Organs were harvested at day 32. Immunisations were carried out in groups of eight or nine mice according to the following scheme:
  Group 1—Type 8 capsular polysaccharide-CRM conjugate (lot α) plus alum
  Group 2—Type 8 capsular polysaccharide-CRM conjugate (lot α) plus MF59
  Group 3—Alum alone
  Group 4—MF59 alone The conjugates of the invention gave protection from kidney infection (FIG. 15). The alum formulation gave better protection than the MF59 formulation.

Immunisation Study—Lethal Model (1)

General Assay Protocol:

Mice were immunized according to the schedule described below and challenged by intraperitoneal injection of a bacterial suspension of *S. aureus*. Cultures of *S. aureus* were centrifuged, washed twice and diluted in PBS before challenge. Further dilutions were needed for the desired inoculum, which was experimentally verified by agar plating and colony formation. Animals were monitored for 14 days and lethal disease recorded.

CD1 mice were immunised by intraperitoneal injection with a 5 μg dose of antigen in an injection volume of 200 μl. Immunisations were carried out in groups of twelve mice according to the following scheme, prior to challenge with 5×10$^8$ CFU type 5 *S. aureus*:

Group 1—PBS plus alum
Group 2—Type 5 capsular polysaccharide-CRM conjugate (Lot C) plus alum
Group 3—Type 5 capsular polysaccharide-CRMadh conjugate (Lot 3) plus alum
Group 1—PBS plus alum
Group 2—Type 5 capsular polysaccharide-CRM conjugate (lot E) plus EsxAB, Sta006 and Sta011 proteins and alum
Group 3—Type 5 capsular polysaccharide-CRM conjugate (lot E) and Type 8 capsular polysaccharide-CRM conjugate (lot 13) plus EsxAB, Sta006 and Sta011 proteins and alum
Group 4—Type 5 capsular polysaccharide-CRM conjugate (lot E) and Type 8 capsular polysaccharide-CRM conjugate (lot 13) plus EsxAB, Sta011 and Sta073 proteins and alum Survival data is presented in Table 7.

TABLE 7

| Group | Time (days) | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| 1 | 100 | 50 | 42 | 42 | 42 | 42 | 42 | 42 | 42 | 42 | 33 | 33 | 33 | 33 |
| 2 | 100 | 42 | 42 | 42 | 42 | 42 | 42 | 42 | 42 | 42 | 33 | 33 | 33 | 33 |
| 3 | 100 | 75 | 75 | 75 | 75 | 75 | 75 | 75 | 75 | 75 | 58 | 50 | 50 | 50 |
| 4 | 100 | 92 | 92 | 83 | 83 | 83 | 83 | 83 | 83 | 83 | 75 | 75 | 75 | 75 |

Figure 16:
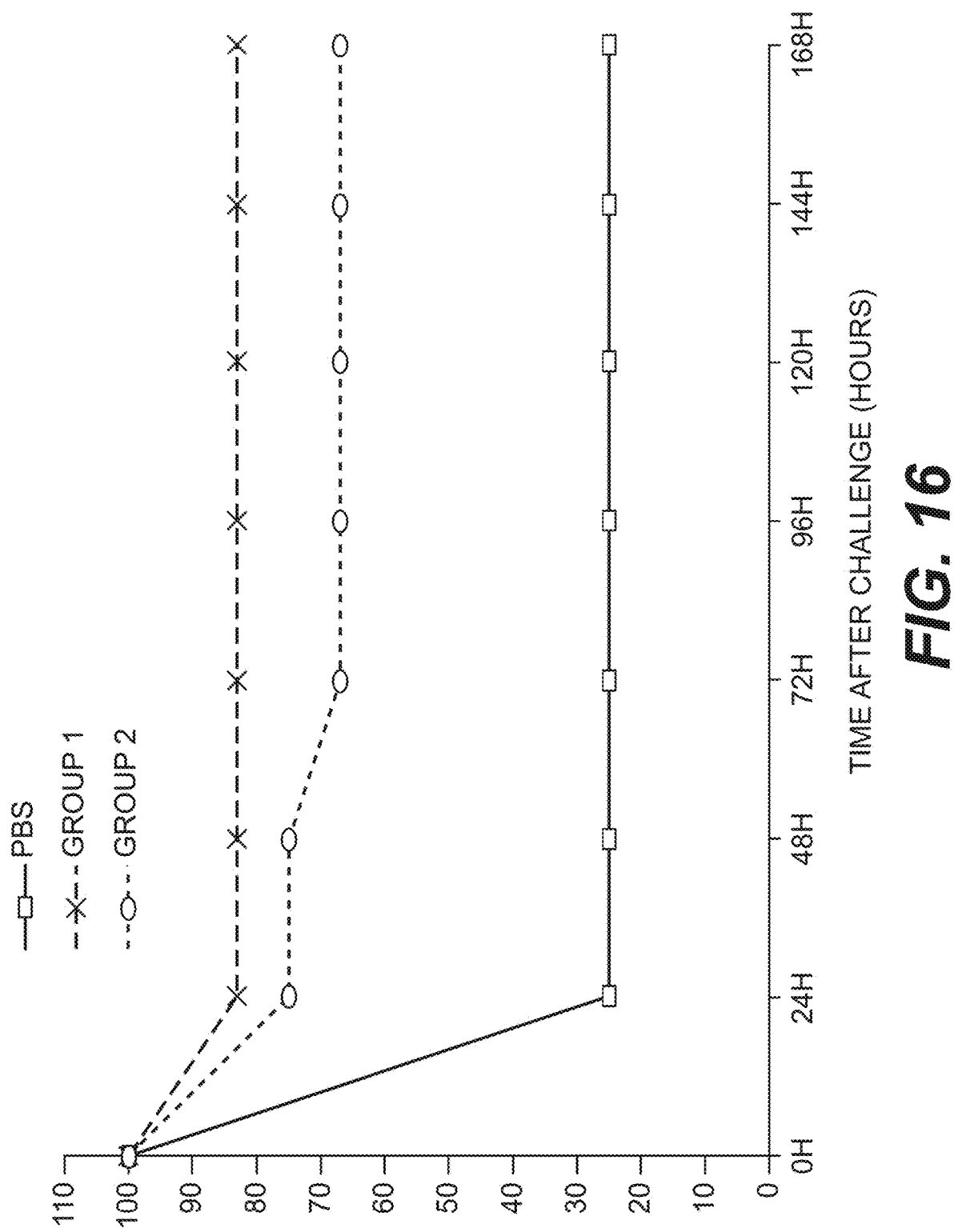
FIG. 16 compares responses to various antigens in a mouse lethal model of S. aureus infection.

The conjugates of the invention (represented by lot C) gave higher survival (FIG. 16).

Immunisation Study—Lethal Model (2)

CD1 mice were immunised by intraperitoneal injection with a 2 μg (saccharide) and 10 g (protein, where present) doses of antigen in an injection volume of 200 μl. Immunisations were carried out in groups of twelve mice according to the following scheme, prior to challenge with 5×10$^8$ CFU type 5 *S. aureus*:

Group 1—PBS plus alum
Group 2—Type 5 capsular polysaccharide-CRM conjugate (Lot D) plus alum
Group 3—Type 5 capsular polysaccharide-CRMadh conjugate (Lot 4) plus alum
Group 4—Type 5 capsular polysaccharide-CRM conjugate (Lot D) plus EsxAB, Sta006 and Sta011 proteins and alum
Group 5—Type 5 capsular polysaccharide-CRM conjugate (Lot D) plus HlaH35L, Sta006 and Sta011 proteins and alum Survival data is presented in Table 5.

TABLE 5

| Group | Time (days) | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| 1 | 100 | 25 | 17 | 17 | 17 | 17 | 17 | 17 | 17 | 17 | 8 | 0 | 0 | 0 |
| 2 | 100 | 50 | 50 | 50 | 50 | 50 | 50 | 50 | 50 | 42 | 42 | 42 | 42 | 42 |
| 3 | 100 | 50 | 42 | 42 | 42 | 42 | 42 | 42 | 42 | 33 | 33 | 33 | 33 | 33 |
| 4 | 100 | 67 | 67 | 67 | 67 | 67 | 67 | 67 | 67 | 67 | 67 | 67 | 67 | 67 |
| 5 | 100 | 100 | 100 | 100 | 100 | 100 | 83 | 83 | 75 | 75 | 75 | 75 | 75 | 75 |

The conjugates of the invention (represented by lot D) gave higher survival. Survival was enhanced by addition of *S. aureus* protein antigens.

Immunisation Study—Lethal Model (3)

CD1 mice were immunised by intraperitoneal injection with a 2 μg (type 5 polysaccharide) 1 μg (type 8 polysaccharide, where present) and 10 g (protein, where present) doses of antigen in an injection volume of 200 μl. Immunisations were carried out in groups of twelve mice according to the following scheme, prior to challenge with 5×10$^8$ CFU type 5 *S. aureus*:

Immunisation Study—Lethal Model (4)

CD1 mice were immunised by intraperitoneal injection with a 2 μg (type 5 capsular polysaccharide) 1 μg (type 8 capsular polysaccharide, where present) and 10 g (protein, where present) doses of antigen in an injection volume of 200 μl. Immunisations were carried out in groups of twelve mice according to the following scheme, prior to challenge with 5×10$^8$ CFU type 5 *S. aureus*:

Group 1—PBS plus alum
Group 2—Type 5 capsular polysaccharide-CRM conjugate (lot E) and Type 8 capsular polysaccharide-CRM conjugate (lot γ first dose, lot δ second dose) plus EsxAB, Sta006 and Sta011 proteins and alum
Group 3—Type 5 capsular polysaccharide-CRM conjugate (lot E) and Type 8 capsular polysaccharide-CRM conjugate (lot γ first dose, lot δ second dose) plus alum
Group 4—Type 5 capsular polysaccharide-CRM conjugate (lot E) and Type 8 capsular polysaccharide-CRM conjugate (lot γ first dose, lot δ second dose) plus EsxAB protein and alum
Group 5—Type 5 capsular polysaccharide-CRM conjugate (lot E) and Type 8 capsular polysaccharide-CRM conjugate (lot γ first dose, lot δ second dose) plus Sta006 protein and alum
Group 6—Type 5 capsular polysaccharide-CRM conjugate (lot E) and Type 8 capsular polysaccharide-CRM conjugate (lot γ first dose, lot δ second dose) plus Sta011 protein and alum
Group 7—Type 5 capsular polysaccharide-CRM conjugate (lot E) and Type 8 capsular polysaccharide-CRM conjugate (lot γ first dose, lot δ second dose) plus Sta006 and Sta011 proteins and alum Group 8—Type 5 capsular polysaccharide-CRM conjugate (lot E) plus HlaH35L, Sta006 and Sta011 proteins and alum Group 9—Type 5 capsular polysaccharide-CRM conjugate (lot E) plus HlaH35L protein and alum Survival data is presented in Table 8.

TABLE 8

| Group | Time (days) | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| 1 | 100 | 100 | 13 | 13 | 13 | 13 | 13 | 13 | 13 | 13 | 13 | 13 | 13 | 13 |
| 2 | 100 | 88 | 75 | 75 | 63 | 63 | 63 | 50 | 50 | 50 | 50 | 50 | 50 | 50 |
| 3 | 100 | 100 | 63 | 63 | 38 | 38 | 38 | 38 | 38 | 38 | 38 | 38 | 38 | 38 |
| 4 | 100 | 100 | 75 | 75 | 75 | 75 | 75 | 75 | 63 | 50 | 50 | 25 | 25 | 25 |
| 5 | 100 | 100 | 50 | 50 | 50 | 50 | 50 | 38 | 38 | 38 | 38 | 38 | 38 | 38 |
| 6 | 100 | 100 | 25 | 25 | 25 | 25 | 25 | 25 | 25 | 25 | 25 | 13 | 13 | 13 |
| 7 | 100 | 88 | 63 | 63 | 63 | 63 | 63 | 50 | 50 | 50 | 50 | 50 | 50 | 50 |
| 8 | 100 | 100 | 100 | 100 | 88 | 88 | 88 | 88 | 88 | 75 | 75 | 75 | 75 | 75 |
| 9 | 100 | 88 | 88 | 63 | 38 | 38 | 38 | 38 | 38 | 13 | 13 | 13 | 13 | 13 |

It will be understood that the invention has been described by way of example only and modifications may be made whilst remaining within the scope and spirit of the invention.

REFERENCES

[1] Fattom et al. (1990) *Infect Immun.* 58(7):2367-74.
[2] Fattom et al. (1992) *Infect Immun.* 60(2):584-9.
[3] Fattom et al. (1993) *Infect Immun.* 61(3):1023-32.
[4] Fattom et al. (1996) *Infect Immun.* 64(5):1659-65.
[5] Welch et al. (1996) *J Am Soc Nephrol.* 7(2):247-53.
[6] Fattom et al. (1998) *Infect Immun.* 66(10):4588-92.
[7] Fattom et al. (1993) *Vaccine* 17(2):126-33.
[8] Fattom et al. (2002) *N Engl J Med.* 346(7):491-6.
[9] Robbins et al. (2005) *Ann N Y Acad Sci.* 754:68-82.
[10] Reynaud-Rondier et al. (1991) *FEMS Microbiology Immunology* 76:193-200.
[11] Tollersrud et al. (2001) *Vaccine.* 19(28-29):3896-903.
[12] WO03/061558.
[13] Gilbert et al. (1994) *Vaccine.* 12(4):369-74.
[14] Moreau et al. (1990) *Carbohydrate Res.* 339(5):285-91
[15] Fournier et al. (1984) *Infect. Immun.* 45(1):87-93.
[16] Jones (2005) *Carbohydrate Res.* 340(6):1097-106.
[17] Lemercinier and Jones (1996) *Carbohydrate Res.* 296: 83-96.
[18] Jones and Lemercinier (2002) *J Pharm Biomed Anal.* 30(4):1233-47.
[19] WO05/033148
[20] WO 00/56357
[21] Hestrin (1949) *J. Biol. Chem.* 180:249-261.
[22] Konadu et al. (1994) *Infect. Immun.* 62:5048-5054.
[23] Gilbert et al. (1994) *J. Microb. Meth.* 20:39-46.
[24] US patent application 61/256,905 'PURIFICATION OF STAPHYLOCOCCUS AUREUS TYPE 5 AND TYPE 8 CAPSULAR SACCHARIDES' (NOVARTIS AG). Assignee reference no. 53615-US-PSP.
[25] Ramsay et al. (2001) *Lancet* 357(9251):195-196.
[26] Lindberg (1999) *Vaccine* 17 Suppl 2:S28-36.
[27] Buttery & Moxon (2000) *J R Coll Physicians Lond* 34:163-168.
[28] Ahmad & Chapnick (1999) *Infect Dis Clin North Am* 13:113-33, vii.
[29] Goldblatt (1998) *J. Med. Microbiol.* 47:563-567.
[30] European patent 0477508.
[31] U.S. Pat. No. 5,306,492.
[32] WO98/42721.
[33] Dick et al. in *Conjugate Vaccines* (eds. Cruse et al.) Karger, Basel, 1989, 10:48-114.
[34] Hermanson *Bioconjugate Techniques*, Academic Press, San Diego (1996) ISBN: 0123423368.
[35] *Research Disclosure*, 453077 (January 2002)
[36] Herbelin et al. (1997) *J Dairy Sci.* 80(9):2025-34.
[37] EP-A-0372501.
[38] EP-A-0378881.
[39] EP-A-0427347.
[40] WO93/17712
[41] WO94/03208.
[42] WO98/58668.
[43] EP-A-0471177.
[44] WO91/01146
[45] Falugi et al. (2001) *Eur J Immunol* 31:3816-3824.
[46] Baraldo et al. (2004) *Infect Immun* 72(8):4884-7.
[47] EP-A-0594610.
[48] Ruan et al. (1990) *J Immunol* 145:3379-3384.
[49] WO00/56360.
[50] WO02/091998.
[51] Kuo et al. (1995) *Infect Immun* 63:2706-13.
[52] Michon et al. (1998) *Vaccine.* 16:1732-41.
[53] WO01/72337
[54] WO00/61761.
[55] WO2004/041157.
[56] WO02/34771.
[57] WO99/42130.
[58] WO2004/011027.
[59] WO2007/113222
[60] U.S. Pat. No. 6,045,805
[61] U.S. Pat. No. 6,027,733 & 6,274,144.
[62] www.polymer.de
[63] U.S. Pat. Nos. 4,356,170 and 4,663,160
[64] U.S. Pat. No. 4,711,779.
[65] WO00/10599.
[66] U.S. Pat. No. 4,057,685.
[67] WO96/40242.
[68] Lei et al. (2000) *Dev Biol* (Basel) 103:259-264.
[69] WO00/38711; U.S. Pat. No. 6,146,902.
[70] WO2004/080490.
[71] WO2006/032475.
[72] WO2006/032500.
[73] WO2006/065553.
[74] WO2007/118979.
[75] WO99/24578.
[76] WO99/36544.
[77] WO99/57280.
[78] WO00/22430.
[79] Tettelin et al. (2000) *Science* 287:1809-1815.

[80] WO96/29412.
[81] Pizza et al. (2000) *Science* 287:1816-1820.
[82] WO01/52885.
[83] Bjune et al. (1991) *Lancet* 338(8775):1093-1096.
[84] Fukasawa et al. (1999) *Vaccine* 17:2951-2958.
[85] Rosenqvist et al. (1998) *Dev. Biol. Stand.* 92:323-333.
[86] Costantino et al. (1992) *Vaccine* 10:691-698.
[87] WO03/007985.
[88] Watson (2000) *Pediatr Infect Dis J* 19:331-332.
[89] Rubin (2000) *Pediatr Clin North Am* 47:269-285, v.
[90] Jedrzejas (2001) *Microbiol Mol Biol Rev* 65:187-207.
[91] Bell (2000) *Pediatr Infect Dis J* 19:1187-1188.
[92] Iwarson (1995) *APMIS* 103:321-326.
[93] Gerlich et al. (1990) *Vaccine* 8 Suppl:S63-68 & 79-80.
[94] Hsu et al. (1999) *Clin Liver Dis* 3:901-915.
[95] Gustafsson et al. (1996) *N. Engl. J. Med.* 334:349-355.
[96] Rappuoli et al. (1991) *TIBTECH* 9:232-238.
[97] Vaccines (2004) eds. Plotkin & Orenstein. ISBN 0-7216-9688-0.
[98] WO02/02606.
[99] Kalman et al. (1999) *Nature Genetics* 21:385-389.
[100] Read et al. (2000) *Nucleic Acids Res* 28:1397-406.
[101] Shirai et al. (2000) *J. Infect. Dis.* 181(Suppl 3):S524-S527.
[102] WO99/27105.
[103] WO00/27994.
[104] WO00/37494.
[105] WO99/28475.
[106] Ross et al. (2001) *Vaccine* 19:4135-4142.
[107] Sutter et al. (2000) *Pediatr Clin North Am* 47:287-308.
[108] Zimmerman & Spann (1999) *Am Fam Physician* 59:113-118, 125-126.
[109] Dreesen (1997) *Vaccine* 15 Suppl:S2-6.
[110] *MMWR Morb Mortal Wkly Rep* 1998 Jan. 16; 47(1): 12, 19.
[111] McMichael (2000) *Vaccine* 19 Suppl 1:S101-107.
[112] WO02/34771.
[113] Dale (1999) *Infect Dis Clin North Am* 13:227-43, viii.
[114] Ferretti et al. (2001) *PNAS USA* 98: 4658-4663.
[115] WO03/093306.
[116] WO2004/018646.
[117] WO2004/041157.
[118] Ichiman and Yoshida (1981) *J. Appl. Bacteriol.* 51:229.
[119] U.S. Pat. No. 4,197,290
[120] Ichiman et al. (1991) *J. Appl. Bacteriol.* 71:176.
[121] Robinson & Torres (1997) *Seminars in Immunology* 9:271-283.
[122] Donnelly et al. (1997) *Annu Rev Immunol* 15:617-648.
[123] Scott-Taylor & Dalgleish (2000) *Expert Opin Investig Drugs* 9:471-480.
[124] Apostolopoulos & Plebanski (2000) *Curr Opin Mol Ther* 2:441-447.
[125] Ilan (1999) *Curr Opin Mol Ther* 1:116-120.
[126] Dubensky et al. (2000) *Mol Med* 6:723-732.
[127] Robinson & Pertmer (2000) *Adv Virus Res* 55:1-74.
[128] Donnelly et al. (2000) *Am J Respir Crit Care Med* 162(4 Pt 2):S190-193.
[129] Davis (1999) *Mt. Sinai J. Med.* 66:84-90.
[130] Paoletti et al. (2001) *Vaccine* 19:2118-2126.
[131] WO00/56365.
[132] Gennaro (2000) *Remington: The Science and Practice of Pharmacy.* 20th edition, ISBN: 0683306472.
[133] WO03/009869.
[134] Almeida & Alpar (1996) *J. Drug Targeting* 3:455-467.
[135] Agarwal & Mishra (1999) *Indian J Exp Biol* 37:6-16.
[136] WO00/53221.
[137] Jakobsen et al. (2002) *Infect Immun* 70:1443-1452.
[138] Bergquist et al. (1998) *APMIS* 106:800-806.
[139] Baudner et al. (2002) *Infect Immun* 70:4785-4790.
[140] Ugozzoli et al. (2002) *J Infect Dis* 186:1358-1361.
[141] Vaccine Design . . . (1995) eds. Powell & Newman. ISBN: 030644867X. Plenum.
[142] WO00/23105.
[143] WO90/14837.
[144] Podda (2001) *Vaccine* 19:2673-80.
[145] Frey et al. (2003) *Vaccine* 21:4234-7.
[146] U.S. Pat. No. 6,299,884.
[147] U.S. Pat. No. 6,451,325.
[148] U.S. Pat. No. 5,057,540.
[149] WO96/33739.
[150] EP-A-0109942.
[151] WO96/11711.
[152] WO00/07621.
[153] Barr et al. (1998) *Advanced Drug Delivery Reviews* 32:247-271.
[154] Sjolanderet et al. (1998) *Advanced Drug Delivery Reviews* 32:321-338.
[155] Niikura et al. (2002) *Virology* 293:273-280.
[156] Lenz et al. (2001) *J Immunol* 166:5346-5355.
[157] Pinto et al. (2003) *J Infect Dis* 188:327-338.
[158] Gerber et al. (2001) *Virol* 75:4752-4760.
[159] WO03/024480
[160] WO03/024481
[161] Gluck et al. (2002) *Vaccine* 20:B10-B16.
[162] EP-A-0689454.
[163] Johnson et al. (1999) *Bioorg Med Chem Lett* 9:2273-2278.
[164] Evans et al. (2003) *Expert Rev Vaccines* 2:219-229.
[165] Meraldi et al. (2003) *Vaccine* 21:2485-2491.
[166] Pajak et al. (2003) *Vaccine* 21:836-842.
[168] Kandimalla et al. (2003) *Nucleic Acids Research* 31:2393-2400.
[169] WO02/26757.
[170] WO99/62923.
[171] Krieg (2003) *Nature Medicine* 9:831-835.
[172] McCluskie et al. (2002) *FEMS Immunology and Medical Microbiology* 32:179-185.
[173] WO98/40100.
[174] U.S. Pat. No. 6,207,646.
[175] U.S. Pat. No. 6,239,116.
[176] U.S. Pat. No. 6,429,199.
[177] Kandimalla et al. (2003) *Biochemical Society Transactions* 31 (part 3):654-658.
[177] Blackwell et al. (2003) *J Immunol* 170:4061-4068.
[178] Krieg (2002) *Trends Immunol* 23:64-65.
[179] WO01/95935.
[180] Kandimalla et al. (2003) *BBRC* 306:948-953.
[181] Bhagat et al. (2003) *BBRC* 300:853-861.
[182] WO03/035836.
[183] WO95/17211.
[184] WO98/42375.
[185] Beignon et al. (2002) *Infect Immun* 70:3012-3019.
[186] Pizza et al. (2001) *Vaccine* 19:2534-2541.
[187] Pizza et al. (2000) *Int J Med Microbiol* 290:455-461.
[188] Scharton-Kersten et al. (2000) *Infect Immun* 68:5306-5313.
[189] Ryan et al. (1999) *Infect Immun* 67:6270-6280.
[190] Partidos et al. (1999) *Immunol Lett* 67:209-216.
[191] Peppoloni et al. (2003) *Expert Rev Vaccines* 2:285-293.
[192] Pine et al. (2002) *J Control Release* 85:263-270.
[193] Domenighini et al. (1995) *Mol Microbiol* 15:1165-1167.

[194] WO99/40936.
[195] WO99/44636.
[196] Singh et all (2001) *J Cont Release* 70:267-276.
[197] WO99/27960.
[198] U.S. Pat. No. 6,090,406
[199] U.S. Pat. No. 5,916,588
[200] EP-A-0626169.
[201] WO99/52549.
[202] WO01/21207.
[203] WO01/21152.
[204] Andrianov et al. (1998) *Biomaterials* 19:109-115.
[205] Payne et al. (1998) *Adv Drug Delivery Review* 31:185-196.
[206] Stanley (2002) *Clin Exp Dermatol* 27:571-577.
[207] Jones (2003) *Curr Opin Investig Drugs* 4:214-218.
[208] WO04/60308
[209] WO04/64759.
[210] WO99/11241.
[211] WO94/00153.
[212] WO98/57659.
[213] European patent applications 0835318, 0735898 and 0761231.
[214] Joyce et al. (2003) *Carbohydrate Research* 338:903.
[215] Maira-Litran et al. (2002) *Infect. Immun.* 70:4433.
[216] WO2004/043407.
[217] WO2007/113224.
[218] WO2004/043405
[219] WO98/10788.
[220] WO2007/053176.
[221] WO2007/113222.
[222] WO2005/009379.
[223] WO2009/029132.
[224] WO2008/079315.
[225] WO2005/086663.
[226] WO2005/115113.
[227] WO2006/033918.
[228] WO2006/078680.
[229] Kuroda et al. (2001) *Lancet* 357(9264):1225-1240; see also pages 1218-1219.
[230] Sjodahl (1977) *J. Biochem.* 73:343-351.
[231] Uhlen et al. (1984) *J. Biol. Chem.* 259:1695-1702 & 13628 (Corr.).
[232] Schneewind et al. (1992) *Cell* 70:267-281.
[233] DeDent et al. (2008) *EMBO J.* 27:2656-2668.
[234] Sjoquist et al. (1972) *Eur. J. Biochem.* 30:190-194.
[235] DeDent et al. (2007) *J. Bacteriol.* 189:4473-4484.
[236] Deisenhofer et al., (1978) *Hoppe-Seyh Zeitsch. Physiol. Chem.* 359:975-985.
[237] Deisenhofer (1981) *Biochemistry* 20:2361-2370.
[238] Graille et al. (2000) *Proc. Nat. Acad. Sci. USA* 97:5399-5404.
[239] O'Seaghdha et al. (2006) *FEBS J.* 273:4831-41.
[240] Gomez et al. (2006) *J. Biol. Chem.* 281:20190-20196.
[241] WO2007/071692.
[242] Sebulsky & Heinrichs (2001) *J Bacteriol* 183:4994-5000.
[243] Sebulsky et al. (2003) *J Biol Chem* 278:49890-900.
[244] WO2005/009378.
[245] Rable & Wardenburg (2009) *Infect Immun* 77:2712-8.
[246] WO2007/145689.
[247] WO2009/029831.
[248] WO2005/079315.
[249] WO2008/152447.
[250] Kuklin et al. (2006) *Infect Immun.* 74(4):2215-23.
[251] WO2005/009379.
[252] Gennaro (2000) *Remington: The Science and Practice of Pharmacy.* 20th edition, ISBN: 0683306472.
[253] *Methods In Enzymology* (S. Colowick and N. Kaplan, eds., Academic Press, Inc.)
[254] *Handbook of Experimental Immunology*, Vols. I-IV (D. M. Weir and C.C. Blackwell, eds, 1986, Blackwell Scientific Publications)
[255] Sambrook et al. (2001) *Molecular Cloning: A Laboratory Manual*, 3rd edition (Cold Spring Harbor Laboratory Press).
[256] *Handbook of Surface and Colloidal Chemistry* (Birdi, K. S. ed., CRC Press, 1997)
[257] Ausubel et al. (eds) (2002) *Short protocols in molecular biology*, 5th edition (*Current Protocols*).
[258] Molecular Biology Techniques: An Intensive Laboratory Course, (Ream et al., eds., 1998, Academic Press)
[259] PCR (*Introduction to Biotechniques Series*), 2nd ed. (Newton & Graham eds., 1997, Springer Verlag)
[260] *Current Protocols in Molecular Biology* (F. M. Ausubel et al., eds., 1987) Supplement 30
[261] Smith & Waterman (1981) *Adv. Appl. Math.* 2: 482-489.
[262] Geysen et al. (1984) *PNAS USA* 81:3998-4002.
[263] Carter (1994) *Methods Mol Biol* 36:207-23.
[264] Jameson, B A et al. 1988, CABIOS 4(1):181-186.
[265] Raddrizzani & Hammer (2000) *Brief Bioinform* 1(2): 179-89.
[266] Bublil et al. (2007) *Proteins* 68(1):294-304.
[267] De Lalla et al. (1999) *J. Immunol.* 163:1725-29.
[268] Kwok et al. (2001) *Trends Immunol* 22:583-88.
[269] Brusic et al. (1998) *Bioinformatics* 14(2):121-30
[270] Meister et al. (1995) *Vaccine* 13(6):581-91.
[271] Roberts et al. (1996) *AIDS Res Hum Retroviruses* 12(7):593-610.
[272] Maksyutov & Zagrebelnaya (1993) *Comput Appl Biosci* 9(3):291-7.
[273] Feller & de la Cruz (1991) *Nature* 349(6311):720-1.
[274] Hopp (1993) *Peptide Research* 6:183-190.
[275] Welling et al. (1985) *FEBS Lett.* 188:215-218.
[276] Davenport et al. (1995) *Immunogenetics* 42:392-297.
[277] Tsurui & Takahashi (2007) *J Pharmacol Sci.* 105(4): 299-316.
[278] Tong et al. (2007) *Brief Bioinform.* 8(2):96-108.
[279] Schirle et al. (2001) *J Immunol Methods.* 257(1-2):1-16.
[280] Chen et al. (2007) *Amino Acids* 33(3):423-8.
[281] Bardotti et al. (2008) *Vaccine.* 26(18):2284-96.

We claim:

1. A process for preparing a conjugate of a fragment of an *S. aureus* type 5 capsular polysaccharide and a carrier molecule, comprising the steps of:
    (a) depolymerizing a full-length type 5 capsular polysaccharide to prepare a fragment of the type 5 capsular polysaccharide having a β-D-FucNAc-(1→moiety at its non-reducing terminus;
    (b) oxidising the fragment of the type 5 capsular polysaccharide to introduce an aldehyde group into at least one saccharide residue in the fragment to prepare a fragment having at least one oxidised saccharide residue; and
    (c) coupling the fragment having the at least one oxidised saccharide residue to the carrier molecule via the aldehyde group,
    thereby preparing the conjugate.

2. The process according to claim 1, wherein the depolymerising is carried out by acid hydrolysis using acetic acid.

3. The process according to of claim 1, wherein the average molecular mass of the fragment of the *S. aureus* type 5 capsular polysaccharide is between 5 and 100 kDa.

4. The process according to claim 1, wherein the fragment of the *S. aureus* type 5 capsular polysaccharide has a degree of O-acetylation of 10-90%.

5. The process of claim 1, wherein step (b) comprises oxidising the fragment of the *S. aureus* type 5 capsular polysaccharide to convert two vicinal hydroxyl groups in the β-D-FucNAc-(1→moiety into two aldehyde groups.

6. The process of claim 5, wherein step (c) comprises coupling the fragment having the at least one oxidised saccharide residue to the carrier molecule via one of the aldehyde groups.

7. The process of claim 1, wherein the coupling is direct coupling by reacting the aldehyde group with an amine group in the carrier molecule by reductive amination.

8. The process of claim 1, wherein the coupling is via a linker by reacting the aldehyde group with an amine group in the linker by reductive amination.

9. The process of claim 8, wherein the linker is attached to the carrier molecule.

10. The process of claim 1, wherein the coupling results in the type 5 capsular polysaccharide:carrier molecule ratio (w/w) of between 1:5 and 1:2.

* * * * *

SEQUENCE LISTING

<160> NUMBER OF SEQ ID NOS: 56

<210> SEQ ID NO 1
<211> LENGTH: 927
<212> TYPE: PRT
<213> ORGANISM: Staphylococcus aureus

<400> SEQUENCE: 1

```
Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Thr Asn Gln Ala Asn Thr Pro
            115                 120                 125

Ala Thr Thr Gln Ser Ser Asn Thr Asn Ala Glu Glu Leu Val Asn Gln
            130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
            195                 200                 205

Ser Ala Pro Arg Met Arg Ala Phe Ser Leu Ala Ala Val Ala Ala Asp
            210                 215                 220

Ala Pro Val Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
            275                 280                 285

Thr Ser Thr Ala Lys Val Pro Pro Ile Met Ala Gly Asp Gln Val Leu
            290                 295                 300

Ala Asn Gly Val Ile Asp Ser Asp Gly Asn Val Ile Tyr Thr Phe Thr
305                 310                 315                 320

Asp Tyr Val Asn Thr Lys Asp Asp Val Lys Ala Thr Leu Thr Met Pro
                325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
            355                 360                 365

Tyr Glu Lys Tyr Gly Lys Phe Tyr Asn Leu Ser Ile Lys Gly Thr Ile
            370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415
```

```
Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
                435                 440                 445

Phe Val Asn Pro Glu Asn Phe Glu Asp Val Thr Asn Ser Val Asn Ile
450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

Pro Asn Ser Lys Gly Asp Leu Ala Leu Arg Ser Thr Leu Tyr Gly Tyr
                500                 505                 510

Asn Ser Asn Ile Ile Trp Arg Ser Met Ser Trp Asp Asn Glu Val Ala
            515                 520                 525

Phe Asn Asn Gly Ser Gly Ser Gly Asp Gly Ile Asp Lys Pro Val Val
530                 535                 540

Pro Glu Gln Pro Asp Glu Pro Gly Glu Ile Glu Pro Ile Pro Glu Asp
545                 550                 555                 560

Ser Asp Ser Asp Pro Gly Ser Asp Ser Gly Ser Asp Ser Asn Ser Asp
                565                 570                 575

Ser Gly Ser Asp Ser Gly Ser Asp Ser Thr Ser Asp Ser Gly Ser Asp
                580                 585                 590

Ser Ala Ser Asp Ser Asp Ser Ala Ser Asp Ser Asp Ser Ala Ser Asp
                595                 600                 605

Ser Asp Ser Ala Ser Asp Ser Asp Ser Ala Ser Asp Ser Asp Ser Asp
            610                 615                 620

Asn Asp Ser Asp Ser Asp Ser Asp Ser Asp Ser Asp Ser Asp Ser Asp
625                 630                 635                 640

Ser Asp Ser Asp Ser Asp Ser Asp Ser Asp Ser Asp Ser Asp Ser Asp
                645                 650                 655

Ser Asp Ser Asp Ser Asp Ser Asp Ser Asp Ser Asp Ser Asp Ser Asp
                660                 665                 670

Ser Asp Ser Asp Ser Asp Ser Asp Ser Asp Ser Asp Ser Asp Ser Asp
            675                 680                 685

Ser Asp Ser Asp Ser Asp Ser Asp Ser Asp Ser Asp Ser Asp Ser Asp
            690                 695                 700

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
                725                 730                 735

Ser Asp Ser Asp Ser Asp Ser Asp Ser Asp Ser Asp Ser Asp Ser Asp
                740                 745                 750

Ser Asp Ser Asp Ser Asp Ser Asp Ser Asp Ser Asp Ser Asp Ser Ala
                755                 760                 765

Ser Asp Ser Asp Ser Asp Ser Asp Ser Asp Ser Asp Ser Asp Ser Asp
                770                 775                 780

Ser Asp Ser Asp Ser Asp Ser Asp Ser Asp Ser Asp Ser Asp Ser Asp
785                 790                 795                 800

Ser Asp Ser Asp Ser Asp Ser Glu Ser Asp Ser Asp Ser Asp Ser Asp
                805                 810                 815

Ser Asp Ser Asp Ser Asp Ser Asp Ser Asp Ser Asp Ser Asp Ser Ala
                820                 825                 830
```

| | | | | | | | | | | | | |
|---|---|---|---|---|---|---|---|---|---|---|---|---|
|Ser|Asp|Ser|Asp|Ser|Gly|Ser|Asp|Ser|Asp|Ser|Ser|Asp|
| | |835| | | |840| | | |845| | |

Ser Glu Ser Asp Ser Asn Ser Asp Ser Glu Ser Val Ser Asn Asn
           850                855                860

Val Val Pro Pro Asn Ser Pro Lys Asn Gly Thr Asn Ala Ser Asn Lys
865             870                 875                 880

Asn Glu Ala Lys Asp Ser Lys Glu Pro Leu Pro Asp Thr Gly Ser Glu
                885                 890                 895

Asp Glu Ala Asn Thr Ser Leu Ile Trp Gly Leu Leu Ala Ser Ile Gly
                900                 905                 910

Ser Leu Leu Leu Phe Arg Arg Lys Lys Glu Asn Lys Asp Lys Lys
                915                 920                 925

<210> SEQ ID NO 2
<211> LENGTH: 520
<212> TYPE: PRT
<213> ORGANISM: Staphylococcus aureus

<400> SEQUENCE: 2

Ser Glu Asn Ser Val Thr Gln Ser Asp Ser Ala Ser Asn Glu Ser Lys
1               5                   10                  15

Ser Asn Asp Ser Ser Val Ser Ala Ala Pro Lys Thr Asp Asp Thr
            20                  25                  30

Asn Val Ser Asp Thr Lys Thr Ser Ser Asn Thr Asn Asn Gly Glu Thr
        35                  40                  45

Ser Val Ala Gln Asn Pro Ala Gln Gln Glu Thr Thr Gln Ser Ser Ser
    50                  55                  60

Thr Asn Ala Thr Thr Glu Glu Thr Pro Val Thr Gly Glu Ala Thr Thr
65                  70                  75                  80

Thr Thr Thr Asn Gln Ala Asn Thr Pro Ala Thr Gln Ser Ser Asn
                85                  90                  95

Thr Asn Ala Glu Glu Leu Val Asn Gln Thr Ser Asn Glu Thr Thr Ser
                100                 105                 110

Asn Asp Thr Asn Thr Val Ser Ser Val Asn Ser Pro Gln Asn Ser Thr
            115                 120                 125

Asn Ala Glu Asn Val Ser Thr Thr Gln Asp Thr Ser Thr Glu Ala Thr
        130                 135                 140

Pro Ser Asn Asn Glu Ser Ala Pro Gln Ser Thr Asp Ala Ser Asn Lys
145                 150                 155                 160

Asp Val Val Asn Gln Ala Val Asn Thr Ser Ala Pro Arg Met Arg Ala
                165                 170                 175

Phe Ser Leu Ala Ala Val Ala Ala Asp Ala Pro Val Ala Gly Thr Asp
            180                 185                 190

Ile Thr Asn Gln Leu Thr Asn Val Thr Val Gly Ile Asp Ser Gly Thr
        195                 200                 205

Thr Val Tyr Pro His Gln Ala Gly Tyr Val Lys Leu Asn Tyr Gly Phe
    210                 215                 220

Ser Val Pro Asn Ser Ala Val Lys Gly Asp Thr Phe Lys Ile Thr Val
225                 230                 235                 240

Pro Lys Glu Leu Asn Leu Asn Gly Val Thr Ser Thr Ala Lys Val Pro
                245                 250                 255

Pro Ile Met Ala Gly Asp Gln Val Leu Ala Asn Gly Val Ile Asp Ser
                260                 265                 270

Asp Gly Asn Val Ile Tyr Thr Phe Thr Asp Tyr Val Asn Thr Lys Asp
            275                 280                 285

-continued

Asp Val Lys Ala Thr Leu Thr Met Pro Ala Tyr Ile Asp Pro Glu Asn
            290                 295                 300

Val Lys Lys Thr Gly Asn Val Thr Leu Ala Thr Gly Ile Gly Ser Thr
305                 310                 315                 320

Thr Ala Asn Lys Thr Val Leu Val Asp Tyr Glu Lys Tyr Gly Lys Phe
                325                 330                 335

Tyr Asn Leu Ser Ile Lys Gly Thr Ile Asp Gln Ile Asp Lys Thr Asn
            340                 345                 350

Asn Thr Tyr Arg Gln Thr Ile Tyr Val Asn Pro Ser Gly Asp Asn Val
        355                 360                 365

Ile Ala Pro Val Leu Thr Gly Asn Leu Lys Pro Asn Thr Asp Ser Asn
370                 375                 380

Ala Leu Ile Asp Gln Gln Asn Thr Ser Ile Lys Val Tyr Lys Val Asp
385                 390                 395                 400

Asn Ala Ala Asp Leu Ser Glu Ser Tyr Phe Val Asn Pro Glu Asn Phe
                405                 410                 415

Glu Asp Val Thr Asn Ser Val Asn Ile Thr Phe Pro Asn Pro Asn Gln
            420                 425                 430

Tyr Lys Val Glu Phe Asn Thr Pro Asp Asp Gln Ile Thr Thr Pro Tyr
        435                 440                 445

Ile Val Val Val Asn Gly His Ile Asp Pro Asn Ser Lys Gly Asp Leu
450                 455                 460

Ala Leu Arg Ser Thr Leu Tyr Gly Tyr Asn Ser Asn Ile Ile Trp Arg
465                 470                 475                 480

Ser Met Ser Trp Asp Asn Glu Val Ala Phe Asn Gly Ser Gly Ser
                485                 490                 495

Gly Asp Gly Ile Asp Lys Pro Val Val Pro Glu Gln Pro Asp Glu Pro
            500                 505                 510

Gly Glu Ile Glu Pro Ile Pro Glu
        515                 520

<210> SEQ ID NO 3
<211> LENGTH: 877
<212> TYPE: PRT
<213> ORGANISM: Staphylococcus aureus

<400> SEQUENCE: 3

Met Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Thr Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asn Gln Ala
        115                 120                 125

Thr Ala Ala Lys Met Gln Asp Gln Thr Val Pro Gln Glu Ala Asn Ser

```
            130                 135                 140
Gln Val Asp Asn Lys Thr Thr Asn Asp Ala Asn Ser Ile Ala Thr Asn
145                 150                 155                 160

Ser Glu Leu Lys Asn Ser Gln Thr Leu Asp Leu Pro Gln Ser Ser Pro
                165                 170                 175

Gln Thr Ile Ser Asn Ala Gln Gly Thr Ser Lys Pro Ser Val Arg Thr
                180                 185                 190

Arg Ala Val Arg Ser Leu Ala Val Ala Glu Pro Val Val Asn Ala Ala
                195                 200                 205

Asp Ala Lys Gly Thr Asn Val Asn Asp Lys Val Thr Ala Ser Asn Phe
210                 215                 220

Lys Leu Glu Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255

Phe Thr Ala Lys Leu Pro Asp Ser Leu Thr Gly Asn Gly Asp Val Asp
                260                 265                 270

Tyr Ser Asn Ser Asn Asn Thr Met Pro Ile Ala Asp Ile Lys Ser Thr
                275                 280                 285

Asn Gly Asp Val Val Ala Lys Ala Thr Tyr Asp Ile Leu Thr Lys Thr
                290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
                340                 345                 350

Asn Lys Ile Thr Tyr Asn Tyr Ser Ser Pro Ile Ala Gly Ile Asp Lys
                355                 360                 365

Pro Asn Gly Ala Asn Ile Ser Ser Gln Ile Ile Gly Val Asp Thr Ala
                370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
                420                 425                 430

Ile Phe Glu Val Asn Asp Thr Ser Lys Leu Ser Asp Ser Tyr Tyr Ala
                435                 440                 445

Asp Pro Asn Asp Ser Asn Leu Lys Glu Val Thr Asp Gln Phe Lys Asn
450                 455                 460

Arg Ile Tyr Tyr Glu His Pro Asn Val Ala Ser Ile Lys Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Val Asp Pro Val
                500                 505                 510

Thr Asn Arg Asp Tyr Ser Ile Phe Gly Trp Asn Asn Glu Asn Val Val
                515                 520                 525

Arg Tyr Gly Gly Gly Ser Ala Asp Gly Asp Ser Ala Val Asn Pro Lys
                530                 535                 540

Asp Pro Thr Pro Gly Pro Pro Val Asp Pro Glu Pro Ser Pro Asp Pro
545                 550                 555                 560
```

```
Glu Pro Glu Pro Thr Pro Asp Pro Glu Pro Ser Pro Asp Pro Glu Pro
                565                 570                 575
Glu Pro Ser Pro Asp Pro Asp Pro Asp Ser Asp Ser Asp Ser Asp Ser
            580                 585                 590
Gly Ser Asp Ser Asp Ser Gly Ser Asp Ser Asp Ser Glu Ser Asp Ser
        595                 600                 605
Asp Ser Asp Ser Asp Ser Ser Asp Ser Asp Ser Asp Ser Glu Ser
    610                 615                 620
Asp Ser Asp Ser Glu Ser Asp Ser Glu Ser Asp Ser Asp Ser Asp Ser
625                 630                 635                 640
Asp Ser Asp Ser Asp Ser Asp Ser Asp Ser Asp Ser Asp Ser Asp Ser
                645                 650                 655
Asp Ser Asp Ser Asp Ser Asp Ser Asp Ser Asp Ser Asp Ser Asp Ser
            660                 665                 670
Asp Ser Asp Ser Asp Ser Asp Ser Asp Ser Asp Ser Asp Ser Asp Ser
        675                 680                 685
Asp Ser Asp Ser Asp Ser Asp Ser Asp Ser Asp Ser Asp Ser Asp Ser
    690                 695                 700
Asp Ser Asp Ser Asp Ser Asp Ser Asp Ser Asp Ser Asp Ser Asp Ser
705                 710                 715                 720
Asp Ser Asp Ser Asp Ser Asp Ser Asp Ser Asp Ser Asp Ser Asp Ser
                725                 730                 735
Asp Ser Asp Ser Asp Ser Asp Ser Asp Ser Asp Ser Asp Ser Asp Ser
            740                 745                 750
Asp Ser Asp Ser Asp Ser Asp Ser Asp Ser Asp Ser Asp Ser Asp Ser
        755                 760                 765
Asp Ser Asp Ser Asp Ser Asp Ser Asp Ser Asp Ser Asp Ser Asp Ser
    770                 775                 780
Asp Ser Asp Ser Asp Ser Asp Ser Asp Ser Asp Ser Asp Ser Asp Ser
785                 790                 795                 800
Asp Ser Asp Ser Arg Val Thr Pro Pro Asn Asn Glu Gln Lys Ala Pro
                805                 810                 815
Ser Asn Pro Lys Gly Glu Val Asn His Ser Asn Lys Val Ser Lys Gln
            820                 825                 830
His Lys Thr Asp Ala Leu Pro Glu Thr Gly Asp Lys Ser Glu Asn Thr
        835                 840                 845
Asn Ala Thr Leu Phe Gly Ala Met Met Ala Leu Leu Gly Ser Leu Leu
    850                 855                 860
Leu Phe Arg Lys Arg Lys Gln Asp His Lys Glu Lys Ala
865                 870                 875

<210> SEQ ID NO 4
<211> LENGTH: 508
<212> TYPE: PRT
<213> ORGANISM: Staphylococcus aureus

<400> SEQUENCE: 4

Ser Glu Gln Ser Asn Asp Thr Thr Gln Ser Ser Lys Asn Asn Ala Ser
1               5                   10                  15
Ala Asp Ser Glu Lys Asn Asn Met Ile Glu Thr Pro Gln Leu Asn Thr
            20                  25                  30
Thr Ala Asn Asp Thr Ser Asp Ile Ser Ala Asn Thr Asn Ser Ala Asn
        35                  40                  45
Val Asp Ser Thr Thr Lys Pro Met Ser Thr Gln Thr Ser Asn Thr Thr
```

```
         50                  55                  60
Thr Thr Glu Pro Ala Ser Thr Asn Glu Thr Pro Gln Pro Thr Ala Ile
 65                  70                  75                  80

Lys Asn Gln Ala Thr Ala Ala Lys Met Gln Asp Gln Thr Val Pro Gln
                     85                  90                  95

Glu Ala Asn Ser Gln Val Asp Asn Lys Thr Thr Asn Asp Ala Asn Ser
                100                 105                 110

Ile Ala Thr Asn Ser Glu Leu Lys Asn Ser Gln Thr Leu Asp Leu Pro
                115                 120                 125

Gln Ser Ser Pro Gln Thr Ile Ser Asn Ala Gln Gly Thr Ser Lys Pro
                130                 135                 140

Ser Val Arg Thr Arg Ala Val Arg Ser Leu Ala Val Ala Glu Pro Val
145                 150                 155                 160

Val Asn Ala Ala Asp Ala Lys Gly Thr Asn Val Asn Asp Lys Val Thr
                165                 170                 175

Ala Ser Asn Phe Lys Leu Glu Lys Thr Thr Phe Asp Pro Asn Gln Ser
                180                 185                 190

Gly Asn Thr Phe Met Ala Ala Asn Phe Thr Val Thr Asp Lys Val Lys
                195                 200                 205

Ser Gly Asp Tyr Phe Thr Ala Lys Leu Pro Asp Ser Leu Thr Gly Asn
210                 215                 220

Gly Asp Val Asp Tyr Ser Asn Ser Asn Thr Met Pro Ile Ala Asp
225                 230                 235                 240

Ile Lys Ser Thr Asn Gly Asp Val Val Ala Lys Ala Thr Tyr Asp Ile
                245                 250                 255

Leu Thr Lys Thr Tyr Thr Phe Val Phe Thr Asp Tyr Val Asn Asn Lys
                260                 265                 270

Glu Asn Ile Asn Gly Gln Phe Ser Leu Pro Leu Phe Thr Asp Arg Ala
                275                 280                 285

Lys Ala Pro Lys Ser Gly Thr Tyr Asp Ala Asn Ile Asn Ile Ala Asp
                290                 295                 300

Glu Met Phe Asn Asn Lys Ile Thr Tyr Asn Tyr Ser Ser Pro Ile Ala
305                 310                 315                 320

Gly Ile Asp Lys Pro Asn Gly Ala Asn Ile Ser Ser Gln Ile Ile Gly
                325                 330                 335

Val Asp Thr Ala Ser Gly Gln Asn Thr Tyr Lys Gln Thr Val Phe Val
                340                 345                 350

Asn Pro Lys Gln Arg Val Leu Gly Asn Thr Trp Val Tyr Ile Lys Gly
                355                 360                 365

Tyr Gln Asp Lys Ile Glu Glu Ser Ser Gly Lys Val Ser Ala Thr Asp
                370                 375                 380

Thr Lys Leu Arg Ile Phe Glu Val Asn Asp Thr Ser Lys Leu Ser Asp
385                 390                 395                 400

Ser Tyr Tyr Ala Asp Pro Asn Asp Ser Asn Leu Lys Glu Val Thr Asp
                405                 410                 415

Gln Phe Lys Asn Arg Ile Tyr Tyr Glu His Pro Asn Val Ala Ser Ile
                420                 425                 430

Lys Phe Gly Asp Ile Thr Lys Thr Tyr Val Val Leu Val Glu Gly His
                435                 440                 445

Tyr Asp Asn Thr Gly Lys Asn Leu Lys Thr Gln Val Ile Gln Glu Asn
                450                 455                 460

Val Asp Pro Val Thr Asn Arg Asp Tyr Ser Ile Phe Gly Trp Asn Asn
465                 470                 475                 480
```

```
Glu Asn Val Val Arg Tyr Gly Gly Ser Ala Asp Gly Asp Ser Ala
                485                 490                 495

Val Asn Pro Lys Asp Pro Thr Pro Gly Pro Pro Val
            500                 505

<210> SEQ ID NO 5
<211> LENGTH: 316
<212> TYPE: PRT
<213> ORGANISM: Staphylococcus aureus

<400> SEQUENCE: 5

Ser Glu Gln Ser Asn Asp Thr Thr Gln Ser Ser Lys Asn Asn Ala Ser
1               5                   10                  15

Ala Asp Ser Glu Lys Asn Asn Met Ile Glu Thr Pro Gln Leu Asn Thr
            20                  25                  30

Thr Ala Asn Asp Thr Ser Asp Ile Ser Ala Asn Thr Asn Ser Ala Asn
        35                  40                  45

Val Asp Ser Thr Thr Lys Pro Met Ser Thr Gln Thr Ser Asn Thr Thr
50                  55                  60

Thr Thr Glu Pro Ala Ser Thr Asn Glu Thr Pro Gln Pro Thr Ala Ile
65                  70                  75                  80

Lys Asn Gln Ala Thr Ala Ala Lys Met Gln Asp Gln Thr Val Pro Gln
                85                  90                  95

Glu Ala Asn Ser Gln Val Asp Asn Lys Thr Thr Asn Asp Ala Asn Ser
            100                 105                 110

Ile Ala Thr Asn Ser Glu Leu Lys Asn Ser Gln Thr Leu Asp Leu Pro
        115                 120                 125

Gln Ser Ser Pro Gln Thr Ile Ser Asn Ala Gln Gly Thr Ser Lys Pro
130                 135                 140

Ser Val Arg Thr Arg Ala Val Arg Ser Leu Ala Val Ala Glu Pro Val
145                 150                 155                 160

Val Asn Ala Ala Asp Ala Lys Gly Thr Asn Val Asn Asp Lys Val Thr
                165                 170                 175

Ala Ser Asn Phe Lys Leu Glu Lys Thr Thr Phe Asp Pro Asn Gln Ser
            180                 185                 190

Gly Asn Thr Phe Met Ala Ala Asn Phe Thr Val Thr Asp Lys Val Lys
        195                 200                 205

Ser Gly Asp Tyr Phe Thr Ala Lys Leu Pro Asp Ser Leu Thr Gly Asn
210                 215                 220

Gly Asp Val Asp Tyr Ser Asn Ser Asn Thr Met Pro Ile Ala Asp
225                 230                 235                 240

Ile Lys Ser Thr Asn Gly Asp Val Val Ala Lys Ala Thr Tyr Asp Ile
                245                 250                 255

Leu Thr Lys Thr Tyr Thr Phe Val Phe Thr Asp Tyr Val Asn Asn Lys
            260                 265                 270

Glu Asn Ile Asn Gly Gln Phe Ser Leu Pro Leu Phe Thr Asp Arg Ala
        275                 280                 285

Lys Ala Pro Lys Ser Gly Thr Tyr Asp Ala Asn Ile Asn Ile Ala Asp
290                 295                 300

Glu Met Phe Asn Asn Lys Ile Thr Tyr Asn Tyr Ser
305                 310                 315

<210> SEQ ID NO 6
<211> LENGTH: 331
<212> TYPE: PRT
```

<213> ORGANISM: Staphylococcus aureus

<400> SEQUENCE: 6

Gly Thr Asn Val Asn Asp Lys Val Thr Ala Ser Asn Phe Lys Leu Glu
1               5                   10                  15

Lys Thr Thr Phe Asp Pro Asn Gln Ser Gly Asn Thr Phe Met Ala Ala
            20                  25                  30

Asn Phe Thr Val Thr Asp Lys Val Lys Ser Gly Asp Tyr Phe Thr Ala
        35                  40                  45

Lys Leu Pro Asp Ser Leu Thr Gly Asn Gly Asp Val Asp Tyr Ser Asn
    50                  55                  60

Ser Asn Asn Thr Met Pro Ile Ala Asp Ile Lys Ser Thr Asn Gly Asp
65                  70                  75                  80

Val Val Ala Lys Ala Thr Tyr Asp Ile Leu Thr Lys Thr Tyr Thr Phe
                85                  90                  95

Val Phe Thr Asp Tyr Val Asn Asn Lys Glu Asn Ile Asn Gly Gln Phe
            100                 105                 110

Ser Leu Pro Leu Phe Thr Asp Arg Ala Lys Ala Pro Lys Ser Gly Thr
        115                 120                 125

Tyr Asp Ala Asn Ile Asn Ile Ala Asp Glu Met Phe Asn Asn Lys Ile
    130                 135                 140

Thr Tyr Asn Tyr Ser Ser Pro Ile Ala Gly Ile Asp Lys Pro Asn Gly
145                 150                 155                 160

Ala Asn Ile Ser Ser Gln Ile Ile Gly Val Asp Thr Ala Ser Gly Gln
                165                 170                 175

Asn Thr Tyr Lys Gln Thr Val Phe Val Asn Pro Lys Gln Arg Val Leu
            180                 185                 190

Gly Asn Thr Trp Val Tyr Ile Lys Gly Tyr Gln Asp Lys Ile Glu Glu
        195                 200                 205

Ser Ser Gly Lys Val Ser Ala Thr Asp Thr Lys Leu Arg Ile Phe Glu
    210                 215                 220

Val Asn Asp Thr Ser Lys Leu Ser Asp Ser Tyr Tyr Ala Asp Pro Asn
225                 230                 235                 240

Asp Ser Asn Leu Lys Glu Val Thr Asp Gln Phe Lys Asn Arg Ile Tyr
                245                 250                 255

Tyr Glu His Pro Asn Val Ala Ser Ile Lys Phe Gly Asp Ile Thr Lys
            260                 265                 270

Thr Tyr Val Val Leu Val Glu Gly His Tyr Asp Asn Thr Gly Lys Asn
        275                 280                 285

Leu Lys Thr Gln Val Ile Gln Glu Asn Val Asp Pro Val Thr Asn Arg
    290                 295                 300

Asp Tyr Ser Ile Phe Gly Trp Asn Asn Glu Asn Val Val Arg Tyr Gly
305                 310                 315                 320

Gly Gly Ser Ala Asp Gly Asp Ser Ala Val Asn
                325                 330

<210> SEQ ID NO 7
<211> LENGTH: 183
<212> TYPE: PRT
<213> ORGANISM: Staphylococcus aureus

<400> SEQUENCE: 7

Ser Ser Pro Ile Ala Gly Ile Asp Lys Pro Asn Gly Ala Asn Ile Ser
1               5                   10                  15

Ser Gln Ile Ile Gly Val Asp Thr Ala Ser Gly Gln Asn Thr Tyr Lys

```
              20                  25                  30
Gln Thr Val Phe Val Asn Pro Lys Gln Arg Val Leu Gly Asn Thr Trp
             35                  40                  45
Val Tyr Ile Lys Gly Tyr Gln Asp Lys Ile Glu Glu Ser Ser Gly Lys
         50                  55                  60
Val Ser Ala Thr Asp Thr Lys Leu Arg Ile Phe Glu Val Asn Asp Thr
 65                  70                  75                  80
Ser Lys Leu Ser Asp Ser Tyr Tyr Ala Asp Pro Asn Asp Ser Asn Leu
                 85                  90                  95
Lys Glu Val Thr Asp Gln Phe Lys Asn Arg Ile Tyr Tyr Glu His Pro
            100                 105                 110
Asn Val Ala Ser Ile Lys Phe Gly Asp Ile Thr Lys Thr Tyr Val Val
            115                 120                 125
Leu Val Glu Gly His Tyr Asp Asn Thr Gly Lys Asn Leu Lys Thr Gln
        130                 135                 140
Val Ile Gln Glu Asn Val Asp Pro Val Thr Asn Arg Asp Tyr Ser Ile
145                 150                 155                 160
Phe Gly Trp Asn Asn Glu Asn Val Val Arg Tyr Gly Gly Gly Ser Ala
                165                 170                 175
Asp Gly Asp Ser Ala Val Asn
            180
```

<210> SEQ ID NO 8
<211> LENGTH: 1166
<212> TYPE: PRT
<213> ORGANISM: Staphylococcus aureus

<400> SEQUENCE: 8

```
Met Ile Asn Arg Asp Asn Lys Lys Ala Ile Thr Lys Lys Gly Met Ile
 1               5                  10                  15
Ser Asn Arg Leu Asn Lys Phe Ser Ile Arg Lys Tyr Thr Val Gly Thr
             20                  25                  30
Ala Ser Ile Leu Val Gly Thr Thr Leu Ile Phe Gly Leu Gly Asn Gln
             35                  40                  45
Glu Ala Lys Ala Ala Glu Asn Thr Ser Thr Glu Asn Ala Lys Gln Asp
         50                  55                  60
Asp Ala Thr Thr Ser Asp Asn Lys Glu Val Val Ser Glu Thr Glu Asn
 65                  70                  75                  80
Asn Ser Thr Thr Glu Asn Asn Ser Thr Asn Pro Ile Lys Lys Glu Thr
                 85                  90                  95
Asn Thr Asp Ser Gln Pro Glu Ala Lys Lys Glu Ser Thr Ser Ser Ser
            100                 105                 110
Thr Gln Lys Gln Gln Asn Asn Val Thr Ala Thr Thr Glu Thr Lys Pro
        115                 120                 125
Gln Asn Ile Glu Lys Glu Asn Val Lys Pro Ser Thr Asp Lys Thr Ala
130                 135                 140
Thr Glu Asp Thr Ser Val Ile Leu Glu Glu Lys Ala Pro Asn Asn
145                 150                 155                 160
Thr Asn Asn Asp Val Thr Thr Lys Pro Ser Thr Ser Glu Pro Ser Thr
                165                 170                 175
Ser Glu Ile Gln Thr Lys Pro Thr Pro Gln Glu Ser Thr Asn Ile
            180                 185                 190
Glu Asn Ser Gln Pro Gln Pro Thr Pro Ser Lys Val Asp Asn Gln Val
        195                 200                 205
```

```
Thr Asp Ala Thr Asn Pro Lys Glu Pro Val Asn Val Ser Lys Glu Glu
    210                 215                 220

Leu Lys Asn Asn Pro Glu Lys Leu Lys Glu Leu Val Arg Asn Asp Ser
225                 230                 235                 240

Asn Thr Asp His Ser Thr Lys Pro Val Ala Thr Ala Pro Thr Ser Val
                245                 250                 255

Ala Pro Lys Arg Val Asn Ala Lys Met Arg Phe Ala Val Ala Gln Pro
            260                 265                 270

Ala Ala Val Ala Ser Asn Asn Val Asn Asp Leu Ile Lys Val Thr Lys
            275                 280                 285

Gln Thr Ile Lys Val Gly Asp Gly Lys Asp Asn Val Ala Ala Ala His
290                 295                 300

Asp Gly Lys Asp Ile Glu Tyr Asp Thr Glu Phe Thr Ile Asp Asn Lys
305                 310                 315                 320

Val Lys Lys Gly Asp Thr Met Thr Ile Asn Tyr Asp Lys Asn Val Ile
                325                 330                 335

Pro Ser Asp Leu Thr Asp Lys Asn Asp Pro Ile Asp Ile Thr Asp Pro
                340                 345                 350

Ser Gly Glu Val Ile Ala Lys Gly Thr Phe Asp Lys Ala Thr Lys Gln
                355                 360                 365

Ile Thr Tyr Thr Phe Thr Asp Tyr Val Asp Lys Tyr Glu Asp Ile Lys
370                 375                 380

Ser Arg Leu Thr Leu Tyr Ser Tyr Ile Asp Lys Lys Thr Val Pro Asn
385                 390                 395                 400

Glu Thr Ser Leu Asn Leu Thr Phe Ala Thr Ala Gly Lys Glu Thr Ser
                405                 410                 415

Gln Asn Val Thr Val Asp Tyr Gln Asp Pro Met Val His Gly Asp Ser
                420                 425                 430

Asn Ile Gln Ser Ile Phe Thr Lys Leu Asp Glu Asp Lys Gln Thr Ile
                435                 440                 445

Glu Gln Gln Ile Tyr Val Asn Pro Leu Lys Lys Ser Ala Thr Asn Thr
                450                 455                 460

Lys Val Asp Ile Ala Gly Ser Gln Val Asp Asp Tyr Gly Asn Ile Lys
465                 470                 475                 480

Leu Gly Asn Gly Ser Thr Ile Ile Asp Gln Asn Thr Glu Ile Lys Val
                485                 490                 495

Tyr Lys Val Asn Ser Asp Gln Gln Leu Pro Gln Ser Asn Arg Ile Tyr
                500                 505                 510

Asp Phe Ser Gln Tyr Glu Asp Val Thr Ser Gln Phe Asp Asn Lys Lys
                515                 520                 525

Ser Phe Ser Asn Asn Val Ala Thr Leu Asp Phe Gly Asp Ile Asn Ser
530                 535                 540

Ala Tyr Ile Ile Lys Val Val Ser Lys Tyr Thr Pro Thr Ser Asp Gly
545                 550                 555                 560

Glu Leu Asp Ile Ala Gln Gly Thr Ser Met Arg Thr Thr Asp Lys Tyr
                565                 570                 575

Gly Tyr Tyr Asn Tyr Ala Gly Tyr Ser Asn Phe Ile Val Thr Ser Asn
                580                 585                 590

Asp Thr Gly Gly Asp Gly Thr Val Lys Pro Glu Lys Leu Tyr
                595                 600                 605

Lys Ile Gly Asp Tyr Val Trp Glu Asp Val Asp Lys Asp Gly Val Gln
610                 615                 620

Gly Thr Asp Ser Lys Glu Lys Pro Met Ala Asn Val Leu Val Thr Leu
```

```
               625                 630                 635                 640
           Thr Tyr Pro Asp Gly Thr Thr Lys Ser Val Arg Thr Asp Ala Asn Gly
                           645                 650                 655

His Tyr Glu Phe Gly Gly Leu Lys Asp Gly Glu Thr Tyr Thr Val Lys
                           660                 665                 670

Phe Glu Thr Pro Thr Gly Tyr Leu Pro Thr Lys Val Asn Gly Thr Thr
                           675                 680                 685

Asp Gly Glu Lys Asp Ser Asn Gly Ser Val Thr Val Lys Ile Asn
                           690                 695                 700

Gly Lys Asp Asp Met Ser Leu Asp Thr Gly Phe Tyr Lys Glu Pro Lys
           705                 710                 715                 720

Tyr Asn Leu Gly Asp Tyr Val Trp Glu Asp Thr Asn Lys Asp Gly Ile
                           725                 730                 735

Gln Asp Ala Asn Glu Pro Gly Ile Lys Asp Val Lys Val Thr Leu Lys
                           740                 745                 750

Asp Ser Thr Gly Lys Val Ile Gly Thr Thr Thr Asp Ala Ser Gly
                           755                 760                 765

Lys Tyr Lys Phe Thr Asp Leu Asp Asn Gly Asn Tyr Thr Val Glu Phe
                           770                 775                 780

Glu Thr Pro Ala Gly Tyr Thr Pro Thr Val Lys Asn Thr Thr Ala Asp
           785                 790                 795                 800

Asp Lys Asp Ser Asn Gly Leu Thr Thr Thr Gly Val Ile Lys Asp Ala
                           805                 810                 815

Asp Asn Met Thr Leu Asp Arg Gly Phe Tyr Lys Thr Pro Lys Tyr Ser
                           820                 825                 830

Leu Gly Asp Tyr Val Trp Tyr Asp Ser Asn Lys Asp Gly Lys Gln Asp
                           835                 840                 845

Ser Thr Glu Lys Gly Ile Lys Asp Val Thr Val Thr Leu Gln Asn Glu
                           850                 855                 860

Lys Gly Glu Val Ile Gly Thr Thr Lys Thr Asp Glu Asn Gly Lys Tyr
           865                 870                 875                 880

Arg Phe Asp Asn Leu Asp Ser Gly Lys Tyr Lys Val Ile Phe Glu Lys
                           885                 890                 895

Pro Ala Gly Leu Thr Gln Thr Val Thr Asn Thr Thr Glu Asp Asp Lys
                           900                 905                 910

Asp Ala Asp Gly Gly Glu Val Asp Val Thr Ile Thr Asp His Asp Asp
                           915                 920                 925

Phe Thr Leu Asp Asn Gly Tyr Phe Glu Glu Asp Thr Ser Asp Ser Asp
                           930                 935                 940

Ser Asp Ser Asp Ser Asp Ser Asp Ser Asp Ser Asp Ser Asp Ser Asp
           945                 950                 955                 960

Ser Asp Ser Asp Ser Asp Ser Asp Ser Asp Ser Asp Ser Asp Ser Asp
                           965                 970                 975

Ser Asp Ser Asp Ser Asp Ser Asp Ser Asp Ser Asp Ser Asp Ser Asp
                           980                 985                 990

Ser Asp Ser Asp Ser Asp Ser Asp Ser Asp Ser Asp Ser Asp Ser Asp
                           995                 1000                1005

Ser Asp Ser Asp Ser Asp Ser Asp Ser Asp Ser Asp Ser Asp Ser Asp
                           1010                1015                1020

Ser Asp Ser Asp Ser Asp Ser Asp Ser Asp Ser Asp Ser Asp Ser Asp
           1025                1030                1035                1040

Ser Asp Ser Asp Ser Asp Ser Asp Ser Asp Ser Asp Ser Asp Ser Asp
                           1045                1050                1055
```

```
Ser Asp Ser Asp Ser Asp Ser Asp Ser Asp Ser Asp
            1060                1065                1070

Ser Asp Ser Asp Ser Asp Ser Asp Ser Asp Ser Asp
        1075                1080                1085

Ser Asp Ser Asp Ser Asp Ser Asp Ser Asp Ser Asp
            1090                1095                1100

Ser Asp Ala Gly Lys His Thr Pro Val Lys Pro Met Ser Thr Thr Lys
1105                1110                1115                1120

Asp His His Asn Lys Ala Lys Ala Leu Pro Glu Thr Gly Ser Glu Asn
                1125                1130                1135

Asn Gly Ser Asn Asn Ala Thr Leu Phe Gly Gly Leu Phe Ala Ala Leu
            1140                1145                1150

Gly Ser Leu Leu Leu Phe Gly Arg Arg Lys Lys Gln Asn Lys
            1155                1160                1165

<210> SEQ ID NO 9
<211> LENGTH: 580
<212> TYPE: PRT
<213> ORGANISM: Staphylococcus aureus

<400> SEQUENCE: 9

Ala Glu Asn Thr Ser Thr Glu Asn Ala Lys Gln Asp Asp Ala Thr Thr
1               5                   10                  15

Ser Asp Asn Lys Glu Val Val Ser Glu Thr Glu Asn Asn Ser Thr Thr
                20                  25                  30

Glu Asn Asn Ser Thr Asn Pro Ile Lys Lys Glu Thr Asn Thr Asp Ser
            35                  40                  45

Gln Pro Glu Ala Lys Lys Glu Ser Thr Ser Ser Thr Gln Lys Gln
    50                  55                  60

Gln Asn Asn Val Thr Ala Thr Thr Glu Thr Lys Pro Gln Asn Ile Glu
65                  70                  75                  80

Lys Glu Asn Val Lys Pro Ser Thr Asp Lys Thr Ala Thr Glu Asp Thr
                85                  90                  95

Ser Val Ile Leu Glu Glu Lys Lys Ala Pro Asn Asn Thr Asn Asn Asp
            100                 105                 110

Val Thr Thr Lys Pro Ser Thr Ser Glu Pro Ser Thr Ser Glu Ile Gln
        115                 120                 125

Thr Lys Pro Thr Thr Pro Gln Glu Ser Thr Asn Ile Glu Asn Ser Gln
    130                 135                 140

Pro Gln Pro Thr Pro Ser Lys Val Asp Asn Gln Val Thr Asp Ala Thr
145                 150                 155                 160

Asn Pro Lys Glu Pro Val Asn Val Ser Lys Glu Glu Leu Lys Asn Asn
                165                 170                 175

Pro Glu Lys Leu Lys Glu Leu Val Arg Asn Asp Ser Asn Thr Asp His
            180                 185                 190

Ser Thr Lys Pro Val Ala Thr Ala Pro Thr Ser Val Ala Pro Lys Arg
        195                 200                 205

Val Asn Ala Lys Met Arg Phe Ala Val Ala Gln Pro Ala Ala Val Ala
    210                 215                 220

Ser Asn Asn Val Asn Asp Leu Ile Lys Val Thr Lys Gln Thr Ile Lys
225                 230                 235                 240

Val Gly Asp Gly Lys Asp Asn Val Ala Ala His Asp Gly Lys Asp
                245                 250                 255

Ile Glu Tyr Asp Thr Glu Phe Thr Ile Asp Asn Lys Val Lys Lys Gly
```

```
            260                 265                 270
Asp Thr Met Thr Ile Asn Tyr Asp Lys Asn Val Ile Pro Ser Asp Leu
            275                 280                 285

Thr Asp Lys Asn Asp Pro Ile Asp Ile Thr Asp Pro Ser Gly Glu Val
            290                 295                 300

Ile Ala Lys Gly Thr Phe Asp Lys Ala Thr Lys Gln Ile Thr Tyr Thr
305                 310                 315                 320

Phe Thr Asp Tyr Val Asp Lys Tyr Glu Asp Ile Lys Ser Arg Leu Thr
                325                 330                 335

Leu Tyr Ser Tyr Ile Asp Lys Lys Thr Val Pro Asn Glu Thr Ser Leu
            340                 345                 350

Asn Leu Thr Phe Ala Thr Ala Gly Lys Glu Thr Ser Gln Asn Val Thr
            355                 360                 365

Val Asp Tyr Gln Asp Pro Met Val His Gly Asp Ser Asn Ile Gln Ser
            370                 375                 380

Ile Phe Thr Lys Leu Asp Glu Asp Lys Gln Thr Ile Glu Gln Gln Ile
385                 390                 395                 400

Tyr Val Asn Pro Leu Lys Lys Ser Ala Thr Asn Thr Lys Val Asp Ile
                405                 410                 415

Ala Gly Ser Gln Val Asp Asp Tyr Gly Asn Ile Lys Leu Gly Asn Gly
            420                 425                 430

Ser Thr Ile Ile Asp Gln Asn Thr Glu Ile Lys Val Tyr Lys Val Asn
            435                 440                 445

Ser Asp Gln Gln Leu Pro Gln Ser Asn Arg Ile Tyr Asp Phe Ser Gln
            450                 455                 460

Tyr Glu Asp Val Thr Ser Gln Phe Asp Asn Lys Lys Ser Phe Ser Asn
465                 470                 475                 480

Asn Val Ala Thr Leu Asp Phe Gly Asp Ile Asn Ser Ala Tyr Ile Ile
                485                 490                 495

Lys Val Val Ser Lys Tyr Thr Pro Thr Ser Asp Gly Glu Leu Asp Ile
            500                 505                 510

Ala Gln Gly Thr Ser Met Arg Thr Thr Asp Lys Tyr Gly Tyr Tyr Asn
            515                 520                 525

Tyr Ala Gly Tyr Ser Asn Phe Ile Val Thr Ser Asn Asp Thr Gly Gly
            530                 535                 540

Gly Asp Gly Thr Val Lys Pro Glu Glu Lys Leu Tyr Lys Ile Gly Asp
545                 550                 555                 560

Tyr Val Trp Glu Asp Val Asp Lys Asp Gly Val Gln Gly Thr Asp Ser
                565                 570                 575

Lys Glu Lys Pro
            580

<210> SEQ ID NO 10
<211> LENGTH: 995
<212> TYPE: PRT
<213> ORGANISM: Staphylococcus aureus

<400> SEQUENCE: 10

Met Asn Asn Lys Lys Thr Ala Thr Asn Arg Lys Gly Met Ile Pro Asn
1               5                   10                  15

Arg Leu Asn Lys Phe Ser Ile Arg Lys Tyr Ser Val Gly Thr Ala Ser
                20                  25                  30

Ile Leu Val Gly Thr Thr Leu Ile Phe Gly Leu Ser Gly His Glu Ala
            35                  40                  45
```

```
Lys Ala Ala Glu His Thr Asn Gly Glu Leu Asn Gln Ser Lys Asn Glu
 50                  55                  60

Thr Thr Ala Pro Ser Glu Asn Lys Thr Thr Lys Lys Val Asp Ser Arg
 65                  70                  75                  80

Gln Leu Lys Asp Asn Thr Gln Thr Ala Thr Ala Asp Gln Pro Lys Val
                 85                  90                  95

Thr Met Ser Asp Ser Ala Thr Val Lys Glu Thr Ser Ser Asn Met Gln
            100                 105                 110

Ser Pro Gln Asn Ala Thr Ala Asn Gln Ser Thr Thr Lys Thr Ser Asn
        115                 120                 125

Val Thr Thr Asn Asp Lys Ser Ser Thr Thr Tyr Ser Asn Glu Thr Asp
130                 135                 140

Lys Ser Asn Leu Thr Gln Ala Lys Asp Val Ser Thr Thr Pro Lys Thr
145                 150                 155                 160

Thr Thr Ile Lys Pro Arg Thr Leu Asn Arg Met Ala Val Asn Thr Val
                165                 170                 175

Ala Ala Pro Gln Gln Gly Thr Asn Val Asn Asp Lys Val His Phe Ser
            180                 185                 190

Asn Ile Asp Ile Ala Ile Asp Lys Gly His Val Asn Gln Thr Thr Gly
        195                 200                 205

Lys Thr Glu Phe Trp Ala Thr Ser Ser Asp Val Leu Lys Leu Lys Ala
210                 215                 220

Asn Tyr Thr Ile Asp Asp Ser Val Lys Glu Gly Asp Thr Phe Thr Phe
225                 230                 235                 240

Lys Tyr Gly Gln Tyr Phe Arg Pro Gly Ser Val Arg Leu Pro Ser Gln
                245                 250                 255

Thr Gln Asn Leu Tyr Asn Ala Gln Gly Asn Ile Ile Ala Lys Gly Ile
            260                 265                 270

Tyr Asp Ser Thr Thr Asn Thr Thr Tyr Thr Phe Thr Asn Tyr Val
        275                 280                 285

Asp Gln Tyr Thr Asn Val Arg Gly Ser Phe Glu Gln Val Ala Phe Ala
290                 295                 300

Lys Arg Lys Asn Ala Thr Thr Asp Lys Thr Ala Tyr Lys Met Glu Val
305                 310                 315                 320

Thr Leu Gly Asn Asp Thr Tyr Ser Glu Glu Ile Ile Val Asp Tyr Gly
                325                 330                 335

Asn Lys Lys Ala Gln Pro Leu Ile Ser Ser Thr Asn Tyr Ile Asn Asn
            340                 345                 350

Glu Asp Leu Ser Arg Asn Met Thr Ala Tyr Val Asn Gln Pro Lys Asn
        355                 360                 365

Thr Tyr Thr Lys Gln Thr Phe Val Thr Asn Leu Thr Gly Tyr Lys Phe
370                 375                 380

Asn Pro Asn Ala Lys Asn Phe Lys Ile Tyr Glu Val Thr Asp Gln Asn
385                 390                 395                 400

Gln Phe Val Asp Ser Phe Thr Pro Asp Thr Ser Lys Leu Lys Asp Val
                405                 410                 415

Thr Asp Gln Phe Asp Val Ile Tyr Ser Asn Asp Asn Lys Thr Ala Thr
            420                 425                 430

Val Asp Leu Met Lys Gly Gln Thr Ser Ser Asn Lys Gln Tyr Ile Ile
        435                 440                 445

Gln Gln Val Ala Tyr Pro Asp Asn Ser Ser Thr Asp Asn Gly Lys Ile
450                 455                 460

Asp Tyr Thr Leu Asp Thr Asp Lys Thr Lys Tyr Ser Trp Ser Asn Ser
```

```
                465                 470                 475                 480

Tyr Ser Asn Val Asn Gly Ser Thr Ala Asn Gly Asp Gln Lys Lys
                    485                 490                 495

Tyr Asn Leu Gly Asp Tyr Val Trp Glu Asp Thr Asn Lys Asp Gly Lys
                500                 505                 510

Gln Asp Ala Asn Glu Lys Gly Ile Lys Gly Val Tyr Val Ile Leu Lys
                515                 520                 525

Asp Ser Asn Gly Lys Glu Leu Asp Arg Thr Thr Thr Asp Glu Asn Gly
530                 535                 540

Lys Tyr Gln Phe Thr Gly Leu Ser Asn Gly Thr Tyr Ser Val Glu Phe
545                 550                 555                 560

Ser Thr Pro Ala Gly Tyr Thr Pro Thr Thr Ala Asn Val Gly Thr Asp
                565                 570                 575

Asp Ala Val Asp Ser Asp Gly Leu Thr Thr Thr Gly Val Ile Lys Asp
                580                 585                 590

Ala Asp Asn Met Thr Leu Asp Ser Gly Phe Tyr Lys Thr Pro Lys Tyr
                595                 600                 605

Ser Leu Gly Asp Tyr Val Trp Tyr Asp Ser Asn Lys Asp Gly Lys Gln
                610                 615                 620

Asp Ser Thr Glu Lys Gly Ile Lys Gly Val Lys Val Thr Leu Gln Asn
625                 630                 635                 640

Glu Lys Gly Glu Val Ile Gly Thr Thr Glu Thr Asp Glu Asn Gly Lys
                645                 650                 655

Tyr Arg Phe Asp Asn Leu Asp Ser Gly Lys Tyr Lys Val Ile Phe Glu
                660                 665                 670

Lys Pro Ala Gly Leu Thr Gln Thr Gly Thr Asn Thr Thr Glu Asp Asp
                675                 680                 685

Lys Asp Ala Asp Gly Gly Glu Val Asp Val Thr Ile Thr Asp His Asp
                690                 695                 700

Asp Phe Thr Leu Asp Asn Gly Tyr Tyr Glu Glu Thr Ser Asp Ser
705                 710                 715                 720

Asp Ser Asp Ser Asp Ser Asp Ser Asp Ser Asp Ser Asp Ser
                725                 730                 735

Asp Ser Asp Ser Asp Ser Asp Ser Asp Ser Asp Ser Asp Ser
                740                 745                 750

Asp Ser Asp Ser Asp Ser Asp Ser Asp Ser Asp Ser Asp Ser
                755                 760                 765

Asp Ser Asp Ser Asp Ser Asp Ser Asp Ser Asp Ser Asp Ser
770                 775                 780

Asp Ser Asp Ser Asp Ser Asp Ser Asp Ser Asp Ser Asp Ser
785                 790                 795                 800

Asp Ser Asp Ser Asp Ser Asp Ser Asp Ser Asp Ser Asp Ser
                805                 810                 815

Asp Ser Asp Ser Asp Ser Asp Ser Asp Ser Asp Ser Asp Ser
                820                 825                 830

Asp Ser Asp Ser Asp Ser Asp Ser Asp Ser Asp Ser
                835                 840                 845

Asp Ser Asp Ser Asp Ser Asp Ser Asn Ser Asp Ser Asp Ser
                850                 855                 860

Asp Ser Asp Ser Asp Ser Asp Ser Asp Ser Asp Ser Asp Ser
865                 870                 875                 880

Asp Ser Asp Ser Asp Ser Asp Ser Asp Ser Asp Ser Asp Ser
                885                 890                 895
```

```
Asp Ser Asp Ser Asp Ser Asp Ser Asp Ser Asp Ser
            900                 905                 910
Asp Ser Asp Ser Asp Ser Asp Ser Asn Asp Ser Asp Ser
            915                 920                 925
Asp Ser Asp Ser Asp Ser Ala Gly Lys His Thr Pro Ala Lys Pro
            930                 935                 940
Met Ser Thr Val Lys Asp Gln His Lys Thr Ala Lys Ala Leu Pro Glu
945                 950                 955                 960
Thr Gly Ser Glu Asn Asn Ser Asn Asn Gly Thr Leu Phe Gly Gly
                965                 970                 975
Leu Phe Ala Ala Leu Gly Ser Leu Leu Leu Phe Gly Arg Arg Lys Lys
            980                 985                 990
Gln Asn Lys
        995

<210> SEQ ID NO 11
<211> LENGTH: 468
<212> TYPE: PRT
<213> ORGANISM: Staphylococcus aureus

<400> SEQUENCE: 11

Ala Glu His Thr Asn Gly Glu Leu Asn Gln Ser Lys Asn Glu Thr Thr
1               5                   10                  15
Ala Pro Ser Glu Asn Lys Thr Thr Lys Lys Val Asp Ser Arg Gln Leu
            20                  25                  30
Lys Asp Asn Thr Gln Thr Ala Thr Ala Asp Gln Pro Lys Val Thr Met
        35                  40                  45
Ser Asp Ser Ala Thr Val Lys Glu Thr Ser Ser Asn Met Gln Ser Pro
    50                  55                  60
Gln Asn Ala Thr Ala Asn Gln Ser Thr Thr Lys Thr Ser Asn Val Thr
65                  70                  75                  80
Thr Asn Asp Lys Ser Ser Thr Thr Tyr Ser Asn Glu Thr Asp Lys Ser
                85                  90                  95
Asn Leu Thr Gln Ala Lys Asp Val Ser Thr Thr Pro Lys Thr Thr Thr
            100                 105                 110
Ile Lys Pro Arg Thr Leu Asn Arg Met Ala Val Asn Thr Val Ala Ala
        115                 120                 125
Pro Gln Gln Gly Thr Asn Val Asn Asp Lys Val His Phe Ser Asn Ile
    130                 135                 140
Asp Ile Ala Ile Asp Lys Gly His Val Asn Gln Thr Thr Gly Lys Thr
145                 150                 155                 160
Glu Phe Trp Ala Thr Ser Ser Asp Val Leu Lys Leu Lys Ala Asn Tyr
                165                 170                 175
Thr Ile Asp Asp Ser Val Lys Glu Gly Asp Thr Phe Thr Phe Lys Tyr
            180                 185                 190
Gly Gln Tyr Phe Arg Pro Gly Ser Val Arg Leu Pro Ser Gln Thr Gln
        195                 200                 205
Asn Leu Tyr Asn Ala Gln Gly Asn Ile Ile Ala Lys Gly Ile Tyr Asp
    210                 215                 220
Ser Thr Thr Asn Thr Thr Thr Tyr Thr Phe Thr Asn Tyr Val Asp Gln
225                 230                 235                 240
Tyr Thr Asn Val Arg Gly Ser Phe Glu Gln Val Ala Phe Ala Lys Arg
                245                 250                 255
Lys Asn Ala Thr Thr Asp Lys Thr Ala Tyr Lys Met Glu Val Thr Leu
```

```
                    260                 265                 270
Gly Asn Asp Thr Tyr Ser Glu Glu Ile Ile Val Asp Tyr Gly Asn Lys
                275                 280                 285

Lys Ala Gln Pro Leu Ile Ser Ser Thr Asn Tyr Ile Asn Asn Glu Asp
            290                 295                 300

Leu Ser Arg Asn Met Thr Ala Tyr Val Asn Gln Pro Lys Asn Thr Tyr
305                 310                 315                 320

Thr Lys Gln Thr Phe Val Thr Asn Leu Thr Gly Tyr Lys Phe Asn Pro
                325                 330                 335

Asn Ala Lys Asn Phe Lys Ile Tyr Glu Val Thr Asp Gln Asn Gln Phe
            340                 345                 350

Val Asp Ser Phe Thr Pro Asp Thr Ser Lys Leu Lys Asp Val Thr Asp
            355                 360                 365

Gln Phe Asp Val Ile Tyr Ser Asn Asp Asn Lys Thr Ala Thr Val Asp
            370                 375                 380

Leu Met Lys Gly Gln Thr Ser Ser Asn Lys Gln Tyr Ile Ile Gln Gln
385                 390                 395                 400

Val Ala Tyr Pro Asp Asn Ser Ser Thr Asp Asn Gly Lys Ile Asp Tyr
                405                 410                 415

Thr Leu Asp Thr Asp Lys Thr Lys Tyr Ser Trp Ser Asn Ser Tyr Ser
            420                 425                 430

Asn Val Asn Gly Ser Ser Thr Ala Asn Gly Asp Gln Lys Lys Tyr Asn
            435                 440                 445

Leu Gly Asp Tyr Val Trp Glu Asp Thr Asn Lys Asp Gly Lys Gln Asp
            450                 455                 460

Ala Asn Glu Lys
465

<210> SEQ ID NO 12
<211> LENGTH: 635
<212> TYPE: PRT
<213> ORGANISM: Staphylococcus aureus

<400> SEQUENCE: 12

Met Ala Lys Tyr Arg Gly Lys Pro Phe Gln Leu Tyr Val Lys Leu Ser
1               5                   10                  15

Cys Ser Thr Met Met Ala Thr Ser Ile Ile Leu Thr Asn Ile Leu Pro
            20                  25                  30

Tyr Asp Ala Gln Ala Ala Ser Glu Lys Asp Thr Glu Ile Thr Lys Glu
        35                  40                  45

Ile Leu Ser Lys Gln Asp Leu Asp Lys Val Asp Lys Ala Ile Arg
    50                  55                  60

Gln Ile Glu Gln Leu Lys Gln Leu Ser Ala Ser Ser Lys Glu His Tyr
65                  70                  75                  80

Lys Ala Gln Leu Asn Glu Ala Lys Thr Ala Ser Gln Ile Asp Glu Ile
                85                  90                  95

Ile Lys Arg Ala Asn Glu Leu Asp Ser Lys Asp Asn Lys Ser Ser His
            100                 105                 110

Thr Glu Met Asn Gly Gln Ser Asp Ile Asp Ser Lys Leu Asp Gln Leu
        115                 120                 125

Leu Lys Asp Leu Asn Glu Val Ser Ser Asn Val Asp Arg Gly Gln Gln
    130                 135                 140

Ser Gly Glu Asp Asp Leu Asn Ala Met Lys Asn Asp Met Ser Gln Thr
145                 150                 155                 160
```

-continued

```
Ala Thr Thr Lys His Gly Glu Lys Asp Asp Lys Asn Asp Glu Ala Met
                165                 170                 175
Val Asn Lys Ala Leu Glu Asp Leu Asp His Leu Asn Gln Gln Ile His
            180                 185                 190
Lys Ser Lys Asp Ala Ser Lys Asp Thr Ser Glu Asp Pro Ala Val Ser
        195                 200                 205
Thr Thr Asp Asn Asn His Glu Val Ala Lys Thr Pro Asn Asn Asp Gly
    210                 215                 220
Ser Gly His Val Val Leu Asn Lys Phe Leu Ser Asn Glu Glu Asn Gln
225                 230                 235                 240
Ser His Ser Asn Arg Leu Thr Asp Lys Leu Gln Gly Ser Asp Lys Ile
                245                 250                 255
Asn His Ala Met Ile Glu Lys Leu Ala Lys Ser Asn Ala Ser Thr Gln
            260                 265                 270
His Tyr Thr Tyr His Lys Leu Asn Thr Leu Gln Ser Leu Asp Gln Arg
        275                 280                 285
Ile Ala Asn Thr Gln Leu Pro Lys Asn Gln Lys Ser Asp Leu Met Ser
    290                 295                 300
Glu Val Asn Lys Thr Lys Glu Arg Ile Lys Ser Gln Arg Asn Ile Ile
305                 310                 315                 320
Leu Glu Glu Leu Ala Arg Thr Asp Asp Lys Lys Tyr Ala Thr Gln Ser
                325                 330                 335
Ile Leu Glu Ser Ile Phe Asn Lys Asp Glu Ala Val Lys Ile Leu Lys
            340                 345                 350
Asp Ile Arg Val Asp Gly Lys Thr Asp Gln Gln Ile Ala Asp Gln Ile
        355                 360                 365
Thr Arg His Ile Asp Gln Leu Ser Leu Thr Thr Ser Asp Asp Leu Leu
    370                 375                 380
Thr Ser Leu Ile Asp Gln Ser Gln Asp Lys Ser Leu Leu Ile Ser Gln
385                 390                 395                 400
Ile Leu Gln Thr Lys Leu Gly Lys Ala Glu Ala Asp Lys Leu Ala Lys
                405                 410                 415
Asp Trp Thr Asn Lys Gly Leu Ser Asn Arg Gln Ile Val Asp Gln Leu
            420                 425                 430
Lys Lys His Phe Ala Ser Thr Gly Asp Thr Ser Ser Asp Asp Ile Leu
        435                 440                 445
Lys Ala Ile Leu Asn Asn Ala Lys Asp Lys Lys Gln Ala Ile Glu Thr
    450                 455                 460
Ile Leu Ala Thr Arg Ile Glu Arg Gln Lys Ala Lys Leu Leu Ala Asp
465                 470                 475                 480
Leu Ile Thr Lys Ile Glu Thr Asp Gln Asn Lys Ile Phe Asn Leu Val
                485                 490                 495
Lys Ser Ala Leu Asn Gly Lys Ala Asp Asp Leu Leu Asn Leu Gln Lys
            500                 505                 510
Arg Leu Asn Gln Thr Lys Lys Asp Ile Asp Tyr Ile Leu Ser Pro Ile
        515                 520                 525
Val Asn Arg Pro Ser Leu Leu Asp Arg Leu Asn Lys Asn Gly Lys Thr
    530                 535                 540
Thr Asp Leu Asn Lys Leu Ala Asn Leu Met Asn Gln Gly Ser Asp Leu
545                 550                 555                 560
Leu Asp Ser Ile Pro Asp Ile Pro Thr Pro Lys Pro Glu Lys Thr Leu
                565                 570                 575
Thr Leu Gly Lys Gly Asn Gly Leu Leu Ser Gly Leu Leu Asn Ala Asp
```

```
                580             585             590
Gly Asn Val Ser Leu Pro Lys Ala Gly Glu Thr Ile Lys Glu His Trp
            595                 600             605

Leu Pro Ile Ser Val Ile Val Gly Ala Met Gly Val Leu Met Ile Trp
        610                 615             620

Leu Ser Arg Arg Asn Lys Leu Lys Asn Lys Ala
625                 630             635

<210> SEQ ID NO 13
<211> LENGTH: 340
<212> TYPE: PRT
<213> ORGANISM: Staphylococcus aureus

<400> SEQUENCE: 13

Met Lys Lys Lys Leu Leu Val Leu Thr Met Ser Thr Leu Phe Ala Thr
1               5                   10                  15

Gln Ile Met Asn Ser Asn His Ala Lys Ala Ser Val Thr Glu Ser Val
            20                  25                  30

Asp Lys Lys Phe Val Val Pro Glu Ser Gly Ile Asn Lys Ile Ile Pro
        35                  40                  45

Ala Tyr Asp Glu Phe Lys Asn Ser Pro Lys Val Asn Val Ser Asn Leu
    50                  55                  60

Thr Asp Asn Lys Asn Phe Val Ala Ser Glu Asp Lys Leu Asn Lys Ile
65                  70                  75                  80

Ala Asp Ser Ser Ala Ala Ser Lys Ile Val Asp Lys Asn Phe Val Val
                85                  90                  95

Pro Glu Ser Lys Leu Gly Asn Ile Val Pro Glu Tyr Lys Glu Ile Asn
            100                 105                 110

Asn Arg Val Asn Val Ala Thr Asn Asn Pro Ala Ser Gln Gln Val Asp
        115                 120                 125

Lys His Phe Val Ala Lys Gly Pro Glu Val Asn Arg Phe Ile Thr Gln
    130                 135                 140

Asn Lys Val Asn His His Phe Ile Thr Thr Gln Thr His Tyr Lys Lys
145                 150                 155                 160

Val Ile Thr Ser Tyr Lys Ser Thr His Val His Lys His Val Asn His
                165                 170                 175

Ala Lys Asp Ser Ile Asn Lys His Phe Ile Val Lys Pro Ser Glu Ser
            180                 185                 190

Pro Arg Tyr Thr His Pro Ser Gln Ser Leu Ile Ile Lys His His Phe
        195                 200                 205

Ala Val Pro Gly Tyr His Ala His Lys Phe Val Thr Pro Gly His Ala
    210                 215                 220

Ser Ile Lys Ile Asn His Phe Cys Val Val Pro Gln Ile Asn Ser Phe
225                 230                 235                 240

Lys Val Ile Pro Pro Tyr Gly His Asn Ser His Arg Met His Val Pro
                245                 250                 255

Ser Phe Gln Asn Asn Thr Thr Ala Thr His Gln Asn Ala Lys Val Asn
            260                 265                 270

Lys Ala Tyr Asp Tyr Lys Tyr Phe Tyr Ser Tyr Lys Val Val Lys Gly
        275                 280                 285

Val Lys Lys Tyr Phe Ser Phe Ser Gln Ser Asn Gly Tyr Lys Ile Gly
    290                 295                 300

Lys Pro Ser Leu Asn Ile Lys Asn Val Asn Tyr Gln Tyr Ala Val Pro
305                 310                 315                 320
```

```
Ser Tyr Ser Pro Thr His Tyr Val Pro Glu Phe Lys Gly Ser Leu Pro
                325                 330                 335

Ala Pro Arg Val
            340

<210> SEQ ID NO 14
<211> LENGTH: 306
<212> TYPE: PRT
<213> ORGANISM: Staphylococcus aureus

<400> SEQUENCE: 14

Lys Phe Val Val Pro Glu Ser Gly Ile Asn Lys Ile Ile Pro Ala Tyr
1               5                   10                  15

Asp Glu Phe Lys Asn Ser Pro Lys Val Asn Val Ser Asn Leu Thr Asp
            20                  25                  30

Asn Lys Asn Phe Val Ala Ser Glu Asp Lys Leu Asn Lys Ile Ala Asp
        35                  40                  45

Ser Ser Ala Ala Ser Lys Ile Val Asp Lys Asn Phe Val Val Pro Glu
    50                  55                  60

Ser Lys Leu Gly Asn Ile Val Pro Glu Tyr Lys Glu Ile Asn Asn Arg
65                  70                  75                  80

Val Asn Val Ala Thr Asn Asn Pro Ala Ser Gln Gln Val Asp Lys His
                85                  90                  95

Phe Val Ala Lys Gly Pro Glu Val Asn Arg Phe Ile Thr Gln Asn Lys
            100                 105                 110

Val Asn His His Phe Ile Thr Thr Gln Thr His Tyr Lys Lys Val Ile
        115                 120                 125

Thr Ser Tyr Lys Ser Thr His Val Lys His Val Asn His Ala Lys
130                 135                 140

Asp Ser Ile Asn Lys His Phe Ile Val Lys Pro Ser Glu Ser Pro Arg
145                 150                 155                 160

Tyr Thr His Pro Ser Gln Ser Leu Ile Ile Lys His His Phe Ala Val
                165                 170                 175

Pro Gly Tyr His Ala His Lys Phe Val Thr Pro Gly His Ala Ser Ile
            180                 185                 190

Lys Ile Asn His Phe Cys Val Val Pro Gln Ile Asn Ser Phe Lys Val
        195                 200                 205

Ile Pro Pro Tyr Gly His Asn Ser His Arg Met His Val Pro Ser Phe
    210                 215                 220

Gln Asn Asn Thr Thr Ala Thr His Gln Asn Ala Lys Val Asn Lys Ala
225                 230                 235                 240

Tyr Asp Tyr Lys Tyr Phe Tyr Ser Tyr Lys Val Val Lys Gly Val Lys
                245                 250                 255

Lys Tyr Phe Ser Phe Ser Gln Ser Asn Gly Tyr Lys Ile Gly Lys Pro
            260                 265                 270

Ser Leu Asn Ile Lys Asn Val Asn Tyr Gln Tyr Ala Val Pro Ser Tyr
        275                 280                 285

Ser Pro Thr His Tyr Val Pro Glu Phe Lys Gly Ser Leu Pro Ala Pro
    290                 295                 300

Arg Val
305

<210> SEQ ID NO 15
<211> LENGTH: 308
<212> TYPE: PRT
<213> ORGANISM: Staphylococcus aureus
```

<400> SEQUENCE: 15

```
Ser Val Thr Glu Ser Val Asp Lys Lys Phe Val Val Pro Glu Ser Gly
1               5                   10                  15

Ile Asn Lys Ile Ile Pro Ala Tyr Asp Glu Phe Lys Asn Ser Pro Lys
            20                  25                  30

Val Asn Val Ser Asn Leu Thr Asp Asn Lys Asn Phe Val Ala Ser Glu
        35                  40                  45

Asp Lys Leu Asn Lys Ile Ala Asp Ser Ser Ala Ala Ser Lys Ile Val
    50                  55                  60

Asp Lys Asn Phe Val Val Pro Glu Ser Lys Leu Gly Asn Ile Val Pro
65                  70                  75                  80

Glu Tyr Lys Glu Ile Asn Asn Arg Val Asn Val Ala Thr Asn Asn Pro
                85                  90                  95

Ala Ser Gln Gln Val Asp Lys His Phe Val Ala Lys Gly Pro Glu Val
            100                 105                 110

Asn Arg Phe Ile Thr Gln Asn Lys Val Asn His Phe Ile Thr Thr
        115                 120                 125

Gln Thr His Tyr Lys Lys Val Ile Thr Ser Tyr Lys Ser Thr His Val
    130                 135                 140

His Lys His Val Asn His Ala Lys Asp Ser Ile Asn Lys His Phe Ile
145                 150                 155                 160

Val Lys Pro Ser Glu Ser Pro Arg Tyr Thr His Pro Ser Gln Ser Leu
                165                 170                 175

Ile Ile Lys His His Phe Ala Val Pro Gly Tyr His Ala His Lys Phe
            180                 185                 190

Val Thr Pro Gly His Ala Ser Ile Lys Ile Asn His Phe Cys Val Val
        195                 200                 205

Pro Gln Ile Asn Ser Phe Lys Val Ile Pro Tyr Gly His Asn Ser
    210                 215                 220

His Arg Met His Val Pro Ser Phe Gln Asn Asn Thr Thr Ala Thr His
225                 230                 235                 240

Gln Asn Ala Lys Val Asn Lys Ala Tyr Asp Tyr Lys Tyr Phe Tyr Ser
                245                 250                 255

Tyr Lys Val Val Lys Gly Val Lys Lys Tyr Phe Ser Phe Ser Gln Ser
            260                 265                 270

Asn Gly Tyr Lys Ile Gly Lys Pro Ser Leu Asn Ile Lys Asn Val Asn
        275                 280                 285

Tyr Gln Tyr Ala Val Pro Ser Tyr Ser Pro Thr His Tyr Val Pro Glu
    290                 295                 300

Phe Lys Gly Ser
305
```

<210> SEQ ID NO 16
<211> LENGTH: 300
<212> TYPE: PRT
<213> ORGANISM: Staphylococcus aureus

<400> SEQUENCE: 16

```
Lys Phe Val Val Pro Glu Ser Gly Ile Asn Lys Ile Ile Pro Ala Tyr
1               5                   10                  15

Asp Glu Phe Lys Asn Ser Pro Lys Val Asn Val Ser Asn Leu Thr Asp
            20                  25                  30

Asn Lys Asn Phe Val Ala Ser Glu Asp Lys Leu Asn Lys Ile Ala Asp
        35                  40                  45
```

Ser Ser Ala Ala Ser Lys Ile Val Asp Lys Asn Phe Val Val Pro Glu
        50                  55                  60

Ser Lys Leu Gly Asn Ile Val Pro Glu Tyr Lys Glu Ile Asn Asn Arg
65                  70                  75                  80

Val Asn Val Ala Thr Asn Asn Pro Ala Ser Gln Gln Val Asp Lys His
                85                  90                  95

Phe Val Ala Lys Gly Pro Glu Val Asn Arg Phe Ile Thr Gln Asn Lys
                100                 105                 110

Val Asn His His Phe Ile Thr Thr Gln Thr His Tyr Lys Lys Val Ile
            115                 120                 125

Thr Ser Tyr Lys Ser Thr His Val His Lys His Val Asn His Ala Lys
        130                 135                 140

Asp Ser Ile Asn Lys His Phe Ile Val Lys Pro Ser Glu Ser Pro Arg
145                 150                 155                 160

Tyr Thr His Pro Ser Gln Ser Leu Ile Ile Lys His His Phe Ala Val
                165                 170                 175

Pro Gly Tyr His Ala His Lys Phe Val Thr Pro Gly His Ala Ser Ile
                180                 185                 190

Lys Ile Asn His Phe Cys Val Val Pro Gln Ile Asn Ser Phe Lys Val
            195                 200                 205

Ile Pro Pro Tyr Gly His Asn Ser His Arg Met His Val Pro Ser Phe
210                 215                 220

Gln Asn Asn Thr Thr Ala Thr His Gln Asn Ala Lys Val Asn Lys Ala
225                 230                 235                 240

Tyr Asp Tyr Lys Tyr Phe Tyr Ser Tyr Lys Val Val Lys Gly Val Lys
                245                 250                 255

Lys Tyr Phe Ser Phe Ser Gln Ser Asn Gly Tyr Lys Ile Gly Lys Pro
                260                 265                 270

Ser Leu Asn Ile Lys Asn Val Asn Tyr Gln Tyr Ala Val Pro Ser Tyr
            275                 280                 285

Ser Pro Thr His Tyr Val Pro Glu Phe Lys Gly Ser
                290                 295                 300

<210> SEQ ID NO 17
<211> LENGTH: 121
<212> TYPE: PRT
<213> ORGANISM: Staphylococcus aureus

<400> SEQUENCE: 17

Ser Val Thr Glu Ser Val Asp Lys Lys Phe Val Pro Glu Ser Gly
1               5                   10                  15

Ile Asn Lys Ile Ile Pro Ala Tyr Asp Glu Phe Lys Asn Ser Pro Lys
                20                  25                  30

Val Asn Val Ser Asn Leu Thr Asp Asn Lys Asn Phe Val Ala Ser Glu
            35                  40                  45

Asp Lys Leu Asn Lys Ile Ala Asp Ser Ser Ala Ala Ser Lys Ile Val
        50                  55                  60

Asp Lys Asn Phe Val Val Pro Glu Ser Lys Leu Gly Asn Ile Val Pro
65                  70                  75                  80

Glu Tyr Lys Glu Ile Asn Asn Arg Val Asn Val Ala Thr Asn Asn Pro
                85                  90                  95

Ala Ser Gln Gln Val Asp Lys His Phe Val Ala Lys Gly Pro Glu Val
                100                 105                 110

Asn Arg Phe Ile Thr Gln Asn Lys Val

<210> SEQ ID NO 18
<211> LENGTH: 1349
<212> TYPE: PRT
<213> ORGANISM: Staphylococcus aureus

<400> SEQUENCE: 18

```
Met Leu Asn Arg Glu Asn Lys Thr Ala Ile Thr Arg Lys Gly Met Val
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Ser Thr Asn Lys Glu Leu Asn Glu Ala Thr
50                  55                  60

Thr Ser Ala Ser Asp Asn Gln Ser Ser Asp Lys Val Asp Met Gln Gln
65                  70                  75                  80

Leu Asn Gln Glu Asp Asn Thr Lys Asn Asp Asn Gln Lys Glu Met Val
                85                  90                  95

Ser Ser Gln Gly Asn Glu Thr Thr Ser Asn Gly Asn Lys Leu Ile Glu
            100                 105                 110

Lys Glu Ser Val Gln Ser Thr Thr Gly Asn Lys Val Glu Val Ser Thr
        115                 120                 125

Ala Lys Ser Asp Glu Gln Ala Ser Pro Lys Ser Thr Asn Glu Asp Leu
130                 135                 140

Asn Thr Lys Gln Thr Ile Ser Asn Gln Glu Ala Leu Gln Pro Asp Leu
145                 150                 155                 160

Gln Glu Asn Lys Ser Val Val Asn Val Gln Pro Thr Asn Glu Glu Asn
                165                 170                 175

Lys Lys Val Asp Ala Lys Thr Glu Ser Thr Thr Leu Asn Val Lys Ser
            180                 185                 190

Asp Ala Ile Lys Ser Asn Asp Glu Thr Leu Val Asp Asn Asn Ser Asn
        195                 200                 205

Ser Asn Asn Glu Asn Asn Ala Asp Ile Ile Leu Pro Lys Ser Thr Ala
210                 215                 220

Pro Lys Arg Leu Asn Thr Arg Met Arg Ile Ala Ala Val Gln Pro Ser
225                 230                 235                 240

Ser Thr Glu Ala Lys Asn Val Asn Asp Leu Ile Thr Ser Asn Thr Thr
                245                 250                 255

Leu Thr Val Val Asp Ala Asp Lys Asn Lys Ile Val Pro Ala Gln
            260                 265                 270

Asp Tyr Leu Ser Leu Lys Ser Gln Ile Thr Val Asp Asp Lys Val Lys
        275                 280                 285

Ser Gly Asp Tyr Phe Thr Ile Lys Tyr Ser Asp Thr Val Gln Val Tyr
290                 295                 300

Gly Leu Asn Pro Glu Asp Ile Lys Asn Ile Gly Asp Ile Lys Asp Pro
305                 310                 315                 320

Asn Asn Gly Glu Thr Ile Ala Thr Ala Lys His Asp Thr Ala Asn Asn
                325                 330                 335

Leu Ile Thr Tyr Thr Phe Thr Asp Tyr Val Asp Arg Phe Asn Ser Val
            340                 345                 350

Gln Met Gly Ile Asn Tyr Ser Ile Tyr Met Asp Ala Asp Thr Ile Pro
        355                 360                 365
```

-continued

```
Val Ser Lys Asn Asp Val Glu Phe Asn Val Thr Ile Gly Asn Thr Thr
    370                 375                 380

Thr Lys Thr Thr Ala Asn Ile Gln Tyr Pro Asp Tyr Val Val Asn Glu
385                 390                 395                 400

Lys Asn Ser Ile Gly Ser Ala Phe Thr Glu Thr Val Ser His Val Gly
                405                 410                 415

Asn Lys Glu Asn Pro Gly Tyr Tyr Lys Gln Thr Ile Tyr Val Asn Pro
            420                 425                 430

Ser Glu Asn Ser Leu Thr Asn Ala Lys Leu Lys Val Gln Ala Tyr His
        435                 440                 445

Ser Ser Tyr Pro Asn Asn Ile Gly Gln Ile Asn Lys Asp Val Thr Asp
450                 455                 460

Ile Lys Ile Tyr Gln Val Pro Lys Gly Tyr Thr Leu Asn Lys Gly Tyr
465                 470                 475                 480

Asp Val Asn Thr Lys Glu Leu Thr Asp Val Thr Asn Gln Tyr Leu Gln
                485                 490                 495

Lys Ile Thr Tyr Gly Asp Asn Asn Ser Ala Val Ile Asp Phe Gly Asn
            500                 505                 510

Ala Asp Ser Ala Tyr Val Val Met Val Asn Thr Lys Phe Gln Tyr Thr
        515                 520                 525

Asn Ser Glu Ser Pro Thr Leu Val Gln Met Ala Thr Leu Ser Ser Thr
530                 535                 540

Gly Asn Lys Ser Val Ser Thr Gly Asn Ala Leu Gly Phe Thr Asn Asn
545                 550                 555                 560

Gln Ser Gly Gly Ala Gly Gln Glu Val Tyr Lys Ile Gly Asn Tyr Val
                565                 570                 575

Trp Glu Asp Thr Asn Lys Asn Gly Val Gln Glu Leu Gly Glu Lys Gly
            580                 585                 590

Val Gly Asn Val Thr Val Thr Val Phe Asp Asn Asn Thr Asn Thr Lys
        595                 600                 605

Val Gly Glu Ala Val Thr Lys Glu Asp Gly Ser Tyr Leu Ile Pro Asn
610                 615                 620

Leu Pro Asn Gly Asp Tyr Arg Val Glu Phe Ser Asn Leu Pro Lys Gly
625                 630                 635                 640

Tyr Glu Val Thr Pro Ser Lys Gln Gly Asn Asn Glu Glu Leu Asp Ser
                645                 650                 655

Asn Gly Leu Ser Ser Val Ile Thr Val Asn Gly Lys Asp Asn Leu Ser
            660                 665                 670

Ala Asp Leu Gly Ile Tyr Lys Pro Lys Tyr Asn Leu Gly Asp Tyr Val
        675                 680                 685

Trp Glu Asp Thr Asn Lys Asn Gly Ile Gln Asp Gln Asp Glu Lys Gly
690                 695                 700

Ile Ser Gly Val Thr Val Thr Leu Lys Asp Glu Asn Gly Asn Val Leu
705                 710                 715                 720

Lys Thr Val Thr Thr Asp Ala Asp Gly Lys Tyr Lys Phe Thr Asp Leu
                725                 730                 735

Asp Asn Gly Asn Tyr Lys Val Glu Phe Thr Thr Pro Glu Gly Tyr Thr
            740                 745                 750

Pro Thr Thr Val Thr Ser Gly Ser Asp Ile Glu Lys Asp Ser Asn Gly
        755                 760                 765

Leu Thr Thr Thr Gly Val Ile Asn Gly Ala Asp Asn Met Thr Leu Asp
770                 775                 780

Ser Gly Phe Tyr Lys Thr Pro Lys Tyr Asn Leu Gly Asn Tyr Val Trp
```

```
                785                 790                 795                 800
Glu Asp Thr Asn Lys Asp Gly Lys Gln Asp Ser Thr Glu Lys Gly Ile
                    805                 810                 815

Ser Gly Val Thr Val Thr Leu Lys Asn Glu Asn Gly Glu Val Leu Gln
                820                 825                 830

Thr Thr Lys Thr Asp Lys Asp Gly Lys Tyr Gln Phe Thr Gly Leu Glu
                835                 840                 845

Asn Gly Thr Tyr Lys Val Glu Phe Glu Thr Pro Ser Gly Tyr Thr Pro
850                 855                 860

Thr Gln Val Gly Ser Gly Thr Asp Glu Gly Ile Asp Ser Asn Gly Thr
865                 870                 875                 880

Ser Thr Thr Gly Val Ile Lys Asp Lys Asp Asn Asp Thr Ile Asp Ser
                885                 890                 895

Gly Phe Tyr Lys Pro Thr Tyr Asn Leu Gly Asp Tyr Val Trp Glu Asp
                900                 905                 910

Thr Asn Lys Asn Gly Val Gln Asp Lys Asp Glu Lys Gly Ile Ser Gly
                915                 920                 925

Val Thr Val Thr Leu Lys Asp Glu Asn Asp Lys Val Leu Lys Thr Val
                930                 935                 940

Thr Thr Asp Glu Asn Gly Lys Tyr Gln Phe Thr Asp Leu Asn Asn Gly
945                 950                 955                 960

Thr Tyr Lys Val Glu Phe Glu Thr Pro Ser Gly Tyr Thr Pro Thr Ser
                965                 970                 975

Val Thr Ser Gly Asn Asp Thr Glu Lys Asp Ser Asn Gly Leu Thr Thr
                980                 985                 990

Thr Gly Val Ile Lys Asp Ala Asp Asn Met Thr Leu Asp Ser Gly Phe
                995                1000                1005

Tyr Lys Thr Pro Lys Tyr Ser Leu Gly Asp Tyr Val Trp Tyr Asp Ser
                1010                1015                1020

Asn Lys Asp Gly Lys Gln Asp Ser Thr Glu Lys Gly Ile Lys Asp Val
1025                1030                1035                1040

Lys Val Thr Leu Leu Asn Glu Lys Gly Glu Val Ile Gly Thr Thr Lys
                1045                1050                1055

Thr Asp Glu Asn Gly Lys Tyr Cys Phe Asp Asn Leu Asp Ser Gly Lys
                1060                1065                1070

Tyr Lys Val Ile Phe Glu Lys Pro Ala Gly Leu Thr Gln Thr Val Thr
                1075                1080                1085

Asn Thr Thr Glu Asp Asp Lys Asp Ala Asp Gly Gly Glu Val Asp Val
                1090                1095                1100

Thr Ile Thr Asp His Asp Asp Phe Thr Leu Asp Asn Gly Tyr Phe Glu
1105                1110                1115                1120

Glu Asp Thr Ser Asp Ser Asp Ser Asp Ser Asp Ser Asp Ser Asp Ser
                1125                1130                1135

Asp Ser Asp Ser Asp Ser Asp Ser Asp Ser Asp Ser Asp Ser Asp Ser
                1140                1145                1150

Asp Ser Asp Ser Asp Ser Asp Ser Asp Ser Asp Ser Asp Ser Asp Ser
                1155                1160                1165

Asp Ser Asp Ser Asp Ser Asp Ser Asp Ser Asp Ser Asp Ser Asp Ser
                1170                1175                1180

Asp Ser Asp Ser Asp Ser Asp Ser Asp Ser Asp Ser Asp Ser Asp Ser
1185                1190                1195                1200

Asp Ser Asp Ser Asp Ser Asp Ser Asp Ser Asp Ser Asp Ser Asp Ser
                1205                1210                1215
```

Asp Ser Asp Ser Asp Ser Asp Ser Asp Ser Asp Ser
            1220                1225                1230

Asp Ser Asp Ser Asp Ser Asp Ser Asp Ser Asp Ser
        1235                1240                1245

Asp Ser Asp Ser Asp Ser Asp Ser Asp Ser Asp Ser
    1250                1255                1260

Asp Ser Asp Ser Asp Ser Asp Ser Asp Ser Asp Ser
1265                1270                1275                1280

Asp Ser Asp Ser Asp Ser Asp Ala Gly Lys His Thr Pro Val
            1285                1290                1295

Lys Pro Met Ser Thr Thr Lys Asp His His Asn Lys Ala Lys Ala Leu
        1300                1305                1310

Pro Glu Thr Gly Ser Glu Asn Asn Gly Ser Asn Ala Thr Leu Phe
            1315                1320                1325

Gly Gly Leu Phe Ala Ala Leu Gly Ser Leu Leu Leu Phe Gly Arg Arg
        1330                1335                1340

Lys Lys Gln Asn Lys
1345

<210> SEQ ID NO 19
<211> LENGTH: 540
<212> TYPE: PRT
<213> ORGANISM: Staphylococcus aureus

<400> SEQUENCE: 19

Ala Glu Ser Thr Asn Lys Glu Leu Asn Glu Ala Thr Thr Ser Ala Ser
1               5                   10                  15

Asp Asn Gln Ser Ser Asp Lys Val Asp Met Gln Gln Leu Asn Gln Glu
            20                  25                  30

Asp Asn Thr Lys Asn Asp Asn Gln Lys Glu Met Val Ser Ser Gln Gly
        35                  40                  45

Asn Glu Thr Thr Ser Asn Gly Asn Lys Leu Ile Glu Lys Glu Ser Val
    50                  55                  60

Gln Ser Thr Thr Gly Asn Lys Val Glu Val Ser Thr Ala Lys Ser Asp
65                  70                  75                  80

Glu Gln Ala Ser Pro Lys Ser Thr Asn Glu Asp Leu Asn Thr Lys Gln
                85                  90                  95

Thr Ile Ser Asn Gln Glu Ala Leu Gln Pro Asp Leu Gln Glu Asn Lys
            100                 105                 110

Ser Val Val Asn Val Gln Pro Thr Asn Glu Glu Asn Lys Lys Val Asp
        115                 120                 125

Ala Lys Thr Glu Ser Thr Thr Leu Asn Val Lys Ser Asp Ala Ile Lys
    130                 135                 140

Ser Asn Asp Glu Thr Leu Val Asp Asn Asn Ser Asn Ser Asn Asn Glu
145                 150                 155                 160

Asn Asn Ala Asp Ile Ile Leu Pro Lys Ser Thr Ala Pro Lys Arg Leu
                165                 170                 175

Asn Thr Arg Met Arg Ile Ala Ala Val Gln Pro Ser Ser Thr Glu Ala
            180                 185                 190

Lys Asn Val Asn Asp Leu Ile Thr Ser Asn Thr Thr Leu Thr Val Val
        195                 200                 205

Asp Ala Asp Lys Asn Asn Lys Ile Val Pro Ala Gln Asp Tyr Leu Ser
    210                 215                 220

Leu Lys Ser Gln Ile Thr Val Asp Asp Lys Val Lys Ser Gly Asp Tyr

```
                225                 230                 235                 240
Phe Thr Ile Lys Tyr Ser Asp Thr Val Gln Val Tyr Gly Leu Asn Pro
                    245                 250                 255

Glu Asp Ile Lys Asn Ile Gly Asp Ile Lys Asp Pro Asn Asn Gly Glu
                260                 265                 270

Thr Ile Ala Thr Ala Lys His Asp Thr Ala Asn Asn Leu Ile Thr Tyr
                275                 280                 285

Thr Phe Thr Asp Tyr Val Asp Arg Phe Asn Ser Val Gln Met Gly Ile
            290                 295                 300

Asn Tyr Ser Ile Tyr Met Asp Ala Asp Thr Ile Pro Val Ser Lys Asn
305                 310                 315                 320

Asp Val Glu Phe Asn Val Thr Ile Gly Asn Thr Thr Lys Thr Thr
                325                 330                 335

Ala Asn Ile Gln Tyr Pro Asp Tyr Val Val Asn Glu Lys Asn Ser Ile
                340                 345                 350

Gly Ser Ala Phe Thr Glu Thr Val Ser His Val Gly Asn Lys Glu Asn
                355                 360                 365

Pro Gly Tyr Tyr Lys Gln Thr Ile Tyr Val Asn Pro Ser Glu Asn Ser
    370                 375                 380

Leu Thr Asn Ala Lys Leu Lys Val Gln Ala Tyr His Ser Ser Tyr Pro
385                 390                 395                 400

Asn Asn Ile Gly Gln Ile Asn Lys Asp Val Thr Asp Ile Lys Ile Tyr
                405                 410                 415

Gln Val Pro Lys Gly Tyr Thr Leu Asn Lys Gly Tyr Asp Val Asn Thr
                420                 425                 430

Lys Glu Leu Thr Asp Val Thr Asn Gln Tyr Leu Gln Lys Ile Thr Tyr
            435                 440                 445

Gly Asp Asn Asn Ser Ala Val Ile Asp Phe Gly Asn Ala Asp Ser Ala
        450                 455                 460

Tyr Val Val Met Val Asn Thr Lys Phe Gln Tyr Thr Asn Ser Glu Ser
465                 470                 475                 480

Pro Thr Leu Val Gln Met Ala Thr Leu Ser Ser Thr Gly Asn Lys Ser
                485                 490                 495

Val Ser Thr Gly Asn Ala Leu Gly Phe Thr Asn Asn Gln Ser Gly Gly
                500                 505                 510

Ala Gly Gln Glu Val Tyr Lys Ile Gly Asn Tyr Val Trp Glu Asp Thr
                515                 520                 525

Asn Lys Asn Gly Val Gln Glu Leu Gly Glu Lys Gly
        530                 535                 540

<210> SEQ ID NO 20
<211> LENGTH: 199
<212> TYPE: PRT
<213> ORGANISM: Staphylococcus aureus

<400> SEQUENCE: 20

Pro Asp Tyr Val Val Asn Glu Lys Asn Ser Ile Gly Ser Ala Phe Thr
1               5                   10                  15

Glu Thr Val Ser His Val Gly Asn Lys Glu Asn Pro Gly Tyr Tyr Lys
                20                  25                  30

Gln Thr Ile Tyr Val Asn Pro Ser Glu Asn Ser Leu Thr Asn Ala Lys
            35                  40                  45

Leu Lys Val Gln Ala Tyr His Ser Ser Tyr Pro Asn Asn Ile Gly Gln
        50                  55                  60
```

-continued

```
Ile Asn Lys Asp Val Thr Asp Ile Lys Ile Tyr Gln Val Pro Lys Gly
 65                  70                  75                  80

Tyr Thr Leu Asn Lys Gly Tyr Asp Val Asn Thr Lys Glu Leu Thr Asp
             85                  90                  95

Val Thr Asn Gln Tyr Leu Gln Lys Ile Thr Tyr Gly Asp Asn Asn Ser
            100                 105                 110

Ala Val Ile Asp Phe Gly Asn Ala Asp Ser Ala Tyr Val Val Met Val
        115                 120                 125

Asn Thr Lys Phe Gln Tyr Thr Asn Ser Glu Ser Pro Thr Leu Val Gln
    130                 135                 140

Met Ala Thr Leu Ser Ser Thr Gly Asn Lys Ser Val Ser Thr Gly Asn
145                 150                 155                 160

Ala Leu Gly Phe Thr Asn Asn Gln Ser Gly Gly Ala Gly Gln Glu Val
                165                 170                 175

Tyr Lys Ile Gly Asn Tyr Val Trp Glu Asp Thr Asn Lys Asn Gly Val
            180                 185                 190

Gln Glu Leu Gly Glu Lys Gly
            195

<210> SEQ ID NO 21
<211> LENGTH: 516
<212> TYPE: PRT
<213> ORGANISM: Staphylococcus aureus

<400> SEQUENCE: 21

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
 65                 70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240
```

```
Phe Ile Gln Ser Leu Lys Asp Asp Pro Ser Gln Ser Ala Asn Leu Leu
            245                 250                 255

Ala Glu Ala Lys Lys Leu Asn Asp Ala Gln Ala Pro Lys Ala Asp Asn
        260                 265                 270

Lys Phe Asn Lys Glu Gln Gln Asn Ala Phe Tyr Glu Ile Leu His Leu
    275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Asn Asn Lys Pro Gly Lys Glu Asp Asn Asn Lys Pro Gly Lys
            340                 345                 350

Glu Asp Asn Asn Lys Pro Gly Lys Glu Asp Asn Asn Lys Pro Gly Lys
            355                 360                 365

Glu Asp Gly Asn Lys Pro Gly Lys Glu Asp Asn Lys Lys Pro Gly Lys
    370                 375                 380

Glu Asp Gly Asn Lys Pro Gly Lys Glu Asp Asn Lys Pro Gly Lys
385                 390                 395                 400

Glu Asp Gly Asn Lys Pro Gly Lys Glu Asp Gly Asn Lys Pro Gly Lys
                405                 410                 415

Glu Asp Gly Asn Gly Val His Val Val Lys Pro Gly Asp Thr Val Asn
            420                 425                 430

Asp Ile Ala Lys Ala Asn Gly Thr Thr Ala Asp Lys Ile Ala Ala Asp
            435                 440                 445

Asn Lys Leu Ala Asp Lys Asn Met Ile Lys Pro Gly Gln Glu Leu Val
    450                 455                 460

Val Asp Lys Lys Gln Pro Ala Asn His Ala Asp Ala Asn Lys Ala Gln
465                 470                 475                 480

Ala Leu Pro Glu Thr Gly Glu Glu Asn Pro Phe Ile Gly Thr Thr Val
                485                 490                 495

Phe Gly Gly Leu Ser Leu Ala Leu Gly Ala Ala Leu Leu Ala Gly Arg
            500                 505                 510

Arg Arg Glu Leu
        515

<210> SEQ ID NO 22
<211> LENGTH: 289
<212> TYPE: PRT
<213> ORGANISM: Staphylococcus aureus

<400> SEQUENCE: 22

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Asn Asn Phe
    50                  55                  60

Asn Lys Asp Gln Gln Ser Ala Phe Tyr Glu Ile Leu Asn Met Pro Asn
65                  70                  75                  80

Leu Asn Glu Ala Gln Arg Asn Gly Phe Ile Gln Ser Leu Lys Asp Asp
```

```
            85                  90                  95
Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Gln Gln Asn
            115                 120                 125

Ala Phe Tyr Glu Ile Leu Asn Met Pro Asn Leu Asn Glu Glu Gln Arg
            130                 135                 140

Asn Gly Phe Ile Gln Ser Leu Lys Asp Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Gly Phe Ile Gln Ser
            195                 200                 205

Leu Lys Asp Asp Pro Ser Gln Ser Ala Asn Leu Leu Ala Glu Ala Lys
            210                 215                 220

Lys Leu Asn Asp Ala Gln Ala Pro Lys Ala Asp Asn Lys Phe Asn Lys
225                 230                 235                 240

Glu Gln Gln Asn Ala Phe Tyr Glu Ile Leu His Leu Pro Asn Leu Thr
                245                 250                 255

Glu Glu Gln Arg Asn Gly Phe Ile Gln Ser Leu Lys Asp Asp Pro Ser
            260                 265                 270

Val Ser Lys Glu Ile Leu Ala Glu Ala Lys Lys Leu Asn Asp Ala Gln
            275                 280                 285

Ala

<210> SEQ ID NO 23
<211> LENGTH: 130
<212> TYPE: PRT
<213> ORGANISM: Staphylococcus aureus

<400> SEQUENCE: 23

Met Asn Phe Asn Asp Ile Glu Thr Met Val Lys Ser Lys Phe Lys Asp
1               5                   10                  15

Ile Lys Lys His Ala Glu Glu Ile Ala His Glu Ile Glu Val Arg Ser
            20                  25                  30

Gly Tyr Leu Arg Lys Ala Glu Gln Tyr Lys Arg Leu Glu Phe Asn Leu
            35                  40                  45

Ser Phe Ala Leu Asp Asp Ile Glu Ser Thr Ala Lys Asp Val Gln Thr
    50                  55                  60

Ala Lys Ser Ser Ala Asn Lys Asp Ser Val Thr Val Lys Gly Lys Ala
65                  70                  75                  80

Pro Asn Thr Leu Tyr Ile Glu Lys Arg Asn Leu Met Lys Gln Lys Leu
                85                  90                  95

Glu Met Leu Gly Glu Asp Ile Asp Lys Asn Lys Glu Ser Leu Gln Lys
            100                 105                 110

Ala Lys Glu Ile Ala Gly Glu Lys Ala Ser Glu Tyr Phe Asn Lys Ala
            115                 120                 125

Met Asn
    130

<210> SEQ ID NO 24
<211> LENGTH: 97
<212> TYPE: PRT
```

<213> ORGANISM: Staphylococcus aureus

<400> SEQUENCE: 24

Met Ala Met Ile Lys Met Ser Pro Glu Glu Ile Arg Ala Lys Ser Gln
1               5                   10                  15

Ser Tyr Gly Gln Gly Ser Asp Gln Ile Arg Gln Ile Leu Ser Asp Leu
            20                  25                  30

Thr Arg Ala Gln Gly Glu Ile Ala Ala Asn Trp Glu Gly Gln Ala Phe
        35                  40                  45

Ser Arg Phe Glu Glu Gln Phe Gln Gln Leu Ser Pro Lys Val Glu Lys
    50                  55                  60

Phe Ala Gln Leu Leu Glu Glu Ile Lys Gln Gln Leu Asn Ser Thr Ala
65                  70                  75                  80

Asp Ala Val Gln Glu Gln Asp Gln Gln Leu Ser Asn Asn Phe Gly Leu
                85                  90                  95

Gln

<210> SEQ ID NO 25
<211> LENGTH: 104
<212> TYPE: PRT
<213> ORGANISM: Staphylococcus aureus

<400> SEQUENCE: 25

Met Gly Gly Tyr Lys Gly Ile Lys Ala Asp Gly Gly Lys Val Asp Gln
1               5                   10                  15

Ala Lys Gln Leu Ala Ala Lys Thr Ala Lys Asp Ile Glu Ala Cys Gln
            20                  25                  30

Lys Gln Thr Gln Gln Leu Ala Glu Tyr Ile Glu Gly Ser Asp Trp Glu
        35                  40                  45

Gly Gln Phe Ala Asn Lys Val Lys Asp Val Leu Leu Ile Met Ala Lys
    50                  55                  60

Phe Gln Glu Glu Leu Val Gln Pro Met Ala Asp His Gln Lys Ala Ile
65                  70                  75                  80

Asp Asn Leu Ser Gln Asn Leu Ala Lys Tyr Asp Thr Leu Ser Ile Lys
                85                  90                  95

Gln Gly Leu Asp Arg Val Asn Pro
            100

<210> SEQ ID NO 26
<211> LENGTH: 302
<212> TYPE: PRT
<213> ORGANISM: Staphylococcus aureus

<400> SEQUENCE: 26

Met Lys Lys Leu Leu Leu Pro Leu Ile Ile Met Leu Leu Val Leu Ala
1               5                   10                  15

Ala Cys Gly Asn Gln Gly Glu Lys Asn Asn Lys Ala Glu Thr Lys Ser
            20                  25                  30

Tyr Lys Met Asp Asp Gly Lys Thr Val Asp Ile Pro Lys Asp Pro Lys
        35                  40                  45

Arg Ile Ala Val Val Ala Pro Thr Tyr Ala Gly Gly Leu Lys Lys Leu
    50                  55                  60

Gly Ala Asn Ile Val Ala Val Asn Gln Gln Val Asp Gln Ser Lys Val
65                  70                  75                  80

Leu Lys Asp Lys Phe Lys Gly Val Thr Lys Ile Gly Asp Gly Asp Val
                85                  90                  95

```
Glu Lys Val Ala Lys Glu Pro Asp Leu Ile Ile Val Tyr Ser Thr
            100                 105                 110

Asp Lys Asp Ile Lys Lys Tyr Gln Lys Val Ala Pro Thr Val Val
            115                 120                 125

Asp Tyr Asn Lys His Lys Tyr Leu Glu Gln Gln Glu Met Leu Gly Lys
            130                 135                 140

Ile Val Gly Lys Glu Asp Lys Val Lys Ala Trp Lys Lys Asp Trp Glu
145                 150                 155                 160

Glu Thr Thr Ala Lys Asp Gly Lys Glu Ile Lys Lys Ala Ile Gly Gln
                165                 170                 175

Asp Ala Thr Val Ser Leu Phe Asp Glu Phe Asp Lys Lys Leu Tyr Thr
            180                 185                 190

Tyr Gly Asp Asn Trp Gly Arg Gly Gly Glu Val Leu Tyr Gln Ala Phe
            195                 200                 205

Gly Leu Lys Met Gln Pro Glu Gln Gln Lys Leu Thr Ala Lys Ala Gly
            210                 215                 220

Trp Ala Glu Val Lys Gln Glu Gly Ile Gly Lys Tyr Ala Gly Asp Tyr
225                 230                 235                 240

Ile Val Ser Thr Ser Glu Gly Lys Pro Thr Pro Gly Tyr Glu Ser Thr
                245                 250                 255

Asn Met Trp Lys Asn Leu Lys Ala Thr Lys Glu Gly His Ile Val Lys
            260                 265                 270

Val Asp Ala Gly Thr Tyr Trp Tyr Asn Asp Pro Tyr Thr Leu Asp Phe
            275                 280                 285

Met Arg Lys Asp Leu Lys Glu Lys Leu Ile Lys Ala Ala Lys
            290                 295                 300

<210> SEQ ID NO 27
<211> LENGTH: 227
<212> TYPE: PRT
<213> ORGANISM: Staphylococcus aureus

<400> SEQUENCE: 27

Met Lys Asn Ile Leu Lys Val Phe Asn Thr Thr Ile Leu Ala Leu Ile
1               5                   10                  15

Ile Ile Ile Ala Thr Phe Ser Asn Ser Ala Asn Ala Ala Asp Ser Gly
            20                  25                  30

Thr Leu Asn Tyr Glu Val Tyr Lys Tyr Asn Thr Asn Asp Thr Ser Ile
            35                  40                  45

Ala Asn Asp Tyr Phe Asn Lys Pro Ala Lys Tyr Ile Lys Lys Asn Gly
            50                  55                  60

Lys Leu Tyr Val Gln Ile Thr Val Asn His Ser His Trp Ile Thr Gly
65              70                  75                  80

Met Ser Ile Glu Gly His Lys Glu Asn Ile Ile Ser Lys Asn Thr Ala
                85                  90                  95

Lys Asp Glu Arg Thr Ser Glu Phe Glu Val Ser Lys Leu Asn Gly Lys
            100                 105                 110

Ile Asp Gly Lys Ile Asp Val Tyr Ile Asp Glu Lys Val Asn Gly Lys
            115                 120                 125

Pro Phe Lys Tyr Asp His His Tyr Asn Ile Thr Tyr Lys Phe Asn Gly
            130                 135                 140

Pro Thr Asp Val Ala Gly Ala Asn Ala Pro Gly Lys Asp Asp Lys Asn
145                 150                 155                 160

Ser Ala Ser Gly Ser Asp Lys Gly Ser Asp Gly Thr Thr Thr Gly Gln
                165                 170                 175
```

Ser Glu Ser Asn Ser Ser Asn Lys Asp Lys Val Glu Asn Pro Gln Thr
            180                 185                 190

Asn Ala Gly Thr Pro Ala Tyr Ile Tyr Ala Ile Pro Val Ala Ser Leu
            195                 200                 205

Ala Leu Leu Ile Ala Ile Thr Leu Phe Val Arg Lys Lys Ser Lys Gly
210                 215                 220

Asn Val Glu
225

<210> SEQ ID NO 28
<211> LENGTH: 319
<212> TYPE: PRT
<213> ORGANISM: Staphylococcus aureus

<400> SEQUENCE: 28

Met Lys Thr Arg Ile Val Ser Val Thr Thr Leu Leu Leu Gly
1               5                   10                  15

Ser Ile Leu Met Asn Pro Val Ala Asn Ala Ala Asp Ser Asp Ile Asn
            20                  25                  30

Ile Lys Thr Gly Thr Thr Asp Ile Gly Ser Asn Thr Thr Val Lys Thr
            35                  40                  45

Gly Asp Leu Val Thr Tyr Asp Lys Glu Asn Gly Met His Lys Lys Val
50                  55                  60

Phe Tyr Ser Phe Ile Asp Asp Lys Asn His Asn Lys Lys Leu Leu Val
65                  70                  75                  80

Ile Arg Thr Lys Gly Thr Ile Ala Gly Gln Tyr Arg Val Tyr Ser Glu
            85                  90                  95

Glu Gly Ala Asn Lys Ser Gly Leu Ala Trp Pro Ser Ala Phe Lys Val
            100                 105                 110

Gln Leu Gln Leu Pro Asp Asn Glu Val Ala Gln Ile Ser Asp Tyr Tyr
            115                 120                 125

Pro Arg Asn Ser Ile Asp Thr Lys Glu Tyr Met Ser Thr Leu Thr Tyr
            130                 135                 140

Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
            165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
            195                 200                 205

Asp Arg Asp Ser Trp Asn Pro Val Tyr Gly Asn Gln Leu Phe Met Lys
            210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
            245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu His Trp Thr Ser
            275                 280                 285

Thr Asn Trp Lys Gly Thr Asn Thr Lys Asp Lys Trp Ile Asp Arg Ser
            290                 295                 300

Ser Glu Arg Tyr Lys Ile Asp Trp Glu Lys Glu Glu Met Thr Asn

<210> SEQ ID NO 29
<211> LENGTH: 293
<212> TYPE: PRT
<213> ORGANISM: Staphylococcus aureus

<400> SEQUENCE: 29

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290

<210> SEQ ID NO 30
<211> LENGTH: 4
<212> TYPE: PRT
<213> ORGANISM: Artificial Sequence
<220> FEATURE:
<223> OTHER INFORMATION: Tetrapeptide loop replacement

<400> SEQUENCE: 30

Pro Ser Gly Ser
1

<210> SEQ ID NO 31
<211> LENGTH: 258
<212> TYPE: PRT
<213> ORGANISM: Staphylococcus aureus

<400> SEQUENCE: 31

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Pro Ser Gly
            100                 105                 110

Ser Val Gln Pro Asp Phe Lys Thr Ile Leu Glu Ser Pro Thr Asp Lys
        115                 120                 125

Lys Val Gly Trp Lys Val Ile Phe Asn Asn Met Val Asn Gln Asn Trp
    130                 135                 140

Gly Pro Tyr Asp Arg Asp Ser Trp Asn Pro Val Tyr Gly Asn Gln Leu
145                 150                 155                 160

Phe Met Lys Thr Arg Asn Gly Ser Met Lys Ala Ala Asp Asn Phe Leu
                165                 170                 175

Asp Pro Asn Lys Ala Ser Ser Leu Leu Ser Ser Gly Phe Ser Pro Asp
            180                 185                 190

Phe Ala Thr Val Ile Thr Met Asp Arg Lys Ala Ser Lys Gln Gln Thr
        195                 200                 205

Asn Ile Asp Val Ile Tyr Glu Arg Val Arg Asp Asp Tyr Gln Leu His
    210                 215                 220

Trp Thr Ser Thr Asn Trp Lys Gly Thr Asn Thr Lys Asp Lys Trp Ile
225                 230                 235                 240

Asp Arg Ser Ser Glu Arg Tyr Lys Ile Asp Trp Glu Lys Glu Glu Met
                245                 250                 255

Thr Asn
```

<210> SEQ ID NO 32
<211> LENGTH: 258
<212> TYPE: PRT
<213> ORGANISM: Staphylococcus aureus

<400> SEQUENCE: 32

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60
```

```
Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Pro Ser Gly
            100                 105                 110

Ser Val Gln Pro Asp Phe Lys Thr Ile Leu Glu Ser Pro Thr Asp Lys
        115                 120                 125

Lys Val Gly Trp Lys Val Ile Phe Asn Asn Met Val Asn Gln Asn Trp
    130                 135                 140

Gly Pro Tyr Asp Arg Asp Ser Trp Asn Pro Val Tyr Gly Asn Gln Leu
145                 150                 155                 160

Phe Met Lys Thr Arg Asn Gly Ser Met Lys Ala Ala Asp Asn Phe Leu
                165                 170                 175

Asp Pro Asn Lys Ala Ser Ser Leu Leu Ser Ser Gly Phe Ser Pro Asp
            180                 185                 190

Phe Ala Thr Val Ile Thr Met Asp Arg Lys Ala Ser Lys Gln Gln Thr
        195                 200                 205

Asn Ile Asp Val Ile Tyr Glu Arg Val Arg Asp Asp Tyr Gln Leu His
    210                 215                 220

Trp Thr Ser Thr Asn Trp Lys Gly Thr Asn Thr Lys Asp Lys Trp Ile
225                 230                 235                 240

Asp Arg Ser Ser Glu Arg Tyr Lys Ile Asp Trp Glu Lys Glu Glu Met
                245                 250                 255

Thr Asn

<210> SEQ ID NO 33
<211> LENGTH: 50
<212> TYPE: PRT
<213> ORGANISM: Staphylococcus aureus

<400> SEQUENCE: 33

Ala Asp Ser Asp Ile Asn Ile Lys Thr Gly Thr Thr Asp Ile Gly Ser
  1               5                  10                  15

Asn Thr Thr Val Lys Thr Gly Asp Leu Val Thr Tyr Asp Lys Glu Asn
                 20                  25                  30

Gly Met His Lys Lys Val Phe Tyr Ser Phe Ile Asp Asp Lys Asn His
             35                  40                  45

Asn Lys
     50

<210> SEQ ID NO 34
<211> LENGTH: 63
<212> TYPE: PRT
<213> ORGANISM: Staphylococcus aureus

<400> SEQUENCE: 34

Ala Asp Ser Asp Ile Asn Ile Lys Thr Gly Thr Thr Asp Ile Gly Ser
  1               5                  10                  15

Asn Thr Thr Val Lys Thr Gly Asp Leu Val Thr Tyr Asp Lys Glu Asn
                 20                  25                  30

Gly Met His Lys Lys Val Phe Tyr Ser Phe Ile Asp Asp Lys Asn His
             35                  40                  45

Asn Lys Lys Leu Leu Val Ile Arg Thr Lys Gly Thr Ile Ala Gly
     50                  55                  60
```

<210> SEQ ID NO 35
<211> LENGTH: 53
<212> TYPE: PRT
<213> ORGANISM: Staphylococcus aureus

<400> SEQUENCE: 35

Ala Asp Ser Asp Ile Asn Ile Lys Thr Gly Thr Thr Asp Ile Gly Ser
1               5                   10                  15
Asn Thr Thr Val Lys Thr Gly Asp Leu Val Thr Tyr Asp Lys Glu Asn
            20                  25                  30
Gly Met His Lys Lys Val Phe Tyr Ser Phe Ile Asp Asp Lys Asn His
        35                  40                  45
Asn Lys Lys Leu Leu
    50

<210> SEQ ID NO 36
<211> LENGTH: 50
<212> TYPE: PRT
<213> ORGANISM: Staphylococcus aureus

<400> SEQUENCE: 36

Ala Asp Ser Asp Ile Asn Ile Lys Thr Gly Thr Thr Asp Ile Gly Ser
1               5                   10                  15
Asn Thr Thr Val Lys Thr Gly Asp Leu Val Thr Tyr Asp Lys Glu Asn
            20                  25                  30
Gly Met Leu Lys Lys Val Phe Tyr Ser Phe Ile Asp Asp Lys Asn His
        35                  40                  45
Asn Lys
    50

<210> SEQ ID NO 37
<211> LENGTH: 63
<212> TYPE: PRT
<213> ORGANISM: Staphylococcus aureus

<400> SEQUENCE: 37

Ala Asp Ser Asp Ile Asn Ile Lys Thr Gly Thr Thr Asp Ile Gly Ser
1               5                   10                  15
Asn Thr Thr Val Lys Thr Gly Asp Leu Val Thr Tyr Asp Lys Glu Asn
            20                  25                  30
Gly Met Leu Lys Lys Val Phe Tyr Ser Phe Ile Asp Asp Lys Asn His
        35                  40                  45
Asn Lys Lys Leu Leu Val Ile Arg Thr Lys Gly Thr Ile Ala Gly
    50                  55                  60

<210> SEQ ID NO 38
<211> LENGTH: 53
<212> TYPE: PRT
<213> ORGANISM: Staphylococcus aureus

<400> SEQUENCE: 38

Ala Asp Ser Asp Ile Asn Ile Lys Thr Gly Thr Thr Asp Ile Gly Ser
1               5                   10                  15
Asn Thr Thr Val Lys Thr Gly Asp Leu Val Thr Tyr Asp Lys Glu Asn
            20                  25                  30
Gly Met Leu Lys Lys Val Phe Tyr Ser Phe Ile Asp Asp Lys Asn His
        35                  40                  45
Asn Lys Lys Leu Leu
    50

```
<210> SEQ ID NO 39
<211> LENGTH: 256
<212> TYPE: PRT
<213> ORGANISM: Staphylococcus aureus

<400> SEQUENCE: 39

Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
            20                  25                  30

Val Lys Lys Ser Phe Glu Lys Thr Leu Ser Met Tyr Pro Ile Lys Asn
        35                  40                  45

Leu Glu Asp Leu Tyr Asp Lys Glu Gly Tyr Arg Asp Asp Gln Phe Asp
    50                  55                  60

Lys Asn Asp Lys Gly Thr Trp Ile Ile Asn Ser Glu Met Val Ile Gln
65                  70                  75                  80

Pro Asn Asn Glu Asp Met Val Ala Lys Gly Met Val Leu Tyr Met Asn
                85                  90                  95

Arg Asn Thr Lys Thr Thr Asn Gly Tyr Tyr Tyr Val Asp Val Thr Lys
            100                 105                 110

Asp Glu Asp Glu Gly Lys Pro His Asp Asn Glu Lys Arg Tyr Pro Val
        115                 120                 125

Lys Met Val Asp Asn Lys Ile Ile Pro Thr Lys Glu Ile Lys Asp Glu
    130                 135                 140

Lys Ile Lys Lys Glu Ile Glu Asn Phe Lys Phe Phe Val Gln Tyr Gly
145                 150                 155                 160

Asp Phe Lys Asn Leu Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
            180                 185                 190

Tyr Asn Val Lys Gln Leu Arg Lys Arg Tyr Asp Ile Pro Thr Ser Lys
        195                 200                 205

Ala Pro Lys Leu Leu Leu Lys Gly Ser Gly Asn Leu Lys Gly Ser Ser
    210                 215                 220

Val Gly Tyr Lys Asp Ile Glu Phe Thr Phe Val Glu Lys Lys Glu Glu
225                 230                 235                 240

Asn Ile Tyr Phe Ser Asp Ser Leu Asp Tyr Lys Lys Ser Gly Asp Val
                245                 250                 255

<210> SEQ ID NO 40
<211> LENGTH: 256
<212> TYPE: PRT
<213> ORGANISM: Staphylococcus aureus

<400> SEQUENCE: 40

Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
            20                  25                  30

Val Lys Lys Ser Phe Glu Lys Thr Leu Ser Met Tyr Pro Ile Lys Asn
        35                  40                  45

Leu Glu Asp Leu Tyr Asp Lys Glu Gly Tyr Arg Asp Asp Gln Phe Asp
    50                  55                  60

Lys Asn Asp Lys Gly Thr Trp Ile Ile Asn Ser Glu Met Val Ile Gln
65                  70                  75                  80
```

```
Pro Asn Asn Glu Asp Met Val Ala Lys Gly Met Val Leu Tyr Met Asn
                85                  90                  95

Arg Asn Thr Lys Thr Thr Asn Gly Tyr Tyr Tyr Val Asp Val Thr Lys
            100                 105                 110

Asp Glu Asp Glu Gly Lys Pro His Asp Asn Glu Lys Arg Tyr Pro Val
        115                 120                 125

Lys Met Val Asp Asn Lys Ile Ile Pro Thr Lys Glu Ile Lys Asp Glu
    130                 135                 140

Lys Leu Lys Lys Glu Ile Glu Asn Phe Lys Phe Val Gln Tyr Gly
145                 150                 155                 160

Asp Phe Lys Asn Ile Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
            180                 185                 190

Tyr Asn Val Lys Gln Leu Arg Lys Arg Tyr Asp Ile Pro Thr Ser Lys
        195                 200                 205

Ala Pro Lys Leu Leu Lys Gly Ser Gly Asn Leu Lys Gly Ser Ser
    210                 215                 220

Val Gly Tyr Lys Asp Ile Glu Phe Thr Phe Val Glu Lys Lys Glu Glu
225                 230                 235                 240

Asn Ile Tyr Phe Ser Asp Ser Leu Asp Tyr Lys Lys Ser Gly Asp Val
                245                 250                 255

<210> SEQ ID NO 41
<211> LENGTH: 256
<212> TYPE: PRT
<213> ORGANISM: Staphylococcus aureus

<400> SEQUENCE: 41

Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
            20                  25                  30

Val Lys Lys Ser Phe Glu Lys Thr Leu Ser Met Tyr Pro Ile Lys Asn
        35                  40                  45

Leu Glu Asp Leu Tyr Asp Lys Glu Gly Tyr Arg Asp Asp Gln Phe Asp
    50                  55                  60

Lys Asn Asp Lys Gly Thr Trp Ile Ile Asn Ser Glu Met Val Ile Gln
65                  70                  75                  80

Pro Asn Asn Glu Asp Met Val Ala Lys Gly Met Val Leu Tyr Met Asn
                85                  90                  95

Arg Asn Thr Lys Thr Thr Asn Gly Tyr Tyr Tyr Val Asp Val Thr Lys
            100                 105                 110

Asp Glu Asp Glu Gly Lys Pro His Asp Asn Glu Lys Arg Tyr Pro Val
        115                 120                 125

Lys Met Val Asp Asn Lys Ile Ile Pro Thr Lys Glu Ile Lys Asp Glu
    130                 135                 140

Lys Val Lys Lys Glu Ile Glu Asn Phe Lys Phe Val Gln Tyr Gly
145                 150                 155                 160

Asp Phe Lys Asn Ile Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
            180                 185                 190

Tyr Asn Val Lys Gln Leu Arg Lys Arg Tyr Asp Ile Pro Thr Ser Lys
        195                 200                 205
```

```
Ala Pro Lys Leu Leu Lys Gly Ser Gly Asn Leu Lys Gly Ser Ser
    210                 215                 220

Val Gly Tyr Lys Asp Ile Glu Phe Thr Phe Val Glu Lys Glu Glu
225                 230                 235                 240

Asn Ile Tyr Phe Ser Asp Ser Leu Asp Tyr Lys Lys Ser Gly Asp Val
                245                 250                 255
```

<210> SEQ ID NO 42
<211> LENGTH: 256
<212> TYPE: PRT
<213> ORGANISM: Staphylococcus aureus

<400> SEQUENCE: 42

```
Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
                20                  25                  30

Val Lys Lys Ser Phe Glu Lys Thr Leu Ser Met Tyr Pro Ile Lys Asn
            35                  40                  45

Leu Glu Asp Leu Tyr Asp Lys Glu Gly Tyr Arg Asp Asp Gln Phe Asp
50                  55                  60

Lys Asn Asp Lys Gly Thr Trp Ile Ile Asn Ser Glu Met Val Ile Gln
65                  70                  75                  80

Pro Asn Asn Glu Asp Met Val Ala Lys Gly Met Val Leu Tyr Met Asn
                85                  90                  95

Arg Asn Thr Lys Thr Thr Asn Gly Tyr Tyr Tyr Val Ala Val Thr Lys
                100                 105                 110

Asp Glu Asp Glu Gly Lys Pro His Asp Asn Glu Lys Arg Tyr Pro Val
            115                 120                 125

Lys Met Val Asp Asn Lys Ile Ile Pro Thr Lys Glu Ile Lys Asp Glu
130                 135                 140

Lys Leu Lys Lys Glu Ile Glu Asn Phe Lys Phe Val Gln Tyr Gly
145                 150                 155                 160

Asp Phe Lys Asn Val Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
            180                 185                 190

Tyr Asn Val Lys Gln Leu Arg Lys Arg Tyr Asp Ile Pro Thr Ser Lys
            195                 200                 205

Ala Pro Lys Leu Leu Lys Gly Ser Gly Asn Leu Lys Gly Ser Ser
    210                 215                 220

Val Gly Tyr Lys Asp Ile Glu Phe Thr Phe Val Glu Lys Lys Glu Glu
225                 230                 235                 240

Asn Ile Tyr Phe Ser Asp Ser Leu Asp Tyr Lys Lys Ser Gly Asp Val
                245                 250                 255
```

<210> SEQ ID NO 43
<211> LENGTH: 350
<212> TYPE: PRT
<213> ORGANISM: Staphylococcus aureus

<400> SEQUENCE: 43

```
Met Thr Lys His Tyr Leu Asn Ser Lys Tyr Gln Ser Glu Gln Arg Ser
1               5                   10                  15

Ser Ala Met Lys Lys Ile Thr Met Gly Thr Ala Ser Ile Ile Leu Gly
                20                  25                  30
```

Ser Leu Val Tyr Ile Gly Ala Asp Ser Gln Gln Val Asn Ala Ala Thr
            35                  40                  45

Glu Ala Thr Asn Ala Thr Asn Asn Gln Ser Thr Gln Val Ser Gln Ala
 50                  55                  60

Thr Ser Gln Pro Ile Asn Phe Gln Val Gln Lys Asp Gly Ser Ser Glu
 65                  70                  75                  80

Lys Ser His Met Asp Asp Tyr Met Gln His Pro Gly Lys Val Ile Lys
                 85                  90                  95

Gln Asn Asn Lys Tyr Tyr Phe Gln Thr Val Leu Asn Asn Ala Ser Phe
                100                 105                 110

Trp Lys Glu Tyr Lys Phe Tyr Asn Ala Asn Asn Gln Glu Leu Ala Thr
            115                 120                 125

Thr Val Val Asn Asp Asn Lys Lys Ala Asp Thr Arg Thr Ile Asn Val
130                 135                 140

Ala Val Glu Pro Gly Tyr Lys Ser Leu Thr Thr Lys Val His Ile Val
145                 150                 155                 160

Val Pro Gln Ile Asn Tyr Asn His Arg Tyr Thr Thr His Leu Glu Phe
                165                 170                 175

Glu Lys Ala Ile Pro Thr Leu Ala Asp Ala Ala Lys Pro Asn Asn Val
            180                 185                 190

Lys Pro Val Gln Pro Lys Pro Ala Gln Pro Lys Thr Pro Thr Glu Gln
            195                 200                 205

Thr Lys Pro Val Gln Pro Lys Val Glu Lys Val Lys Pro Thr Val Thr
            210                 215                 220

Thr Thr Ser Lys Val Glu Asp Asn His Ser Thr Lys Val Val Ser Thr
225                 230                 235                 240

Asp Thr Thr Lys Asp Gln Thr Lys Thr Gln Thr Ala His Thr Val Lys
                245                 250                 255

Thr Ala Gln Thr Ala Gln Glu Gln Asn Lys Val Gln Thr Pro Val Lys
            260                 265                 270

Asp Val Ala Thr Ala Lys Ser Glu Ser Asn Asn Gln Ala Val Ser Asp
            275                 280                 285

Asn Lys Ser Gln Gln Thr Asn Lys Val Thr Lys His Asn Glu Thr Pro
290                 295                 300

Lys Gln Ala Ser Lys Ala Lys Glu Leu Pro Lys Thr Gly Leu Thr Ser
305                 310                 315                 320

Val Asp Asn Phe Ile Ser Thr Val Ala Phe Ala Thr Leu Ala Leu Leu
                325                 330                 335

Gly Ser Leu Ser Leu Leu Leu Phe Lys Arg Lys Glu Ser Lys
            340                 345                 350

```
<210> SEQ ID NO 44
<211> LENGTH: 145
<212> TYPE: PRT
<213> ORGANISM: Staphylococcus aureus

<400> SEQUENCE: 44
```

Asp Ser Gln Gln Val Asn Ala Ala Thr Glu Ala Thr Asn Ala Thr Asn
1                   5                  10                  15

Asn Gln Ser Thr Gln Val Ser Gln Ala Thr Ser Gln Pro Ile Asn Phe
            20                  25                  30

Gln Val Gln Lys Asp Gly Ser Ser Glu Lys Ser His Met Asp Asp Tyr
            35                  40                  45

Met Gln His Pro Gly Lys Val Ile Lys Gln Asn Asn Lys Tyr Tyr Phe

```
            50                  55                  60
Gln Thr Val Leu Asn Asn Ala Ser Phe Trp Lys Glu Tyr Lys Phe Tyr
 65                  70                  75                  80

Asn Ala Asn Asn Gln Glu Leu Ala Thr Thr Val Val Asn Asp Asn Lys
                 85                  90                  95

Lys Ala Asp Thr Arg Thr Ile Asn Val Ala Val Glu Pro Gly Tyr Lys
            100                 105                 110

Ser Leu Thr Thr Lys Val His Ile Val Val Pro Gln Ile Asn Tyr Asn
                115                 120                 125

His Arg Tyr Thr Thr His Leu Glu Phe Glu Lys Ala Ile Pro Thr Leu
            130                 135                 140

Ala
145

<210> SEQ ID NO 45
<211> LENGTH: 645
<212> TYPE: PRT
<213> ORGANISM: Staphylococcus aureus

<400> SEQUENCE: 45

Met Asn Lys Gln Gln Lys Glu Phe Lys Ser Phe Tyr Ser Ile Arg Lys
 1               5                  10                  15

Ser Ser Leu Gly Val Ala Ser Val Ala Ile Ser Thr Leu Leu Leu Leu
                20                  25                  30

Met Ser Asn Gly Glu Ala Gln Ala Ala Glu Glu Thr Gly Gly Thr
             35                  40                  45

Asn Thr Glu Ala Gln Pro Lys Thr Glu Ala Val Ala Ser Pro Thr Thr
 50                  55                  60

Thr Ser Glu Lys Ala Pro Glu Thr Lys Pro Val Ala Asn Ala Val Ser
 65                  70                  75                  80

Val Ser Asn Lys Glu Val Glu Ala Pro Thr Ser Glu Thr Lys Glu Ala
                 85                  90                  95

Lys Glu Val Lys Glu Val Lys Ala Pro Lys Glu Thr Lys Glu Val Lys
            100                 105                 110

Pro Ala Ala Lys Ala Thr Asn Asn Thr Tyr Pro Ile Leu Asn Gln Glu
            115                 120                 125

Leu Arg Glu Ala Ile Lys Asn Pro Ala Ile Lys Asp Lys Asp His Ser
130                 135                 140

Ala Pro Asn Ser Arg Pro Ile Asp Phe Glu Met Lys Lys Lys Asp Gly
145                 150                 155                 160

Thr Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
            180                 185                 190

Gln Phe Trp Arg Lys Phe Glu Val Tyr Glu Gly Asp Lys Lys Leu Pro
        195                 200                 205

Ile Lys Leu Val Ser Tyr Asp Thr Val Lys Asp Tyr Ala Tyr Ile Arg
    210                 215                 220

Phe Ser Val Ser Asn Gly Thr Lys Ala Val Lys Ile Val Ser Ser Thr
225                 230                 235                 240

His Phe Asn Asn Lys Glu Glu Lys Tyr Asp Tyr Thr Leu Met Glu Phe
                245                 250                 255

Ala Gln Pro Ile Tyr Asn Ser Ala Asp Lys Phe Lys Thr Glu Glu Asp
            260                 265                 270
```

```
Tyr Lys Ala Glu Lys Leu Leu Ala Pro Tyr Lys Lys Ala Lys Thr Leu
            275                 280                 285

Glu Arg Gln Val Tyr Glu Leu Asn Lys Ile Gln Asp Lys Leu Pro Glu
290                 295                 300

Lys Leu Lys Ala Glu Tyr Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val
            340                 345                 350

Tyr Glu Ser Val Glu Asn Asn Glu Ser Met Met Asp Thr Phe Val Lys
        355                 360                 365

His Pro Ile Lys Thr Gly Met Leu Asn Gly Lys Lys Tyr Met Val Met
    370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
            420                 425                 430

Val His Val Lys Thr Ile Asp Tyr Asp Gly Gln Tyr His Val Arg Ile
        435                 440                 445

Val Asp Lys Glu Ala Phe Thr Lys Ala Asn Thr Asp Lys Ser Asn Lys
    450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
        515                 520                 525

Pro Thr Lys Gly Glu Val Glu Ser Ser Ser Thr Thr Pro Thr Lys Val
    530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
        595                 600                 605

Ser Leu Pro Gln Thr Gly Glu Glu Ser Asn Lys Asp Met Thr Leu Pro
    610                 615                 620

Leu Met Ala Leu Leu Ala Leu Ser Ser Ile Val Ala Phe Val Leu Pro
625                 630                 635                 640

Arg Lys Arg Lys Asn
                645

<210> SEQ ID NO 46
<211> LENGTH: 1256
<212> TYPE: PRT
<213> ORGANISM: Staphylococcus aureus

<400> SEQUENCE: 46
```

```
Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu Thr
            20                  25                  30

Thr Gln Asp Gln Thr Thr Asn Lys Asn Val Leu Asp Ser Asn Lys Val
        35                  40                  45

Lys Ala Thr Thr Glu Gln Ala Lys Ala Glu Val Lys Asn Pro Thr Gln
50                  55                  60

Asn Ile Ser Gly Thr Gln Val Tyr Gln Asp Pro Ala Ile Val Gln Pro
65                  70                  75                  80

Lys Thr Ala Asn Asn Lys Thr Gly Asn Ala Gln Val Ser Gln Lys Val
                85                  90                  95

Asp Thr Ala Gln Val Asn Gly Asp Thr Arg Ala Asn Gln Ser Ala Thr
            100                 105                 110

Thr Asn Asn Thr Gln Pro Val Ala Lys Ser Thr Ser Thr Thr Ala Pro
        115                 120                 125

Lys Thr Asn Thr Asn Val Thr Asn Ala Gly Tyr Ser Leu Val Asp Asp
    130                 135                 140

Glu Asp Asp Asn Ser Glu Asn Gln Ile Asn Pro Glu Leu Ile Lys Ser
145                 150                 155                 160

Ala Ala Lys Pro Ala Ala Leu Glu Thr Gln Tyr Lys Thr Ala Ala Pro
                165                 170                 175

Lys Ala Ala Thr Thr Ser Ala Pro Lys Ala Lys Thr Glu Ala Thr Pro
            180                 185                 190

Lys Val Thr Thr Phe Ser Ala Ser Ala Gln Pro Arg Ser Val Ala Ala
        195                 200                 205

Thr Pro Lys Thr Ser Leu Pro Lys Tyr Lys Pro Gln Val Asn Ser Ser
    210                 215                 220

Ile Asn Asp Tyr Ile Cys Lys Asn Asn Leu Lys Ala Pro Lys Ile Glu
225                 230                 235                 240

Glu Asp Tyr Thr Ser Tyr Phe Pro Lys Tyr Ala Tyr Arg Asn Gly Val
                245                 250                 255

Gly Arg Pro Glu Gly Ile Val Val His Asp Thr Ala Asn Asp Arg Ser
            260                 265                 270

Thr Ile Asn Gly Glu Ile Ser Tyr Met Lys Asn Asn Tyr Gln Asn Ala
        275                 280                 285

Phe Val His Ala Phe Val Asp Gly Asp Arg Ile Ile Glu Thr Ala Pro
    290                 295                 300

Thr Asp Tyr Leu Ser Trp Gly Val Gly Ala Val Gly Asn Pro Arg Phe
305                 310                 315                 320

Ile Asn Val Glu Ile Val His Thr His Asp Tyr Ala Ser Phe Ala Arg
                325                 330                 335

Ser Met Asn Asn Tyr Ala Asp Tyr Ala Ala Thr Gln Leu Gln Tyr Tyr
            340                 345                 350

Gly Leu Lys Pro Asp Ser Ala Glu Tyr Asp Gly Asn Gly Thr Val Trp
        355                 360                 365

Thr His Tyr Ala Val Ser Lys Tyr Leu Gly Gly Thr Asp His Ala Asp
    370                 375                 380

Pro His Gly Tyr Leu Arg Ser His Asn Tyr Ser Tyr Asp Gln Leu Tyr
385                 390                 395                 400

Asp Leu Ile Asn Glu Lys Tyr Leu Ile Lys Met Gly Lys Val Ala Pro
                405                 410                 415
```

```
Trp Gly Thr Gln Ser Thr Thr Thr Pro Thr Thr Pro Ser Lys Pro Thr
            420                 425                 430

Thr Pro Ser Lys Pro Ser Thr Gly Lys Leu Thr Val Ala Ala Asn Asn
        435                 440                 445

Gly Val Ala Gln Ile Lys Pro Thr Asn Ser Gly Leu Tyr Thr Thr Val
    450                 455                 460

Tyr Asp Lys Thr Gly Lys Ala Thr Asn Glu Val Gln Lys Thr Phe Ala
465                 470                 475                 480

Val Ser Lys Thr Ala Thr Leu Gly Asn Gln Lys Phe Tyr Leu Val Gln
                485                 490                 495

Asp Tyr Asn Ser Gly Asn Lys Phe Gly Trp Val Lys Glu Gly Asp Val
            500                 505                 510

Val Tyr Asn Thr Ala Lys Ser Pro Val Asn Val Asn Gln Ser Tyr Ser
        515                 520                 525

Ile Lys Pro Gly Thr Lys Leu Tyr Thr Val Pro Trp Gly Thr Ser Lys
    530                 535                 540

Gln Val Ala Gly Ser Val Ser Gly Ser Asn Gln Thr Phe Lys Ala
545                 550                 555                 560

Ser Lys Gln Gln Gln Ile Asp Lys Ser Ile Tyr Leu Tyr Gly Ser Val
                565                 570                 575

Asn Gly Lys Ser Gly Trp Val Ser Lys Ala Tyr Leu Val Asp Thr Ala
            580                 585                 590

Lys Pro Thr Pro Thr Pro Thr Pro Lys Pro Ser Thr Pro Thr Thr Asn
        595                 600                 605

Asn Lys Leu Thr Val Ser Ser Leu Asn Gly Val Ala Gln Ile Asn Ala
    610                 615                 620

Lys Asn Asn Gly Leu Phe Thr Thr Val Tyr Asp Lys Thr Gly Lys Pro
625                 630                 635                 640

Thr Lys Glu Val Gln Lys Thr Phe Ala Val Thr Lys Glu Ala Ser Leu
                645                 650                 655

Gly Gly Asn Lys Phe Tyr Leu Val Lys Asp Tyr Asn Ser Pro Thr Leu
            660                 665                 670

Ile Gly Trp Val Lys Gln Gly Asp Val Ile Tyr Asn Asn Ala Lys Ser
        675                 680                 685

Pro Val Asn Val Met Gln Thr Tyr Thr Val Lys Pro Gly Thr Lys Leu
    690                 695                 700

Tyr Ser Val Pro Trp Gly Thr Tyr Lys Gln Glu Ala Gly Ala Val Ser
705                 710                 715                 720

Gly Thr Gly Asn Gln Thr Phe Lys Ala Thr Lys Gln Gln Gln Ile Asp
                725                 730                 735

Lys Ser Ile Tyr Leu Phe Gly Thr Val Asn Gly Lys Ser Gly Trp Val
            740                 745                 750

Ser Lys Ala Tyr Leu Ala Val Pro Ala Ala Pro Lys Lys Ala Val Ala
        755                 760                 765

Gln Pro Lys Thr Ala Val Lys Ala Tyr Thr Val Thr Lys Pro Gln Thr
    770                 775                 780

Thr Gln Thr Val Ser Lys Ile Ala Gln Val Lys Pro Asn Asn Thr Gly
785                 790                 795                 800

Ile Arg Ala Ser Val Tyr Glu Lys Thr Ala Lys Asn Gly Ala Lys Tyr
                805                 810                 815

Ala Asp Arg Thr Phe Tyr Val Thr Lys Glu Arg Ala His Gly Asn Glu
            820                 825                 830

Thr Tyr Val Leu Leu Asn Asn Thr Ser His Asn Ile Pro Leu Gly Trp
```

```
                835                 840                 845
Phe Asn Val Lys Asp Leu Asn Val Gln Asn Leu Gly Lys Glu Val Lys
850                 855                 860

Thr Thr Gln Lys Tyr Thr Val Asn Lys Ser Asn Asn Gly Leu Ser Met
865                 870                 875                 880

Val Pro Trp Gly Thr Lys Asn Gln Val Ile Leu Thr Gly Asn Asn Ile
                885                 890                 895

Ala Gln Gly Thr Phe Asn Ala Thr Lys Gln Val Ser Val Gly Lys Asp
                900                 905                 910

Val Tyr Leu Tyr Gly Thr Ile Asn Asn Arg Thr Gly Trp Val Asn Ala
                915                 920                 925

Lys Asp Leu Thr Ala Pro Thr Ala Val Lys Pro Thr Thr Ser Ala Ala
930                 935                 940

Lys Asp Tyr Asn Tyr Thr Tyr Val Ile Lys Asn Gly Asn Gly Tyr Tyr
945                 950                 955                 960

Tyr Val Thr Pro Asn Ser Asp Thr Ala Lys Tyr Ser Leu Lys Ala Phe
                965                 970                 975

Asn Glu Gln Pro Phe Ala Val Val Lys Glu Gln Val Ile Asn Gly Gln
                980                 985                 990

Thr Trp Tyr Tyr Gly Lys Leu Ser Asn Gly Lys Leu Ala Trp Ile Lys
                995                1000                1005

Ser Thr Asp Leu Ala Lys Glu Leu Ile Lys Tyr Asn Gln Thr Gly Met
    1010                1015                1020

Thr Leu Asn Gln Val Ala Gln Ile Gln Ala Gly Leu Gln Tyr Lys Pro
1025                1030                1035                1040

Gln Val Gln Arg Val Pro Gly Lys Trp Thr Asp Ala Lys Phe Asn Asp
                1045                1050                1055

Val Lys His Ala Met Asp Thr Lys Arg Leu Ala Gln Asp Pro Ala Leu
                1060                1065                1070

Lys Tyr Gln Phe Leu Arg Leu Asp Gln Pro Gln Asn Ile Ser Ile Asp
                1075                1080                1085

Lys Ile Asn Gln Phe Leu Lys Gly Lys Gly Val Leu Glu Asn Gln Gly
    1090                1095                1100

Ala Ala Phe Asn Lys Ala Ala Gln Met Tyr Gly Ile Asn Glu Val Tyr
1105                1110                1115                1120

Leu Ile Ser His Ala Leu Leu Glu Thr Gly Asn Gly Thr Ser Gln Leu
                1125                1130                1135

Ala Lys Gly Ala Asp Val Val Asn Asn Lys Val Val Thr Asn Ser Asn
                1140                1145                1150

Thr Lys Tyr His Asn Val Phe Gly Ile Ala Ala Tyr Asp Asn Asp Pro
                1155                1160                1165

Leu Arg Glu Gly Ile Lys Tyr Ala Lys Gln Ala Gly Trp Asp Thr Val
                1170                1175                1180

Ser Lys Ala Ile Val Gly Gly Ala Lys Phe Ile Gly Asn Ser Tyr Val
1185                1190                1195                1200

Lys Ala Gly Gln Asn Thr Leu Tyr Lys Met Arg Trp Asn Pro Ala His
                1205                1210                1215

Pro Gly Thr His Gln Tyr Ala Thr Asp Val Asp Trp Ala Asn Ile Asn
                1220                1225                1230

Ala Lys Ile Ile Lys Gly Tyr Tyr Asp Lys Ile Gly Glu Val Gly Lys
                1235                1240                1245

Tyr Phe Asp Ile Pro Gln Tyr Lys
                1250                1255
```

-continued

<210> SEQ ID NO 47
<211> LENGTH: 6
<212> TYPE: PRT
<213> ORGANISM: Artificial Sequence
<220> FEATURE:
<223> OTHER INFORMATION: linker

<400> SEQUENCE: 47

Gly Ser Gly Gly Gly Gly
1               5

<210> SEQ ID NO 48
<211> LENGTH: 8
<212> TYPE: PRT
<213> ORGANISM: Artificial Sequence
<220> FEATURE:
<223> OTHER INFORMATION: linker

<400> SEQUENCE: 48

Gly Ser Gly Ser Gly Gly Gly Gly
1               5

<210> SEQ ID NO 49
<211> LENGTH: 6
<212> TYPE: PRT
<213> ORGANISM: Artificial Sequence
<220> FEATURE:
<223> OTHER INFORMATION: linker

<400> SEQUENCE: 49

Ala Ser Gly Gly Gly Ser
1               5

<210> SEQ ID NO 50
<211> LENGTH: 18
<212> TYPE: DNA
<213> ORGANISM: Artificial Sequence
<220> FEATURE:
<223> OTHER INFORMATION: Sequence encoding SEQ ID NO: 49

<400> SEQUENCE: 50
gctagcggtg gcggatcc                                                 18

<210> SEQ ID NO 51
<211> LENGTH: 6
<212> TYPE: PRT
<213> ORGANISM: Artificial Sequence
<220> FEATURE:
<223> OTHER INFORMATION: hexahistidine tag

<400> SEQUENCE: 51

His His His His His His
1               5

<210> SEQ ID NO 52
<211> LENGTH: 207
<212> TYPE: PRT
<213> ORGANISM: Staphylococcus aureus

<400> SEQUENCE: 52

Met Ala Met Ile Lys Met Ser Pro Glu Glu Ile Arg Ala Lys Ser Gln
1               5                   10                  15

Ser Tyr Gly Gln Gly Ser Asp Gln Ile Arg Gln Ile Leu Ser Asp Leu
            20                  25                  30

Thr Arg Ala Gln Gly Glu Ile Ala Ala Asn Trp Glu Gly Gln Ala Phe
            35                  40                  45

Ser Arg Phe Glu Glu Gln Phe Gln Gln Leu Ser Pro Lys Val Glu Lys
 50                  55                  60

Phe Ala Gln Leu Leu Glu Glu Ile Lys Gln Gln Leu Asn Ser Thr Ala
 65                  70                  75                  80

Asp Ala Val Gln Glu Gln Asp Gln Leu Ser Asn Asn Phe Gly Leu
                 85                  90                  95

Gln Ala Ser Gly Gly Ser Met Gly Gly Tyr Lys Gly Ile Lys Ala
                100                 105                 110

Asp Gly Gly Lys Val Asp Gln Ala Lys Gln Leu Ala Ala Lys Thr Ala
                115                 120                 125

Lys Asp Ile Glu Ala Cys Gln Lys Gln Thr Gln Gln Leu Ala Glu Tyr
        130                 135                 140

Ile Glu Gly Ser Asp Trp Glu Gly Gln Phe Ala Asn Lys Val Lys Asp
145                 150                 155                 160

Val Leu Leu Ile Met Ala Lys Phe Gln Glu Leu Val Gln Pro Met
                165                 170                 175

Ala Asp His Gln Lys Ala Ile Asp Asn Leu Ser Gln Asn Leu Ala Lys
                180                 185                 190

Tyr Asp Thr Leu Ser Ile Lys Gln Gly Leu Asp Arg Val Asn Pro
                195                 200                 205

<210> SEQ ID NO 53
<211> LENGTH: 618
<212> TYPE: DNA
<213> ORGANISM: Staphylococcus aureus

<400> SEQUENCE: 53
atggcaatga ttaagatgag tccagaggaa atcagagcaa atcgcaatc ttacgggcaa     60 ggttcagacc aaatccgtca aattttatct gatttaacac gtgcacaagg tgaaattgca    120
gcgaactggg aaggtcaagc tttcagccgt ttcgaagagc aattccaaca acttagtcct    180
aaagtagaaa aatttgcaca attattgaa gaaattaaac aacaattgaa tagcactgct    240
gatgccgttc aagaacaaga ccaacaactt tctaataatt tcggtttgca agctagcggt    300
ggcggatccg gtggatataa aggtattaaa gcagatggtg gcaaggttga tcaagcgaaa    360
caattagcgc aaaaacagc taaagatatt gaagcatgtc aaaagcaaac gcaacagctc    420
gctgagtata tcgaaggtag tgattgggaa ggacagttcg ccaataaggt gaaagatgtg    480
ttactcatta tggcaaagtt tcaagaagaa ttagtacaac cgatggctga ccatcaaaaa    540
gcaattgata acttaagtca aaatctagcg aaatacgata cattatcaat taagcaaggg    600
cttgataggg tgaaccca                                                  618

<210> SEQ ID NO 54
<211> LENGTH: 207
<212> TYPE: PRT
<213> ORGANISM: Staphylococcus aureus

<400> SEQUENCE: 54

Met Gly Gly Tyr Lys Gly Ile Lys Ala Asp Gly Gly Lys Val Asp Gln
  1               5                  10                  15

Ala Lys Gln Leu Ala Ala Lys Thr Ala Lys Asp Ile Glu Ala Cys Gln
             20                  25                  30

Lys Gln Thr Gln Gln Leu Ala Glu Tyr Ile Glu Gly Ser Asp Trp Glu
         35                  40                  45

```
Gly Gln Phe Ala Asn Lys Val Lys Asp Val Leu Leu Ile Met Ala Lys
            50                  55                  60

Phe Gln Glu Glu Leu Val Gln Pro Met Ala Asp His Gln Lys Ala Ile
 65                  70                  75                  80

Asp Asn Leu Ser Gln Asn Leu Ala Lys Tyr Asp Thr Leu Ser Ile Lys
                 85                  90                  95

Gln Gly Leu Asp Arg Val Asn Pro Ala Ser Gly Gly Gly Ser Met Ala
                100                 105                 110

Met Ile Lys Met Ser Pro Glu Glu Ile Arg Ala Lys Ser Gln Ser Tyr
            115                 120                 125

Gly Gln Gly Ser Asp Gln Ile Arg Gln Ile Leu Ser Asp Leu Thr Arg
            130                 135                 140

Ala Gln Gly Glu Ile Ala Ala Asn Trp Glu Gly Gln Ala Phe Ser Arg
145                 150                 155                 160

Phe Glu Glu Gln Phe Gln Gln Leu Ser Pro Lys Val Glu Lys Phe Ala
                165                 170                 175

Gln Leu Leu Glu Glu Ile Lys Gln Gln Leu Asn Ser Thr Ala Asp Ala
            180                 185                 190

Val Gln Glu Gln Asp Gln Leu Ser Asn Asn Phe Gly Leu Gln
            195                 200                 205

<210> SEQ ID NO 55
<211> LENGTH: 5
<212> TYPE: PRT
<213> ORGANISM: Artificial Sequence
<220> FEATURE:
<223> OTHER INFORMATION: Motif

<400> SEQUENCE: 55

Leu Pro Lys Thr Gly
1               5

<210> SEQ ID NO 56
<211> LENGTH: 4
<212> TYPE: PRT
<213> ORGANISM: Artificial Sequence
<220> FEATURE:
<223> OTHER INFORMATION: Poly-glycine linker

<400> SEQUENCE: 56

Gly Gly Gly Gly
1
```